(12) United States Patent
Thurairatnam et al.

(10) Patent No.: US 7,482,448 B2
(45) Date of Patent: Jan. 27, 2009

(54) COMPOUNDS AND COMPOSITIONS AS CATHEPSIN INHIBITORS

(75) Inventors: Sukanthini Thurairatnam, Bedminster, NJ (US); David John Aldous, Gillette, NJ (US); Vincent Leroy, Vitry-Sur-Seine (FR); Andreas Paul Timm, Bridgewater, NJ (US)

(73) Assignee: Aventis Pharmaceuticals Inc., Bridgewater, NJ (US)

( * ) Notice: Subject to any disclaimer, the term of this patent is extended or adjusted under 35 U.S.C. 154(b) by 45 days.

(21) Appl. No.: 11/409,601

(22) Filed: Apr. 24, 2006

(65) Prior Publication Data
US 2006/0189657 A1    Aug. 24, 2006

Related U.S. Application Data

(63) Continuation of application No. PCT/US2004/035282, filed on Oct. 22, 2004.

(51) Int. Cl.
*C07D 413/12* (2006.01)
*C07D 413/14* (2006.01)
*C07D 265/30* (2006.01)
*C07D 267/10* (2006.01)

(52) U.S. Cl. ............... 544/138; 544/163; 544/168; 544/139; 544/137; 540/544

(58) Field of Classification Search ............ 544/137, 544/138, 139, 163, 168; 540/544
See application file for complete search history.

(56) References Cited

U.S. PATENT DOCUMENTS

| 4,153,688 | A |   | 5/1979  | Dimicoli et al. |
|-----------|---|---|---------|-----------------|
| 5,223,485 | A |   | 6/1993  | Kawai et al.    |
| 5,276,137 | A |   | 1/1994  | Ojima et al.    |
| 6,153,591 | A | * | 11/2000 | Cai et al. ............... 514/19 |
| 6,403,587 | B1| * | 6/2002  | Kath et al. ............... 514/249 |
| 6,423,869 | B1|   | 7/2002  | Miyagawa et al. |
| 6,455,502 | B1|   | 9/2002  | Bryant et al.   |
| 6,576,630 | B1|   | 6/2003  | Link            |
| 6,867,284 | B1|   | 3/2005  | Matassa et al.  |
| 2003/0119827 | A1 | 6/2003 | Hickey et al. |
| 2003/0232863 | A1 | 12/2003 | Bayly et al. |
| 2003/0232864 | A1 | 12/2003 | Link |
| 2004/0142876 | A1 | 7/2004 | Colarusso et al. |
| 2004/0142999 | A1 | 7/2004 | Graupe |
| 2004/0198982 | A1 | 10/2004 | Prasit et al. |
| 2005/0240001 | A1 | 10/2005 | Evers et al. |
| 2005/0288336 | A1 | 12/2005 | Graupe et al. |

FOREIGN PATENT DOCUMENTS

FR    2605009    4/1988
JP    08165274   6/1996

OTHER PUBLICATIONS

Arai, et al., The Conformation of de Novo Designed Amphiphilic Peptides with Six or Nine L -2-(2,2,2,-Trifluoroethyl)glycines as the Hydrophobic Amino Acid, Bull. Chem. Soc. JPN; 2000; 73:2; pp. 439-445.
Babb, et al., Omega, omega, omega-Trifluoroamino Acids, J. of Org. Chem.; 35:5; 1970; pp.1438-1440.
Bennett, et al., The identification of alpha-ketoamides as potent inhibitors of Hepatitis C Virus NS3-4A Proteinase, Bioorganic & Medicinal Chem. Let., Oxford, G.B.; 11:3; Feb. 2, 2001; pp. 355-357.
Burger, et al., Synthesis of (2S)-4,4-difluoroproline, (2S,4R)-4-fluoroproline and their derivatives from (S)-aspartic acid, J. of Fluorine Chem.; 66; 1994; pp. 87-90.
Chen, et al., alpha-Aminoamides from a Carbamoylsilane and Aldehyde Imines, Tetrahedron Let.; 44:43; 2003; pp. 8025-8027.
Ojima, et al., New Potent Enkephalin Analogs Containing Trifluoromethyfamino Acid Residues, Bioorganic & Medicinal Chem. Let. 2:3, 1992, pp. 219-222.
Orvieto, et al., Novel, Potent Phenethylamide Inhibitors of the Hepatitis C Virus (HCV) NS3 Protease, Bioorganic & Medicinal Chem. Let., Oxford, GB; 13:16; Aug. 18, 2003; pp. 2745-2748.
Takeuchi et al., Age-Related Amyloid Beta Deposition in Transgenic Mice Overexpressing Both Alzheimer Mutant Presenilin 1 and Amyloid Beta Precursor Protein Swedish Mutant Is Not Associated with Global Neuronal Loss, Am. J. or Pathology, vol. 157, No. 1, Jul. 2000, pp. 331-339.

* cited by examiner

*Primary Examiner*—Kamal A Saeed
*Assistant Examiner*—Jason Nolan
(74) *Attorney, Agent, or Firm*—Fox Rothschild LLP

(57) ABSTRACT

Novel inhibitors of cathepsin S, K, B, and L, the pharmaceutically acceptable salts and N-oxides thereof, their uses as therapeutic agents and the methods of their making.

1 Claim, No Drawings

COMPOUNDS AND COMPOSITIONS AS CATHEPSIN INHIBITORS

CROSS-REFERENCE TO RELATED APPLICATIONS

This is a continuation of International Patent Application No. PCT/US2004/035282, filed Oct. 22, 2004, which is incorporated herein by reference in its entirety.

FIELD OF THE INVENTION

This invention relates to the use of novel difluoro derivatives for treating diseases associated with cysteine protease and, particularly, diseases associated with activity of cathepsin S, K, and B. This invention also relates to processes of making such compounds.

BACKGROUND OF THE INVENTION

Cysteine proteases represent a class of peptidases characterized by the presence of a cysteine residue in the catalytic site of the enzyme. Cysteine proteases are associated with the normal degradation and processing of proteins. The aberrant activity of cysteine proteases, for example, as a result of increased expression or enhanced activation, however, may have pathological consequences. In this regard, certain cysteine proteases are associated with a number of disease states, including arthritis, atherosclerosis, emphysema, osteoporosis, muscular dystrophy, inflammation, tumor invasion, glomerulonephritis, periodontal disease, metachromatic leukodystrophy and others.

An increase in cathepsin activity such as, for example, cathepsin S, contributes to the pathology and/or symptomatology of a number of diseases such as, for example, autoimmune disorders, including, but not limited to, juvenile onset diabetes, multiple sclerosis, pemphigus vulgaris, Graves' disease, myasthenia gravis, systemic lupus erythemotasus, irritable bowel disease, rheumatoid arthritis and Hashimoto's thyroiditis, allergic disorders including but not limited to, asthma, and allogeneic immune responses, including, but not limited to, organ transplants or tissue grafts. Cathepsin S is also implicated in disorders involving excessive elastolysis, such as chronic obstructive pulmonary disease (e.g., emphysema), bronchiolitis, excessive airway elastolysis in asthma and bronchitis, pneumonities and cardiovascular disease such as plaque rupture and atheroma. Cathepsin S is implicated in fibril formation and, therefore, inhibitors of cathepsin S may be of use in treatment of systemic amyloidosis.

The activity of, for example, cathepsin B in synovial fluid is significantly elevated in osteoarthritis models (F. Mehraban Ann. Rheum. Dis. 1997; 56, 108-115). Similarly, cathepsin K is a critical protease in synovial fibroblast-mediated collagen degradation (W.-S. Hou (et al.) Am. J. Pathol. 2001, 159, 2167-2177). Thus, inhibition of Cathepsin B and K, for example, is a useful method for the treatment of degenerative joint diseases such as, for example, osteoarthritis. Cathepsin K inhibition, for example, leads to inhibition of bone resorption (G. B. Stroup (et al.) J. Bone Mineral Res. 2001, 16, 1739-1746). Cathepsin K inhibitors are, therefore, useful for the treatment of osteoporosis.

It is known in the art that cathepsins play an important role in the degradation of connective tissues, the generation of bioactive proteins and antigen processing. They have been implicated in osteoporosis, muscular dystrophy, bronchitis, emphysema, viral infection, cancer metastasis and neurodegenerative diseases, such as Alzheimer's disease and Huntington's disease. Recently, increased interest in cathepsin inhibitors has been generated with potential therapeutic targets, such as cathepsin K or cathepsin L for osteoporosis and cathepsin S for immune modulation (W. Kim., K. Kang. Expert Opin. Ther. Pat. 2002, 12, 419-432). An increase in cathepsin K or B activity contributes to the pathology and/or symptomatology of a number of diseases. Accordingly, molecules that inhibit the activity of cathepsin protease are useful as therapeutic agents in the treatment of such diseases.

SUMMARY OF THE INVENTION

In one aspect of the present invention, compounds are provided that inhibit the enzymatic activity of cathepsin S, B, and K and have a structure of formula (I):

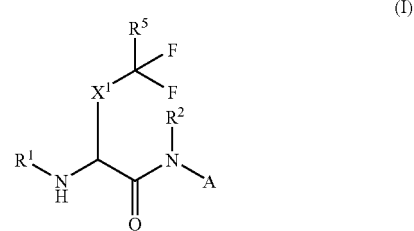

wherein
A is

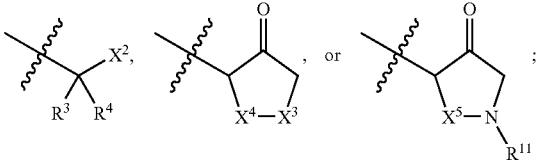

$X^1$ is methylene, ethylene or a bond;
$X^2$ is CN, CHO, C(O)$R^6$, C(O)C(O)N$R^7R^7$, C(O)C(O)N$R^7R^8$, C(O)C(O)$R^{13}$, C(O)C(O)O$R^{13}$, C(O)CH$_2$X$^3R^{13}$;
$X^3$ is selected from the group consisting of O, S(O)$_n$, CO, CONH, NHCO, NHSO$_2$ and SO$_2$NH;
$X^4$ is CH($R^{12}$) or CH($R^{12}$)—CH$_2$;
$X^5$ is methylene, ethylene, propylene or a bond;
$X^6$ is a bond or (C$_{1-2}$)alkylene;
$R^1$ is H, $R^{13}$C(O)—, $R^{13}$S(O)$_2$—, $R^{13}$OC(O)—, $R^8R^7$NC(O)—, $R^8R^7$NS(O)$_2$—; $R^{13}$S(O)$_2$NC(O)— or $R^{13}$C(O)NS(O)$_2$—; or $R^1$ is selected from the group consisting of (C$_{1-9}$)alkyl, (C$_{3-12}$)cycloalkyl(C$_{0-6}$)alkyl, hetero(C$_{5-12}$)cycloalkyl(C$_{0-6}$)alkyl, (C$_{6-12}$)aryl(C$_{0-6}$)alkyl and hetero(C$_{5-13}$)aryl(C$_{0-6}$)alkyl, each of which is optionally substituted by 1 to 5 radicals independently selected from a group consisting of (C$_{1-4}$)alkyl, cyano, halo, halo-substituted (C$_{1-4}$)alkyl, —X$^6$NR$^9R^9$, —X$^6$OR$^9$, —X$^6$SR$^9$, —X$^6$C(O)NR$^9R^9$, —X$^6$OC(O)NR$^9R^9$, —X$^6$C(O)OR$^9$, —X$^6$NC(O)OR$^9$, —X$^6$S(O)R$^{10}$, —X$^6$S(O)$_2R^{10}$ and —X$^6$C(O)R$^{10}$;
$R^2$ is selected from the group consisting of hydrogen, (C$_{1-6}$)alkyl, (C$_{3-12}$)cycloalkyl(C$_{0-6}$)alkyl, hetero(C$_{5-12}$)cycloalkyl(C$_{0-6}$)alkyl, (C$_{6-12}$)aryl(C$_{0-6}$)alkyl or hetero(C$_{5-12}$)aryl(C$_{0-6}$)alkyl;
$R^3$ is selected from the group consisting of H, (C$_{1-6}$)alkyl, (C$_{3-12}$)cycloalkyl(C$_{0-6}$)alkyl, hetero(C$_{5-12}$)cycloalkyl(C$_{0-6}$)alkyl, (C$_{6-12}$)aryl(C$_{0-6}$)alkyl or hetero(C$_{5-13}$)aryl(C$_{0-6}$)alkyl optionally is substituted by 1 to 5 radicals independently selected from a group consisting of $(C_{1-4})$alkyl, cyano, halo, halo-substituted $(C_{1-4})$alkyl, $-X^6NR^9R^9$, $-X^6OR^9$, $-X^6SR^9$, $-X^6C(O)NR^9R^9$, $-X^6OC(O)NR^9R^9$, $-X^6(O)OR^9$, $-X^6NC(O)OR^9$, $-X^6S(O)R^{10}$, $-X^6S(O)_2R^{10}$ and $-X^6C(O)R^{10}$;

$R^4$ is H or $(C_{1-6})$alkyl; or $R^3$ and $R^4$ taken together with the carbon atom to which both $R^3$ and $R^4$ are attached to form $(C_{3-8})$cycloalkylene or $(C_{3-8})$heterocycloalkylene;

$R^5$ is H, F, or $R^5$ is $(C_{1-9})$alkyl, $(C_{3-12})$cycloalkyl$(C_{0-6})$alkyl, hetero$(C_{3-12})$cycloalkyl$(C_{0-6})$alkyl, $(C_{6-12})$aryl$(C_{0-6})$alkyl, hetero$(C_{5-13})$aryl$(C_{0-6})$alkyl each optionally substituted by 1 to 5 radicals independently selected from a group consisting of $(C_{1-4})$alkyl, cyano, halo, halo-substituted $(C_{1-4})$alkyl, $-X^6NR^9R^9$, $-X^6OR^9$, $-X^6SR^9$, $-X^6C(O)NR^9R^9$, $-X^6OC(O)NR^9R^9$, $-X^6C(O)OR^9$, $-X^6NC(O)OR^9$, $-X^6S(O)R^{10}$, $-X^6S(O)_2R^{10}$ and $-X^6C(O)R^{10}$;

$R^6$ is $(C_{6-12})$aryl, hetero$(C_{5-13})$aryl and halo substituted $(C_{1-6})$ alkyl; wherein $R^6$ is optionally is substituted by 1 to 5 radicals independently selected from a group consisting of $(C_{1-9})$alkyl, $(C_{3-12})$cycloalkyl$(C_{0-6})$alkyl, hetero$(C_{5-12})$cycloalkyl$(C_{0-6})$alkyl, $(C_{6-12})$aryl$(C_{0-6})$alkyl, hetero$(C_{5-13})$aryl$(C_{0-6})$alkyl, cyano, halo, halo-substituted $(C_{1-6})$alkyl, $-X^6NR^9R^9$, $-X^6OR^9$, $-X^6SR^9$, $-X^6C(O)NR^9R^9$, $-X^6OC(O)NR^9R^9$, $-X^6C(O)OR^9$, $-X^6NC(O)OR^9$, $-X^6S(O)R^{10}$, $-X^6S(O)_2R^{10}$ and $-X^6C(O)R^{10}$;

$R^7$ is H, $(C_{1-6})$alkyl, $(C_{3-12})$cycloalkyl$(C_{0-6})$alkyl, hetero$(C_{3-12})$cycloalkyl$(C_{0-6})$alkyl, $(C_{6-12})$aryl$(C_{0-6})$alkyl, hetero$(C_{5-12})$aryl$(C_{0-6})$alkyl, and halo substituted $(C_{1-6})$ alkyl; wherein $R^7$ is optionally is substituted by 1 to 5 radicals independently selected from a group consisting of $(C_{1-4})$alkyl, cyano, halo, halo-substituted $(C_{1-4})$alkyl, $-X^6NR^9R^9$, $-X^6OR^9$, $-X^6SR^9$, $-X^6C(O)NR^9R^9$, $-X^6OC(O)NR^9R^9$, $-X^6C(O)OR^9$, $-X^6NC(O)OR^9$, $-X^6S(O)R^{10}$, $-X^6S(O)_2R^{10}$ and $-X^6C(O)R^{10}$;

$R^8$ is selected from the group consisting of H, $(C_{1-6})$alkyl, $(C_{3-12})$cycloalkyl$(C_{0-6})$alkyl, hetero$(C_{3-12})$cycloalkyl$(C_{0-6})$alkyl, $(C_{6-12})$aryl$(C_{0-6})$alkyl, and hetero$(C_{5-13})$aryl$(C_{0-6})$alkyl, or $R^7$ and $R^8$ together with the atom attached to form $(C_{3-8})$cycloalkylene or $(C_{3-8})$heterocycloalkylene;

$R^9$ at each occurrence independently is hydrogen, $(C_{1-6})$alkyl or halo-substituted $(C_{1-6})$alkyl;

$R^{10}$ is $(C_{1-6})$alkyl or halo-substituted $(C_{1-6})$alkyl;

$R^{11}$ is selected from the group consisting of hydrogen, $(C_{1-9})$alkyl, $(C_{3-12})$cycloalkyl$(C_{0-6})$alkyl, hetero$(C_{5-12})$cycloalkyl$(C_{0-6})$alkyl, $(C_{6-12})$aryl$(C_{0-6})$alkyl, hetero$(C_{5-13})$aryl$(C_{0-6})$alkyl, $(C_{9-12})$bicycloaryl$(C_{0-3})$alkyl, hetero$(C_{8-12})$-bicycloaryl$(C_{0-3})$alkyl, $-C(O)R^{13}$, $-C(S)R^{13}$, $-S(O)_2R^{13}$, $-C(O)OR^{13}$, $-C(O)N(R^7)R^8$, $-C(S)N(R^7)R^8$ and $-S(O)_2N(R^7)R^8$;

$R^{12}$ is H or $C_{1-6}$alkyl optionally substituted by amido, $(C_{6-12})$aryl, hetero$(C_{5-12})$aryl, hetero$(C_{5-12})$cycloalkyl or hydroxy;

$R^{13}$ is $(C_{1-6})$alkyl, $(C_{3-12})$cycloalkyl$(C_{0-6})$alkyl, hetero$(C_{3-12})$cycloalkyl$(C_{0-6})$alkyl, $(C_{6-12})$aryl$(C_{0-6})$alkyl, hetero$(C_{5-13})$aryl$(C_{0-6})$alkyl, and halo substituted $(C_{1-6})$ alkyl; wherein $R^{13}$ is optionally is substituted by 1 to 5 radicals independently selected from a group consisting of $(C_{1-4})$alkyl, cyano, halo, halo-substituted $(C_{1-4})$alkyl, $-X^6NR^9R^9$, $-X^6OR^9$, $-X^6SR^9$, $-X^6C(O)NR^9R^9$, $-X^6OC(O)NR^9R^9$, $-X^6C(O)OR^9$, $-X^6NC(O)OR^9$, $-X^6S(O)R^{10}$, $-X^6S(O)_2R^{10}$ and $-X^6C(O)R^{10}$; and n is zero or an integer 1 or 2;

and their corresponding N-oxides, and their prodrugs, and their protected derivatives, individual isomers and mixtures of isomers thereof; and the pharmaceutically acceptable salts and solvates (e.g. hydrates) of such compounds of Formula (Ia) and their N-oxides and their prodrugs, and their protected derivatives, individual isomers and mixtures of isomers thereof.

In another aspect of the present invention, the inventive subject matter is the backbone structures of Formulae II, III, IV or V, wherein $sub_1$-$sub_8$ are general substituents. The specific substituents at $sub_1$-$sub_8$ are not part of this aspect of the invention and can be any chemical groups or radicals which may be substituted at those positions (referred to as "general substituents" hereinafter), including those substitutions made possible by any conventional means or by any new technologies developed in the future. Thus, for the purpose of this application, "general substituents" do not serve as a claim element or limitation of the claim and they themselves may be novel and non-obvious, or unknown at the time of the invention.

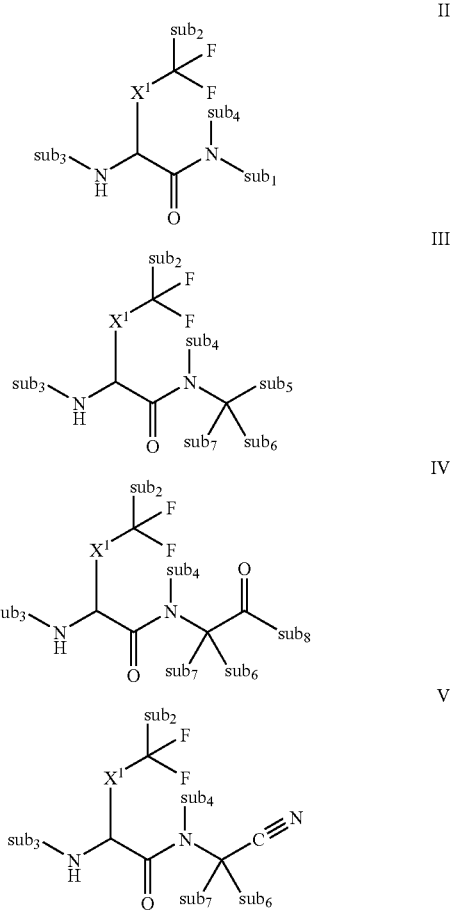

In yet another aspect of the invention, the inventive subject matter includes the backbone structure of Formulae II, III, IV or V together with popular substituents at $sub_1$-$sub_8$. For the purpose of this application, "a popular substituent" means a chemical group or radical which, at the time of the present invention, people of ordinary skill in the art, by using the specific substitutions disclosed hereinafter as guidance, would deem practical to substitute at $sub_1$-$sub_8$ without undue experimentation in practicing the present invention.

In still another aspect of the invention, the inventive subject matter includes the backbone structures of Formulae II, III, IV or V and specific substituents disclosed hereinafter at $sub_1$-$sub_8$. The specific substituent disclosed in the present application is refereed to as a "particular substituent." For the purpose of the present application, a particular substituent, if recited in the claims, serves as a claim limitation and may confer patentability on the claim by itself or in combination with the backbone structure along with other substituents therein.

Definitions

Unless otherwise stated, the following terms used in the specification and claims are defined for the purposes of this Application and have the following meanings.

"A related chemical entity" of a compound, means an N-oxide derivative, a prodrug derivative, a protected derivative, an individual isomer, a mixture of isomers, or a pharmaceutically acceptable salt or solvate, of said compound, which can be prepared without undue experimentation by people with ordinary skill in the field.

"Acyl" means an H—CO— or alkyl-CO— group in which the alkyl group is as described herein.

"Acylamino" is an acyl-NH— group wherein acyl is as defined herein.

"Alkoxy" means an alkyl-O— group in which the alkyl group is as described herein. Exemplary alkoxy groups include allyloxy, difluoromethoxy, methoxy, trifluoromethoxy, ethoxy, n-propoxy, i-propoxy, n-butoxy and heptoxy.

"Alkoxycarbonyl" means an alkyl-O—CO— group in which the alkyl group is as described herein. Exemplary alkoxycarbonyl groups include methoxy- and ethoxycarbonyl.

"Alkyl" represented by itself means a straight or branched, saturated or unsaturated, aliphatic radical having the number of carbon atoms indicated (e.g., $(C_{1-6})$alkyl includes methyl, ethyl, propyl, isopropyl, butyl, sec-butyl, isobutyl, tert-butyl, vinyl, allyl, 1-propenyl, isopropenyl, 1-butenyl, 2-butenyl, 3-butenyl, 2-methylallyl, ethynyl, 1-propynyl, 2-propynyl, and the like). Alkyl represented along with another radical (e.g., as in arylalkyl) means a straight or branched, saturated or unsaturated aliphatic divalent radical having the number of atoms indicated or when no atoms are indicated means a bond (e.g., $(C_{6-12})$aryl$(C_{0-6})$alkyl includes phenyl, benzyl, phenethyl, 1-phenylethyl 3-phenylpropyl, and the like). It will be appreciated by those skilled in the art that when alkyl represents an unsaturated aliphatic radical such radicals may not be attached directly to an oxygen, nitrogen or sulphur atom via the carbon carbon multiple bond of said unsaturated aliphatic radical.

"Alkylene", unless indicated otherwise, means a straight or branched, saturated or unsaturated, aliphatic, divalent radical having the number of carbon atoms indicated, $(C_{1-2})$alkylene includes methylene (—$CH_2$—) and ethylene (—$CH_2CH_2$—). It will be appreciated by those skilled in the art that when alkylene represents an unsaturated, aliphatic, divalent radical such radicals may not be attached directly to an oxygen, nitrogen or sulphur atom via the carbon carbon multiple bond of said unsaturated, aliphatic, divalent radical.

"Alkylenedioxy" means an —O-alkylene-O— group in which alkylene is as defined above. Exemplary alkylenedioxy groups include methylenedioxy and ethylenedioxy.

"Alkylsulfinyl" means an alkyl-SO— group in which the alkyl group is as previously described. Preferred alkylsulfinyl groups are those in which the alkyl group is $C_{1-4}$alkyl.

"Alkylsulfonyl" means an alkyl-$SO_2$— group in which the alkyl group is as previously described. Preferred alkylsulfonyl groups are those in which the alkyl group is $C_{1-4}$alkyl.

"Alkylthio" means an alkyl-S— group in which the alkyl group is as previously described. Exemplary alkylthio groups include methylthio, ethylthio, isopropylthio and heptylthio.

"Aromatic" means a moiety wherein the constituent atoms make up an unsaturated ring system, all atoms in the ring system are $sp^2$ hybridized and the total number of pi electrons is equal to 4n+2.

"Aroyl" means an aryl-CO— group in which the aryl group is as described herein. Exemplary aroyl groups include benzoyl and 1- and 2-naphthoyl.

"Aroylamino" is an aroyl-NH— group wherein aroyl is as previously defined.

"Aryl" as a group or part of a group denotes: (i) an optionally substituted monocyclic or multicyclic aromatic carbocyclic moiety of 6 to 12 carbon atoms, such as phenyl or naphthyl; or (ii) an optionally substituted partially saturated multicyclic aromatic carbocyclic moiety in which an aryl and a cycloalkyl or cycloalkenyl group are fused together to form a cyclic structure, such as a tetrahydronaphthyl, indenyl or indanyl ring. Except where otherwise defined, aryl groups may be substituted with one or more aryl group substituents, which may be the same or different, where "aryl group substituent" includes, for example, acyl, acylamino, alkoxy, alkoxycarbonyl, alkylenedioxy, alkylsulfinyl, alkylsulfonyl, alkylthio, aroyl, aroylamino, aryl, arylalkyloxy, arylalkyloxycarbonyl, arylalkylthio, aryloxy, aryloxycarbonyl, arylsulfinyl, arylsulfonyl, arylthio, carboxy (or an acid bioisostere), cyano, cycloalkyl, halo, heteroaroyl, heteroaryl, heteroarylalkyloxy, heteroaroylamino, heteroaryloxy, heterocycloalkyl, hydroxy, nitro, trifluoromethyl, —$NY^3Y^4$, —$CONY^3Y^4$, —$SO_2NY^3Y^4$, —$NY^3$—C(=O)alkyl, —$NY^3SO_2$alkyl or alkyl optionally substituted with aryl, heteroaryl, hydroxy, or —$NY^3Y^4$ (in which $Y^3$ and $Y^4$ are independently hydrogen, alkyl, aryl, arylalkyl, cycloalkyl, heteroaryl or heteroarylalkyl; or the group —$NY^3Y^4$ may form a cyclic amine). Exemplary optionally substituted $(C_{6-12})$aryl include, but is not limited to, biphenyl, bromophenyl, chlorophenyl, dichlorophenyl, difluoromethoxyphenyl, dimethylphenyl, ethoxycarbonylphenyl, fluorophenyl, isopropylphenyl, methoxyphenyl, methylphenyl, methylsulfonylphenyl, naphthyl, pentafluorophenyl, phenyl, trifluoromethoxyphenyl, trifluoromethylphenyl, and the like. Optionally substituted $(C_{6-12})$aryl as used in this Application to define a radical substituent attached to the group $R^6$ includes trifluoromethoxyphenyl, difluoromethoxyphenyl, 4-fluorophenyl, and the like.

"Arylalkyloxy" means an arylalkyl-O— group in which the arylalkyl groups is as previously described. Exemplary arylalkyloxy groups include benzyloxy and 1- or 2-naphthalenemethoxy.

"Arylalkyloxycarbonyl" means an arylalkyl-O-CO— group in which the arylalkyl groups is as previously described. An exemplary arylalkyloxycarbonyl group is benzyloxycarbonyl.

"Arylalkylthio" means an arylalkyl-S— group in which the arylalkyl group is as previously described. An exemplary arylalkylthio group is benzylthio.

"Aryloxy" means an aryl-O— group in which the aryl group is as previously described. Exemplary aryloxy groups include phenoxy and naphthoxy, each optionally substituted.

"Aryloxycarbonyl" means an aryl-O—C(=O)— group in which the aryl group is as previously described. Exemplary aryloxycarbonyl groups include phenoxycarbonyl and naphthoxycarbonyl.

"Arylsulfinyl" means an aryl-SO— group in which the aryl group is as previously described.

"Arylsulfonyl" means an aryl-$SO_2$— group in which the aryl group is as previously described.

"Arylthio" means an aryl-S— group in which the aryl group is as previously described. Exemplary arylthio groups include phenylthio and naphthylthio.

"Cycloalkyl" means a saturated or partially unsaturated, monocyclic, fused bicyclic or bridged polycyclic ring assembly containing the number of ring carbon atoms indicated, and any carbocyclic ketone, thioketone or iminoketone derivative thereof (e.g., $(C_{3-12})$cycloalkyl includes cyclopropyl, cyclobutyl, cyclopentyl, cyclohexyl, cyclohexenyl, 2,5-cyclohexadienyl, bicyclo[2.2.2]octyl, adamantan-1-yl, decahydronaphthyl, oxocyclohexyl, dioxocyclohexyl, thiocyclohexyl, 2-oxobicyclo[2.2.1]hept-1-yl, and the like). It will be appreciated by those skilled in the art that when cycloalkyl represents an unsaturated cyclic ring assembly such rings may not be attached directly via the carbon carbon multiple bond to an oxygen, nitrogen or sulphur atom.

"Cycloalkylene" means a divalent saturated or partially unsaturated, monocyclic ring or bridged polycyclic ring assembly containing the number of ring carbon atoms indicated, and any carbocyclic ketone, thioketone or iminoketone derivative thereof.

"Heteroaroyl" means a heteroaryl-C(=O)— group in which the heteroaryl group is as described herein. Exemplary heteroaryl groups include pyridylcarbonyl.

"Heteroaroylamino" means a heteroaroyl-NH— group in which the heteroaryl moiety is as previously described.

"Heteroaryl" as a group or part of a group denotes: (i) an optionally substituted aromatic monocyclic or multicyclic organic moiety of about 5 to about 13 ring members in which one or more of the ring members is/are element(s) other than carbon, for example nitrogen, oxygen or sulfur (examples of such groups include benzimidazolyl, benzoxazolyl, benzothiazolyl, furyl, imidazolyl, indolyl, indolizinyl, isoxazolyl, isoquinolinyl, isothiazolyl, oxadiazolyl, oxazolyl, pyrazinyl, pyridazinyl, pyrazolyl, pyridyl, pyrimidinyl, pyrrolyl, quinazolinyl, quinolinyl, 1,3,4-thiadiazolyl, thiazolyl, thienyl and triazolyl groups, optionally substituted by one or more aryl group substituents as defined above except where otherwise defined); (ii) an optionally substituted partially saturated multicyclic heterocarbocyclic moiety in which a heteroaryl and a cycloalkyl or cycloalkenyl group are fused together to form a cyclic structure (examples of such groups include pyrindanyl groups, optionally substituted by one or more "aryl group substituents" as defined above, except where otherwise defined). Optional substituents include one or more "aryl group substituents" as defined above, except where otherwise defined. Optionally substituted hetero($C_{5-13}$)aryl as used in this Application to define $R^6$ includes benzoxazol-2-yl, 5-tert-butyl-[1,2,4]oxadiazol-3-yl, 3-cyclopropyl-1,2,4-oxadiazol-5-yl, 5-cyclopropyl-1,2,4-oxadiazol-5-yl, 5-cyclopropyl-1,3,4-oxadiazol-2-yl, 5-ethyl-[1,3,4]oxadiazol-2-yl, 5-(4-fluoro-phenyl)-1,2,4-oxadiazol-3-yl, 5-isopropyl-isoxazol-3-yl, 5-(5-methyl-isoxazol-3-yl)-oxazol-2-yl, oxazol-2-yl, 3-phenyl-1,2,4-oxadiazol-5-yl, 5-phenyl-1,2,4-oxadiazol-5-yl, 5-phenyl-1,2,4-oxadiazol-3-yl, 3-(tetrahydro-pyran-4-yl)-1,2,4-oxadiazol-5-yl,5-thiophen-2-yl-oxazol-2-yl, 5-(4-trifluoromethoxy-phenyl)-1,3,4-oxadiazol-2-yl, and the like.

"Heteroarylalkyloxy" means an heteroarylalkyl-O— group in which the heteroarylalkyl group is as previously described. Exemplary heteroaryloxy groups include optionally substituted pyridylmethoxy.

"Heteroaryloxy" means an heteroaryl-O— group in which the heteroaryl group is as previously described. Exemplary heteroaryloxy groups include optionally substituted pyridyloxy.

"Heterocycloalkyl" means cycloalkyl, as defined in this Application, provided that one or more of the ring carbon atoms indicated are replaced by a heteroatom moiety selected from —N=, —NR—, —O— or —S—, wherein R is hydrogen, $(C_{1-6})$alkyl, a protecting group or represents the free valence which serves as the point of attachment to a ring nitrogen, and any carbocyclic ketone, thioketone or iminoketone derivative thereof (e.g., the term hetero($C_{5-12}$)cycloalkyl includes imidazolidinyl, morpholinyl, piperazinyl, piperidyl, pyrrolidinyl, pyrrolinyl, quinuclidinyl, and the like). Suitable protecting groups include tert-butoxycarbonyl, benzyloxycarbonyl, benzyl, 4-methoxybenzyl, 2-nitrobenzyl, and the like. Both the unprotected and protected derivatives fall within the scope of the invention.

"Heterocycloalkylene" means cycloalkylene, as defined in this Application, provided that one or more of the ring member carbon atoms indicated, is replaced by heteroatom moiety selected from —N=, —NR—, —O—, —S— or —$S(O)_2$—, wherein R is hydrogen, $(C_{1-6})$alkyl or a protecting group.

"Isomers", as used in this disclosure, mean the compounds of the present invention having identical molecular formulae but differing in the nature or sequence of bonding of their atoms or in the arrangement of their atoms in space. Isomers that differ in the arrangement of their atoms in space are termed "stereoisomers". Stereoisomers that are not mirror images of one another are termed "diastereomers" and stereoisomers that are nonsuperimposable mirror images are termed "enantiomers" or sometimes "optical isomers". A carbon atom bonded to four nonidentical substituents is termed a "chiral center". A compound, which has one chiral center has two enantiomeric forms of opposite chirality. A "racemic mixture" contains both enantiomers as a 1:1 ratio. However, in terms of this application a racemic mixture has been employed when both enantiomers were present irrespective of their ratios. A compound that has more than one chiral center has $2^{n-1}$ enantiomeric pairs, where n is the number of chiral centers. Compounds with more than one chiral center may exist as either an individual diastereomer or as a mixture of diastereomers, termed a "diastereomeric mixture". When one chiral center is present a stereoisomer may be characterized by the absolute configuration of that chiral center. Absolute configuration refers to the arrangement in space of the substituents attached to the chiral center. Enantiomers are characterized by the absolute configuration of their chiral centers and described by the R- and S-sequencing rules of Cahn, Ingold and Prelog. Conventions for stereochemical nomenclature, methods for the determination of stereochemistry and the separation of stereoisomers are well known in the art (e.g., see "Advanced Organic Chemistry", 4th edition, March, Jerry, John Wiley & Sons, New York, 1992). It is understood that the names and illustrations used in this disclosure to describe compounds of the present invention are meant to encompass all possible stereoisomers. Thus, for example, [the name morpholine-4-carboxylic acid {1-[1-(3-cyclopropyl-[1,2,4]oxadiazole-5-carbonyl)-propylcarbamoyl]-3,3-difluoro-hexyl}-amide is meant to include morpholine-4-carboxylic acid {(S)-1-[(S)-1-(3-cyclopropyl-1,2,4-oxadiazole-5-carbonyl)-propylcarbamoyl]-3,3-difluoro-hexyl}-amide and morpholine-4-carboxylic acid {(R)-1-[(R)-1-(3-cyclopropyl-1,2,4-oxadiazole-5-carbonyl)-propylcarbamoyl]-3,3-difluoro-hexyl}-amide and any mixture, racemic or otherwise, thereof.]

"N-oxide derivatives" means derivatives of compounds of the present invention in which nitrogens are in an oxidized state (i.e., N—O) and which possess the desired pharmacological activity.

"Pharmaceutically acceptable" means that which is useful in preparing a pharmaceutical composition that is generally safe, non-toxic and neither biologically nor otherwise undesirable and includes that which is acceptable for veterinary use as well as human pharmaceutical use.

"Pharmaceutically acceptable salts" means salts of compounds of present invention which are pharmaceutically acceptable, as defined above, and which possess the desired pharmacological activity. Such salts include acid addition salts formed with inorganic acids such as hydrochloric acid, hydrobromic acid, sulfuric acid, nitric acid, phosphoric acid, and the like; or with organic acids such as acetic acid, propionic acid, hexanoic acid, heptanoic acid, cyclopentane propionic acid, glycolic acid, pyruvic acid, lactic acid, malonic acid, succinic acid, malic acid, maleic acid, fumaric acid, tartaric acid, citric acid, benzoic acid, o-(4-hydroxybenzoyl) benzoic acid, cinnamic acid, mandelic acid, methylsulfonic acid, ethanesulfonic acid, 1,2-ethanedisulfonic acid, 2-hydroxyethanesulfonic acid, benzenesulfonic acid, p-chlorobenzenesulfonic acid, 2-naphthalenesulfonic acid, p-toluenesulfonic acid, camphorsulfonic acid, 4-methylbicyclo [2.2.2]oct-2-ene-1-carboxylic acid, glucoheptonic acid, 4,4'-methylenebis(3-hydroxy-2-ene-1-carboxylic acid), 3-phenylpropionic acid, trimethylacetic acid, tertiary butylacetic acid, lauryl sulfuric acid, gluconic acid, glutamic acid, hydroxynaphthoic acid, salicylic acid, stearic acid, muconic acid and the like.

Pharmaceutically acceptable salts also include base addition salts which may be formed when acidic protons present are capable of reacting with inorganic or organic bases. Acceptable inorganic bases include sodium hydroxide, sodium carbonate, potassium hydroxide, aluminum hydroxide and calcium hydroxide. Acceptable organic bases include ethanolamine, diethanolamine, triethanolamine, tromethamine, N-methylglucamine and the like.

"Prodrug" means a compound, which is convertible in vivo by metabolic means to a compound of present invention. For example an ester of a compound of present invention containing a hydroxy group may be convertible by hydrolysis in vivo to the parent molecule. Alternatively an ester of a compound of present invention containing a carboxy group may be convertible by hydrolysis in vivo to the parent molecule. Suitable esters of compounds of present invention containing a hydroxy group, are for example acetates, citrates, lactates, tartrates, malonates, oxalates, salicylates, propionates, succinates, fumarates, maleates, methylene-bis-b-hydroxynaphthoates, gentisates, isethionates, di-p-toluoyltartrates, methylsulfonates, ethanesulfonates, benzenesulfonates, p-toluenesulfonates, cyclohexylsulfamates and quinates. Suitable esters of compounds of present invention containing a carboxy group are, for example, those described by F. J. Leinweber, Drug Metab. Res., 1987, 18, page 379. An especially useful class of esters of compounds of present invention containing a hydroxy group, may be formed from acid moieties selected from those described by Bundgaard et al., J. Med. Chem., 1989, 32, page 2503-2507, and include substituted (aminomethyl)-benzoates, for example, dialkylaminomethylbenzoates in which the two alkyl groups may be joined together and/or interrupted by an oxygen atom or by an optionally substituted nitrogen atom, e.g., an alkylated nitrogen atom, more especially (morpholino-methyl)benzoates, e.g., 3- or 4-(morpholinomethyl)-benzoates, and (4-alkylpiperazin-1-yl)benzoates, e.g., 3- or 4-(4-alkylpiperazin-1-yl) benzoates.

"Protected derivatives" means derivatives of compounds of present invention in which a reactive site or sites are blocked with protecting groups. Protected derivatives of compounds of present invention are useful in the preparation of compounds of present invention or in themselves may be active cathepsin S inhibitors. A comprehensive list of suitable protecting groups can be found in T. W. Greene, *Protecting Groups in Organic Synthesis*, 3rd edition, John Wiley & Sons, Inc., 1999.

"Therapeutically effective amount" means that amount which, when administered to an animal for treating a disease, is sufficient to effect such treatment for the disease.

"Treatment" or "treating" means any administration of a compound of the present invention and includes:
(1) preventing the disease from occurring in an animal which may be predisposed to the disease but does not yet experience or display the pathology or symptomatology of the disease,
(2) inhibiting the disease in an animal that is experiencing or displaying the pathology or symptomatology of the diseased (i.e., arresting further development of the pathology and/or symptomatology), or
(3) ameliorating the disease in an animal that is experiencing or displaying the pathology or symptomatology of the diseased (i.e., reversing the pathology and/or symptomatology).

Nomenclature:

The compounds of present invention and the intermediates and starting materials used in their preparation are named in accordance with IUPAC rules of nomenclature in which the characteristic groups have decreasing priority for citation as the principle group as follows: acids, esters, amides, etc. Alternatively, the compounds are named by AutoNom 4.0 (Beilstein Information Systems, Inc.). [For example, a compound of formula (I) wherein $R^1$ is morpholine-4-carbonyl, $X^1$ is methylene, $R^5$ is methyl, $R^2$ is H and A is

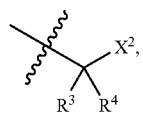

in which $R^3$ is ethyl, $R^4$ is H and $X^2$ is $C(O)R^6$ where $R^6$ is 3-cyclopropyl-1,2,4-oxadiazol-5-yl; that is, a compound having the following structure:

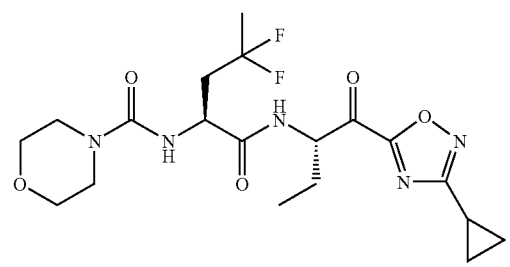

is named morpholine-4-carboxylic acid {(S)-1-[(S)-1-(3-cyclopropyl-1,2,4-oxadiazole-5-carbonyl)-propylcarbamoyl]-3,3-difluoro-butyl}-amide However, it is understood that, for a particular compound referred to by both a structural formula and a nomenclature name, if the structural formula and the nomenclature name are inconsistent with each other, the structural formula takes the precedence over the nomenclature name.

The various features of novelty which characterize the invention are pointed out with particularity in the claims annexed to and forming a part of this disclosure. For a better understanding of the invention, its operating advantages, and specific objects attained by its use, reference should be made to the following description in which there are illustrated and described preferred embodiments of the invention.

DETAILED DESCRIPTION OF PARTICULAR EMBODIMENTS

With reference to formula (I) above, the following are particular groupings:

$X^1$ may particularly represent methylene.

A may particularly represent

[structure with $X^2$, $R^3$, $R^4$]

wherein: $R^3$ is H, $(C_{6-12})$aryl$(C_{2-6})$alkyl or $(C_{1-6})$alkyl optionally substituted by —$X^6OR^9$ [in which $X^6$ is a bond and $R^9$ is $(C_{1-6})$alkyl]; $R^4$ is H or $(C_{1-6})$alkyl; and $X^2$ is CHO, CN or C(O)$R^6$ [in which $R^6$ is hetero$(C_{5-13})$aryl optionally substituted by $(C_{1-9})$alkyl, $(C_{3-12})$cycloalkyl, $(C_{6-12})$aryl or hetero$(C_{5-13})$aryl].

A may also particularly represent

[structure with $X^5$—N—$R^{11}$]

wherein $X^5$ is propylene and $R^{11}$ is —C(O)O$R^{13}$ or —S(O)$_2$$R^{13}$, in which $R^{13}$ is alkyl or $(C_{6-12})$aryl.

$R^1$ may particularly represent $R^{13}$C(O)— in which $R^{13}$ is hetero$(C_{5-12})$cycloalkyl.

$R^1$ may also particularly represent $R^{13}$OC(O)— in which $R^{13}$ is $(C_{6-12})$aryl$(C_{1-6})$alkyl.

$R^1$ may also particularly represent $(C_{1-9})$alkyl.

$R^1$ may also particularly represent hetero$(C_{5-12})$cycloalkyl.

$R^2$ may particularly represent H.

$R^5$ may particularly represent $(C_{1-9})$alkyl.

$R^5$ may also particularly represent $(C_{6-12})$aryl$(C_{1-6})$alkyl.

Particular Genera:

A particular group of compounds of the invention are compounds of Formula (Ia):

[structure (Ia)]

wherein $R^1$, $R^3$, $R^4$ and $R^5$ are as hereinbefore described, and their corresponding N-oxides, and their prodrugs, and their protected derivatives, individual isomers and mixtures of isomers thereof; and the pharmaceutically acceptable salts and solvates (e.g. hydrates) of such compounds of Formula (Ia) and their N-oxides and their prodrugs, and their protected derivatives, individual isomers and mixtures of isomers thereof.

Compounds of Formula (Ia) in which $R^1$ is $R^{13}$C(O)— and $R^{13}$ is hetero$(C_{5-12})$cycloalkyl are examples. Compounds of Formula (Ia) in which $R^1$ is

[morpholine-N—C(O)— structure]

are particular examples.

Compounds of Formula (Ia) in which $R^3$ is H, $(C_{6-12})$aryl$(C_{1-6})$alkyl or $(C_{1-6})$alkyl are examples.

Compounds of Formula (Ia) in which $R^3$ is H,

[phenyl-CH$_2$—CH$_2$—  or  CH$_3$—CH$_2$—CH$_2$—]

are particular examples.

Compounds of Formula (Ia) in which $R^4$ is H or methyl are examples.

Compounds of Formula (Ia) in which $R^5$ is $(C_{6-12})$aryl$(C_{1-6})$alkyl are examples.

Compounds of Formula (Ia) in which $R^5$ represents

[phenyl-CH$_2$—]

are particular examples.

A particular group of compounds of the invention are compounds of formula (Ia) in which: $R^1$ is $R^{13}$C(O)— (especially

[morpholine-N—C(O)—]);

$R^3$ is H, $(C_{6-12})$aryl$(C_{1-6})$alkyl (especially

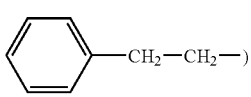

or $(C_{1-6})$alkyl (especially $CH_3$—$CH_2$—$CH_2$—); $R^4$ is H or methyl and $R^5$ is $(C_{6-12})$aryl$(C_{1-6})$alkyl (especially

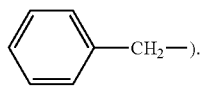

A further particular group of compounds of the invention are compounds of Formula (Ib):

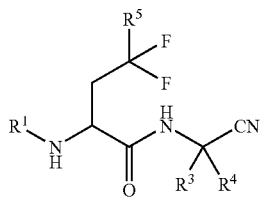

(Ib)

wherein $R^1$, $R^3$, $R^4$ and $R^5$ are as hereinbefore described, and their corresponding N-oxides, and their prodrugs, and their protected derivatives, individual isomers and mixtures of isomers thereof; and the pharmaceutically acceptable salts and solvates (e.g. hydrates) of such compounds of Formula (Ib) and their N-oxides and their prodrugs, and their protected derivatives, individual isomers and mixtures of isomers thereof.

Compounds of Formula (Ib) in which $R^1$ is $R^{13}C(O)$— and $R^{13}$ is hetero$(C_{5-12})$cycloalkyl are examples. Compounds of Formula (Ib) in which $R^1$ is

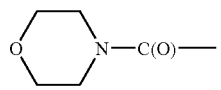

are particular examples.

Compounds of Formula (Ib) in which $R^3$ is H, $(C_{6-12})$aryl$(C_{1-6})$alkyl or $(C_{1-6})$alkyl are examples. Compounds of Formula (Ib) in which $R^3$ is H,

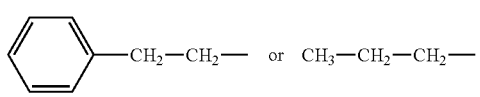

are particular examples.

Compounds of Formula (Ib) in which $R^4$ is H or methyl are examples. Compounds of Formula (Ib) in which $R^5$ is $(C_{6-12})$aryl$(C_{1-6})$alkyl are examples. Compounds of Formula (Ib) in which $R^5$ represents

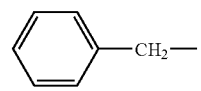

are particular examples.

A particular group of compounds of the invention are compounds of formula (Ib) in which: $R^1$ is $R^{13}C(O)$— (especially

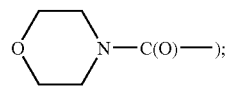

$R^3$ is H, $(C_{6-12})$aryl$(C_{1-6})$alkyl (especially

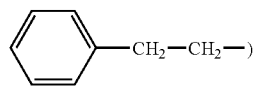

or $(C_{1-6})$alkyl (especially $CH_3$—$CH_2$—); $R^4$ is H or methyl and $R^5$ is $(C_{6-12})$aryl$(C_{1-6})$alkyl (especially

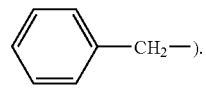

A further particular group of compounds of the invention are compounds of Formula (Ic):

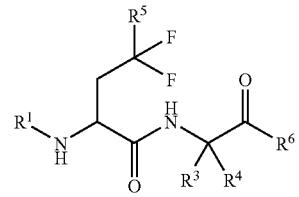

(Ic)

wherein $R^1$, $R^3$, $R^4$, $R^5$ and $R^6$ are as hereinbefore described, and their corresponding N-oxides, and their prodrugs, and their protected derivatives, individual isomers and mixtures of isomers thereof; and the pharmaceutically acceptable salts and solvates (e.g. hydrates) of such compounds of Formula (Ic) and their N-oxides and their prodrugs, and their protected derivatives, individual isomers and mixtures of isomers thereof.

Compounds of Formula (Ic) in which $R^1$ is $R^{13}C(O)$— and $R^{13}$ is hetero$(C_{5-12})$cycloalkyl are examples. Compounds of Formula (Ic) in which $R^1$ is

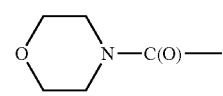

are particular examples.

Compounds of Formula (Ic) in which $R^3$ is $(C_{1-6})$alkyl optionally substituted by —$X^6OR^9$ [in which $X^6$ is a bond and $R^9$ is $(C_{1-6})$alkyl] are examples. Compounds of Formula (Ic) in which $R^3$ is $CH_3$—$CH_2$—, $CH_3$—$CH_2$—$CH_2$— or $CH_3$—O—$CH_2$— are particular examples.

Compounds of Formula (Ic) in which $R^4$ is H or methyl are examples. Compounds of Formula (Ic) in which $R^4$ is H are examples.

Compounds of Formula (Ic) in which $R^5$ is $(C_{1-9})$alkyl or $(C_{6-12})$aryl$(C_{1-6})$alkyl are examples. Compounds of Formula (Ic) in which $R^5$ represents $CH_3CH_2CH_2$ or $CH_3\,CH_2$ or $CH_3$ or

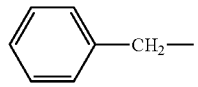

are particular examples. Compounds of Formula (Ic) in which $R^5$ represents

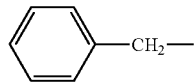

are particular examples.

Compounds of Formula (Ic) in which $R^6$ is hetero$(C_{5-13})$aryl, optionally substituted by $(C_{1-9})$alkyl, $(C_{3-12})$cycloalkyl, $(C_{6-12})$aryl or hetero$(C_{5-13})$aryl, are examples. Exemplary optionally substituted hetero$(C_{5-13})$aryl groups include optionally substituted benzoxazolyl, oxadiazolyl, isoxazolyl, or oxazolyl. Compounds of Formula (Ic) in which $R^6$ is benzoxazol-2-yl, 5-tert-butyl-[1,2,4]oxadiazol-3-yl, 3-cyclopropyl-1,2,4-oxadiazol-5-yl, 5-cyclopropyl-1,2,4-oxadiazol-2-yl, 5-cyclopropyl-1,3,4-oxadiazol-2-yl, 5-ethyl-1,3,4-oxadiazol-2-yl, 5-(4-fluoro-phenyl)-1,2,4-oxadiazol-3-yl, 5-isopropyl-isoxazol-3-yl, 5-(5-methyl-isoxazol-3-yl)-oxazol-2-yl, 5-(5-methyl-thien-2-yl)-oxazol-2-yl, oxazol-2-yl, 3-phenyl-1,2,4-oxadiazol-5-yl, 5-phenyl-1,2,4-oxadiazol-3-yl, 5-thiophen-2-yl-oxazol-2-yl, 5-(4-trifluoromethoxy-phenyl)-1,3,4-oxadiazol-2-yl and the like, are examples. Compounds of Formula (Ic) in which $R^6$ is benzoxazol-2-yl, 3-cyclopropyl-1,2,4-oxadiazol-5-yl, oxazol-2-yl, are particular examples.

A particular group of compounds of the invention are compounds of formula (Ic) in which: $R^1$ is $R^{13}C(O)$— (especially

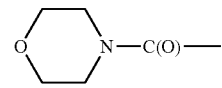

$R^3$ is $(C_{1-6})$alkyl optionally substituted by —$X^6OR^9$ (especially $CH_3$—$CH_2$—, $CH_3$—$CH_2$—$CH_2$— or $CH_3$—O—$CH_2$—); $R^4$ is H and $R^5$ is $(C_{1-9})$alkyl or $(C_{6-12})$aryl$(C_{1-6})$alkyl (especially

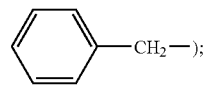

is hetero$(C_{5-13})$aryl, optionally substituted by $(C_{1-9})$alkyl, $(C_{3-12})$cycloalkyl, hetero$(C_{5-12})$ cycloalkyl, $(C_{6-12})$aryl or hetero$(C_{5-13})$aryl (especially benzoxazol-2-yl, 3-cyclopropyl-1,2,4-oxadiazol-5-yl, oxazol-2-yl and 5-methyl-isoxazol-3-yl)-oxazole-2-yl).

A further particular group of compounds of the invention are compounds of Formula (Id):

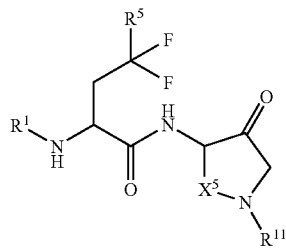

wherein $R^1$, $R^5$, $R^{11}$ and $X^5$ are as hereinbefore described, and their corresponding N-oxides, and their prodrugs, and their protected derivatives, individual isomers and mixtures of isomers thereof; and the pharmaceutically acceptable salts and solvates (e.g. hydrates) of such compounds of Formula (Id) and their N-oxides and their prodrugs, and their protected derivatives, individual isomers and mixtures of isomers thereof.

Compounds of Formula (Id) in which $R^1$ is $R^{13}C(O)$— and $R^{13}$ is hetero$(C_{5-12})$cycloalkyl are examples. Compounds of Formula (Id) in which $R^1$ is

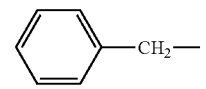

are particular examples.

Compounds of Formula (Id) in which $R^5$ is $(C_{6-12})$aryl $(C_{1-6})$alkyl are examples. Compounds of Formula (Id) in which $R^5$ represents

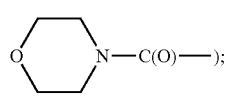

are particular examples.

Compounds of Formula (Id) in which $R^{11}$ is —$C(O)OR^{13}$ or —$S(O)_2R^{13}$, in which $R^{13}$ is alkyl or $(C_{6-12})$aryl are example. Compounds of Formula (Id) in which $R^{11}$ represents —$C(O)OC(CH_3)_3$ or

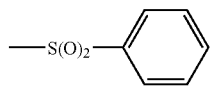

are particular examples.

Compounds of Formula (Id) in which $X^1$ is propylene are examples.

A particular group of compounds of the invention are compounds of formula (Id) in which: $R^1$ is $R^{13}C(O)$— (especially

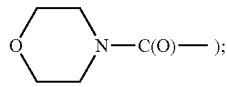

$R^5$ is $(C_{6-12})aryl(C_{1-6})alkyl$ (especially

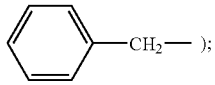

$R^{11}$ is —$C(O)OR^{13}$ [especially —$C(O)OC(CH_3)_3$] or —$S(O)_2R^{13}$ (especially

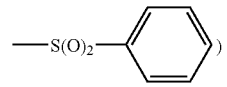

and $X^1$ is propylene are examples.

Particular compounds of the present invention include:

morpholine-4-carboxylic acid {(S)-1-[(S)-1-(3-cyclopropyl-1,2,4-oxadiazole-5-carbonyl)-propylcarbamoyl]-3,3-difluoro-hexyl}-amide;

morpholine-4-carboxylic acid {(S)-1-[(S)-1-(5-cyclopropyl-1,3,4-oxadiazole-2-carbonyl)-propylcarbamoyl]-3,3-difluoro-hexyl}-amide;

morpholine-4-carboxylic acid ((S)-3,3-difluoro-1-{(S)-1-[5-(4-trifluoromethoxy-phenyl)-1,3,4-oxadiazole-2-carbonyl]-propylcarbamoyl}-hexyl)-amide;

morpholine-4-carboxylic acid {(S)-1-[(S)-1-(3-cyclopropyl-1,2,4-oxadiazole-5-carbonyl)-propylcarbamoyl]-3,3-difluoro4-phenyl-butyl}-amide;

morpholine-4-carboxylic acid {1-[1-(3-cyclopropyl-[1,2,4]oxadiazole-5-carbonyl)-propylcarbamoyl]-3,3-difluoro-5-methyl-hexyl}-amide;

morpholine-4-carboxylic acid {(S)-1-[(S)-1-(3-cyclopropyl-1,2,4-oxadiazole-5-carbonyl)-propylcarbamoyl]-3,3-difluoro-butyl}-amide;

morpholine-4-carboxylic acid {(S)-3,3-difluoro-1-[(S)-1-(3-phenyl-1,2,4-oxadiazole-5-carbonyl)-propylcarbamoyl]-butyl}-amide;

morpholine-4-carboxylic acid {(S)-3,3-difluoro-1-[(S)-1-(5-phenyl-1,2,4-oxadiazole-3-carbonyl)-propylcarbamoyl]-butyl}-amide;

morpholine-4-carboxylic acid {1-[1-(5-cyclopropyl-[1,3,4]oxadiazole-2-carbonyl)-propylcarbamoyl]-3,3-difluoro-4-phenyl-butyl}-amide;

morpholine-4-carboxylic acid {3,3-difluoro-1-[1-(5-isopropyl-isoxazole-3-carbonyl)-propylcarbamoyl]-hexyl}-amide;

morpholine-4-carboxylic acid ((S)-3,3-difluoro-1-{1-[5-(5-methyl-isoxazol-3-yl)-oxazole-2-carbonyl]-propylcarbamoyl}-hexyl)-amide;

morpholine-4-carboxylic acid {(S)-3,3-difluoro-1-[(S)-1-(oxazole-2-carbonyl)-propylcarbamoyl]-4-phenyl-butyl}-amide;

morpholine-4-carboxylic acid {(S)-3,3-difluoro-4-phenyl-1-[(S)-1-(5-thiophen-2-yl-oxazole-2carbonyl)-propylcarbamoyl]-butyl}-amide;

morpholine-4-carboxylic acid {(S)-1-[(S)-1-(benzoxazole-2-carbonyl)-butylcarbamoyl]-3,3-difluoro4-phenyl-butyl}-amide;

morpholine-4-carboxylic acid [1-(2-benzooxazol-2-yl-1-methoxymethyl-2-oxo-ethylcarbamoyl)-3,3-difluoro-4-phenyl-butyl]-amide;

morpholine-4-carboxylic acid {(S)-1-[(S)-1-(benzoxazole-2-carbonyl)-1-methyl-butylcarbamoyl]-3,3-difluoro-4-phenyl-butyl}-amide;

morpholine-4-carboxylic acid [(S)-1-((S)-1-cyano-3-phenyl-propylcarbamoyl)-3,3-difluoro-4-phenyl-butyl]-amide;

morpholine-4-carboxylic acid [(S)-1-(cyanomethyl-carbamoyl)-3,3-difluoro-4-phenyl-butyl]-amide;

morpholine-4-carboxylic acid [(S)-3,3-difluoro-1-((S)-1-formyl-1-methyl-butylcarbamoyl)-4-phenyl-butyl]-amide;

morpholine-4-carboxylic acid {(S)-1-[1-(5-ethyl-[1,3,4]oxadiazole-2-carbonyl)-propylcarbamoyl]-3,3-difluoro-4-phenyl-butyl}-amide;

morpholine-4-carboxylic acid {(S)-1-[1-(5-tert-butyl-[1,2,4]oxadiazole-3-carbonyl)-propylcarbamoyl]-3,3-difluoro-4-phenyl-butyl}-amide;

morpholine-4-carboxylic acid {(S)-3,3-difluoro-4-phenyl-1-[(S)-1-(5-phenyl-[1,2,4]oxadiazol-3-yl)-propylcarbamoyl]-butyl}-amide;

[(S)-1-(cyanomethyl-carbamoyl)-3,3-difluoro-4-phenyl-butyl]-carbamic acid benzyl ester;

(S)-4,4-difluoro-5-phenyl-2-(tetrahydro-pyran-4-ylamino)-pentanoic acid cyanomethyl-amide;

(S)-4,4-difluoro-2-isobutylamino-5-phenyl-pentanoic acid cyanomethyl-amide;

morpholine-4-carboxylic acid [(S)-1-((S)-1-benzenesulfonyl-3-oxo-azepan-4-ylcarbamoyl)-3,3-difluoro-4-phenyl-butyl]-amide;

(S)-4-{(S)-4,4-difluoro-2-[(morpholine-4-carbonyl)-amino]-5-phenyl-pentanoylamino}-3-oxo-azepane-1-carboxylic acid tert-butyl ester;

morpholine-4-carboxylic acid ((S)-1-{(S)-1-[(5-ethyl-1,3,4-oxadiazol-2-yl)-hydroxy-methyl]-propylcarbamoyl}-3,3-difluoro-hexyl)-amide;

morpholine-4-carboxylic acid {(S)-1-[1-(5-cyclopropyl-1,3,4-oxadiazole-2-carbonyl)-propylcarbamoyl]-3,3-difluoro-butyl}-amide;

morpholine-4-carboxylic acid {(S)-1-[1-(5-cyclopropyl-1,2,4-oxadiazole-3-carbonyl)-propylcarbamoyl]-3,3-difluoro-hexyl}-amide;

morpholine-4-carboxylic acid ((S)-3,3-difluoro-1-{(S)-1-[5-(4-fluoro-phenyl)-1,2,4-oxadiazole-carbonyl]-propylcarbamoyl}-butyl)-amide;

morpholine-4-carboxylic acid ((S)-3,3-difluoro-1-{1-[5-(4-fluoro-phenyl)-1,2,4-oxadiazol-3-carbonyl]-propylcarbamoyl}-butyl)-amide;

morpholine-4-carboxylic acid ((S)-3,3-difluoro-1-{(R)-1-[5-(4-fluoro-phenyl)-1,2,4-oxadiazole-3-carbonyl]-propylcarbamoyl}-butyl)-amide;

morpholine-4-carboxylic acid {(S)-1-[(S)-1-(benzoxazole-2-carbonyl)-propylcarbamoyl]-3,3-difluoro-butyl}-amide;

morpholine-4-carboxylic acid [(S)-1-(cyanomethyl-carbamoyl)-3,3-difluoro-hexyl]-amide;

morpholine-4-carboxylic acid ((S)-3,3-difluoro-1-{(R)-1-[5-(5-methyl-thiophen-2-yl)-oxazole-2-carbonyl]-propylcarbamoyl}-hexyl)-amide;

morpholine-4-carboxylic acid ((S)-3,3-difluoro-1-{(S)-1-[5-(5-methyl-thiophen-2-yl)-oxazole-2-carbonyl]-propylcarbamoyl}-hexyl)-amide;

and their corresponding N-oxides, and their prodrugs, and their protected derivatives, individual isomers and mixtures of isomers thereof; and the pharmaceutically acceptable salts and solvates (e.g. hydrates) of such compounds of Formula (Ia) and their N-oxides and their prodrugs, and their protected derivatives, individual isomers and mixtures of isomers thereof.

Pharmacology and Utility:

The compounds of the invention are inhibitors of cathepsin S and, as such, are useful for treating diseases in which cathepsin S activity contributes to the pathology and/or symptomatology of the disease. For example, the compounds of the invention may be useful in treating autoimmune disorders, including, but not limited to, juvenile onset diabetes, multiple sclerosis, pemphigus vulgaris, Graves' disease, myasthenia gravis, systemic lupus erythemotasus, irritable bowel disease, rheumatoid arthritis and Hashimoto's thyroiditis, allergic disorders including but not limited to, asthma, and allogeneic immune responses, including, but not limited to, organ transplants or tissue grafts.

Cathepsin S is also implicated in disorders involving excessive elastolysis, such as chronic obstructive pulmonary disease (e.g., emphysema), bronchiolitis, excessive airway elastolysis in asthma and bronchitis, pneumonities and cardiovascular disease such as plaque rupture and atheroma. Cathepsin S is implicated in fibril formation and, therefore, inhibitors of cathepsin S may be of use in treatment of systemic amyloidosis.

The cysteine protease inhibitory activities of the compounds of the invention can be determined by methods known to those of ordinary skill in the art. Suitable in vitro assays for measuring protease activity and the inhibition thereof by test compounds are known. Typically, the assay measures protease-induced hydrolysis of a peptide-based substrate. Details of assays for measuring protease inhibitory activity are set forth in Examples 31, 32, 33, 34, infra.

The compounds of the invention are also inhibitors of cathepsin K and B and, as such, are useful for treating diseases in which cathepsin K and B activity contributes to the pathology and/or symptomatology of the disease. For example, the compounds of the invention may be useful in treating osteoarthritis, osteoporosis or cancer such as lung cancer, leukemia (B- and T-cell, acute), ovarian cancer, sarcomas, kaposi's sarkoma, bowel cancer, lymph node cancer, brain tumor, breast cancer, pancreas cancer, prostate cancer or skin cancer.

Administration and Pharmaceutical Compositions:

In general, compounds of the present invention will be administered in therapeutically effective amounts via any of the usual and acceptable modes known in the art, either singly or in combination with one or more therapeutic agents. A therapeutically effective amount may vary widely depending on the severity of the disease, the age and relative health of the subject, the potency of the compound used and other factors.

For example, therapeutically effective amounts of a compound of the invention may range from about 1 micrograms per kilogram body weight (μg/kg) per day to about 60 milligram per kilogram body weight (mg/kg) per day, typically from about 1 μg/kg/day to about 20 mg/kg/day. Therefore, a therapeutically effective amount for a 80 kg human patient may range from about 80 μg/day to about 4.8 g/day, typically from about 80 μg/day to about 1.6 g/day. In general, one of ordinary skill in the art, acting in reliance upon personal knowledge and the disclosure of this Application, will be able to ascertain a therapeutically effective amount of a compound of the invention for treating a given disease.

The compounds of the invention can be administered as pharmaceutical compositions by one of the following routes: oral, systemic (e.g., transdermal, intranasal or by suppository) or parenteral (e.g., intramuscular, intravenous or subcutaneous). Compositions can take the form of tablets, pills, capsules, semisolids, powders, sustained release formulations, solutions, suspensions, elixirs, aerosols, or any other appropriate composition and are comprised of, in general, a compound of the invention in combination with at least one pharmaceutically acceptable excipient. Acceptable excipients are non-toxic, aid administration, and do not adversely affect the therapeutic benefit of the active ingredient. Such excipient may be any solid, liquid, semisolid or, in the case of an aerosol composition, gaseous excipient that is generally available to one of skill in the art.

Solid pharmaceutical excipients include starch, cellulose, talc, glucose, lactose, sucrose, gelatin, malt, rice, flour, chalk, silica gel, magnesium stearate, sodium stearate, glycerol monostearate, sodium chloride, dried skim milk, and the like. Liquid and semisolid excipients may be selected from water, ethanol, glycerol, propylene glycol and various oils, including those of petroleum, animal, vegetable or synthetic origin (e.g., peanut oil, soybean oil, mineral oil, sesame oil, and the like). Preferred liquid carriers, particularly for injectable solutions, include water, saline, aqueous dextrose and glycols.

The amount of a compound of the invention in the composition may vary widely depending upon the type of formulation, size of a unit dosage, kind of excipients and other factors known to those of skill in the art of pharmaceutical sciences. In general, a composition of a compound of the invention for treating a given disease will comprise from 0.01% w to 10% w, preferably 0.3% w to 1% w, of active ingredient with the remainder being the excipient or excipients. Preferably the pharmaceutical composition is administered in a single unit dosage form for continuous treatment or in a single unit dosage form ad libitum when relief of symptoms is specifically required. Representative pharmaceutical formulations containing a compound of the invention are described in Example 35.

Chemistry:

Processes for Making Compounds of the Invention:

Compounds of the invention may be prepared by the application or adaptation of known methods, by which is meant methods used heretofore or described in the literature, for example those described by R. C. Larock in Comprehensive Organic Transformations, VCH publishers, 1989.

In the reactions described hereinafter it may be necessary to protect reactive functional groups, for example hydroxy, amino, imino, thio or carboxy groups, where these are desired in the final product, to avoid their unwanted participation in the reactions. Conventional protecting groups may be used in accordance with standard practice, for examples see T. W.

Greene and P. G. M. Wuts in "Protective Groups in Organic Chemistry" John Wiley and Sons, 1991.

Compounds of the invention can be prepared by proceeding according to Reaction Scheme 1:

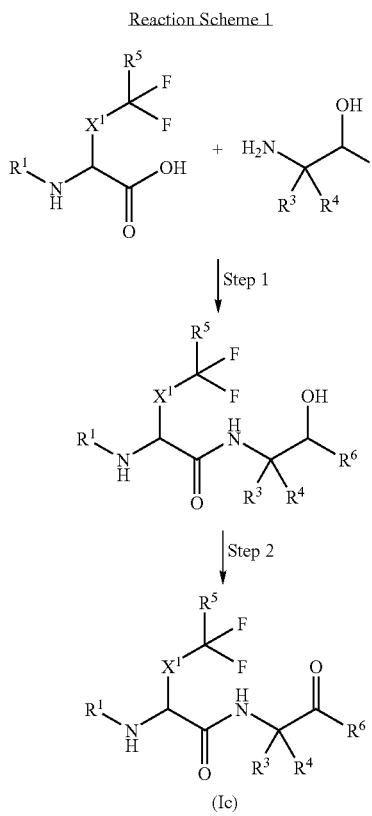

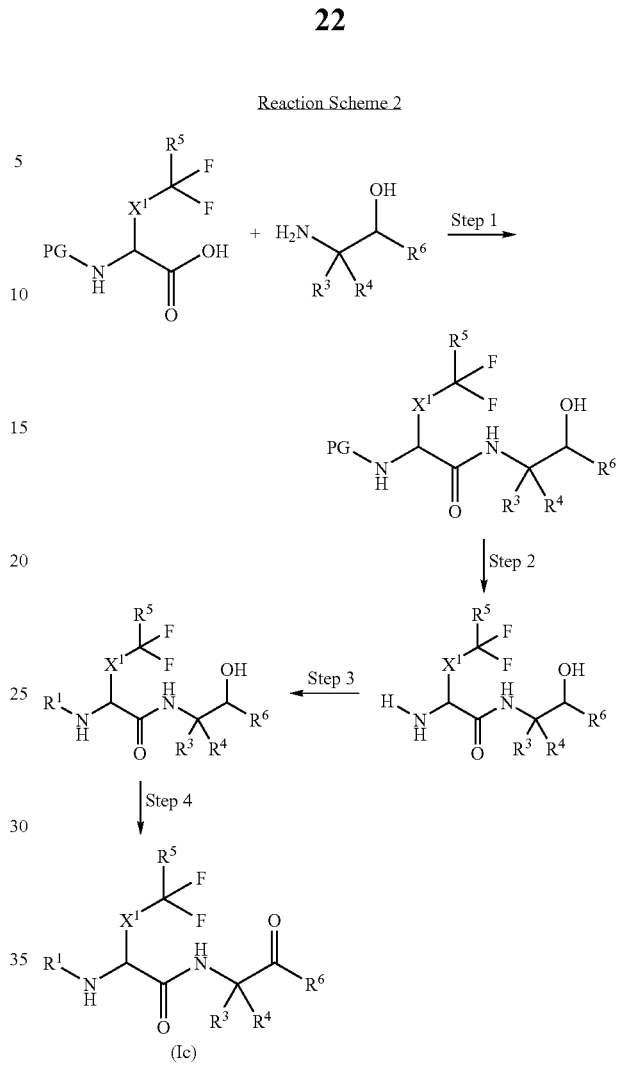

in which each $X^1$, $R^1$, $R^3$, $R^4$, $R^5$, and $R^6$ are as defined in the Summary of the Invention. Thus, in step 1, an acid may be condensed with an amino compound of formula to give a β-hydroxy amide. The condensation reaction can be effected with an appropriate coupling agent (e.g., benzotriazol-1-yloxytrispyrrolidinophosphonium hexafluorophosphate (PyBOP®), 1-(3-dimethylaminopropyl)-3-ethylcarbodiimide hydrochloride (EDCI), O-benzotriazol-1-yl-N,N,N',N'-tetramethyluronium hexafluorophosphate (HBTU), 1,3-dicyclohexylcarbodiimide (DCC), or the like) and optionally an appropriate catalyst (e.g., 1-hydroxybenzotriazole (HOBt), 1-hydroxy-7-azabenzotriazole (HOAt), O-(7-azabenzotriazol-1-yl)-1,1,3,3, tetra-methyluroniumhexafluorophosphate (HATU), or the like) and non-nucleophilic base (e.g., triethylamine, N-methylmorpholine, and the like, or any suitable combination thereof) at ambient temperature and requires 2 to 10 hours to complete. The β-hydroxy amide may then be oxidized, in step 2, to give a compound of formula (Ic). The oxidation reaction may conveniently be carried out using Dess-Martin periodinane in an inert solvent, such as dichloromethane, and at a temperature from about 0° C. to about room temperature.

Alternatively the compounds of this invention can be prepared by proceeding according to Reaction Scheme 2:

in which each $X^1$, $R^1$, $R^3$, $R^4$, $R^5$, and $R^6$ are as defined in the Summary of the Invention and suitable protecting group. Thus, in step 1, an acid may be condensed with an amino compound of formula to give a β-hydroxy amide. Removal of the protecting group (Step 2) followed by introduction of $R^1$ group (Step 3) and oxidation (Step 4) to give a compound of formula (Ic).

EXAMPLES

The present invention is further exemplified, but not limited by, the following examples that illustrate the preparation of compounds of Formula (I) (Examples) and intermediates (References) according to the invention.

$^1$H nuclear magnetic resonance spectra (NMR) were recorded on Varian Mercury-300 or Unity-400 or UnityPlus-500 or Inova-500 machines. In the nuclear magnetic resonance spectra (NMR) the chemical shifts (δ) are expressed in ppm relative to tetramethylsilane. Abbreviations have the following significances: s=singlet; d=doublet; t=triplet; m=multiplet; q=quartet; dd=doublet of doublets; ddd=doublet of double doublets.

The high pressure liquid chromatography (HPLC) was run on Kromasil 10 micron, 100A Silica, 4.6 mmIDx250 mm column using mixture of Heptane/THF/1,2-Dichloroethane as Mobile Phase. Mass spectra were run on Agilent 1100 series or MICROMASS LCT-TOF MS. The thin layer chromatography (TLC) $R_F$ values were determined using Merck silica plates.

Abbreviations

CBZ—Benzyloxy carbonyl
DAST—(Diethylamino)sulfur trifluoride
DCM—Dichloromethane
DMF—Dimethyl formamide
DMSO—Dimethyl sulfoxide
DTT—Dithiothreitol
EDCI—N-(3-Dimethylaminopropyl)-N¢-ethylcarbodiimide hydrochloride
EDTA—Ethylenediaminetetraacetic acid
EtOAc—Ethyl acetate
HOBT—1-Hydroxybenzotriazole hydrate
MeOH—Methanol
MES—2-Morpholinoethanesulfonic acid
PyBOP—(Benzotriazol-1-yloxy)tripyrrolidinophosphonium hexafluorophosphate
THF—Tetrahydrofuran Reference 1

(S)-2-Benzyloxycarbonylamino-4-oxo-5-phenyl-pentanoic acid methyl ester

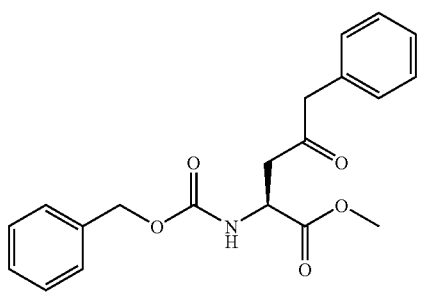

To a suspension of copper (I) bromide (4.26 mmol, 611.1 mg) in 3 mL of dry THF under $N_2$ is added a solution of lithium bromide (8.52 mmol, 740 mg) in 5 mL of dry THF. The mixture is stirred at room temperature for 20 min, and then cooled to −78° C. A solution of benzyl magnesium chloride (20 wt. % in THF, 4.26 mmol, 3.25 mL) followed by a solution of (S)-2-benzyloxycarbonylamino-3-chlorocarbonyl-propionic acid methyl ester [Ref: Synth. Comm 1993, 23(18), 2511-2526] (3.59 mmol) in 7 mL of dry THF is added. The mixture is stirred at −78° C. for 30 min and then quenched with saturated $NH_4Cl$ (50 mL). The mixture is extracted twice with ethyl acetate (30 mL). The organic layers are dried over magnesium sulfate and then concentrated in vacuum. The residue is purified over 35 g silica gel, eluting with EtOAc:Heptane (1:1) to afford (S)-2-benzyloxycarbonyl-amino-4-oxo-5-phenyl-pentanoic acid methyl ester (1.07 g, 84%).

$^1$H NMR (CDCl$_3$): δ 7.4-7.17 (m, 10H), 5.73 (d, J=8.2 Hz, 1H), 5.11 (s, 2H), 4,57 (m, 1H), 3.7 (2×s, 5H), 3.24 (dd, J=18.5, 4.4 Hz, 1H), 3.0 (dd, J=18.2, 4.1 Hz, 1H); LC/MS: 100% 378 (M+Na).

Reference 2

(S)-2-Benzyloxycarbonylamino-4-oxo-heptanoic acid methyl ester

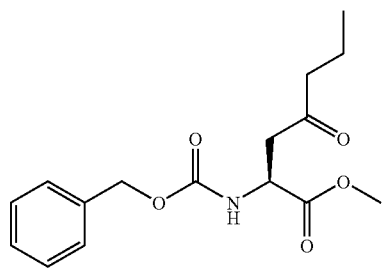

By proceeding in a similar manner to Reference Example 1 above but using propyl magnesium chloride instead of benzyl magnesium chloride there is prepared (S)-2-benzyloxycarbonylamino-4-oxo-heptanoic acid methyl ester.

$^1$H NMR (CDCl$_3$): δ 7.35 (m, 5H), 5.78 (d, J=8.5 Hz, 1H), 5.13 (s, 2H), 4.58 (m, 1H), 3.75 (s, 3H), 3.2 (dd, J=18.3, 4.2 Hz, 1H), 2.96 (dd, J=18.3, 4.1 Hz, 1H), 2.4 (m, 2H), 1.6 (m, 2H), 0.92 (t, J=7.4 Hz, 3H); LC/MS: 330 (M+Na).

Reference 3

(S)-2-Benzyloxycarbonylamino-4,4-difluoro-5-phenyl-pentanoic acid methyl ester

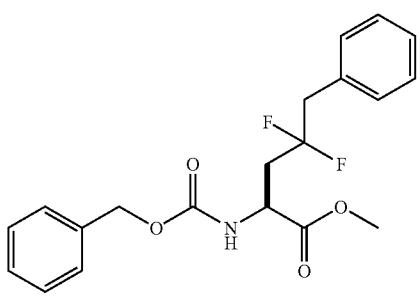

A mixture of 2-benzyloxycarbonylamino-4-oxo-5-phenyl-pentanoic acid methyl ester (3.310 g, 9.31 mmol) and DAST (7 mL) is stirred at room temperature over 3 days. The mixture is diluted with dichloromethane (100 mL) and carefully added to 0.5N NaOH solution (150 mL). The aqueous layer is extracted with dichloromethane (50 mL). The organic layers are dried over magnesium sulfate and then concentrated in vacuum. The residue is purified over 110 g silica gel, eluting with EtOAc:Heptane (1:4 then 1:3) to afford (S)-2-benzyloxycarbonylamino-4,4-difluoro-5-phenyl-pentanoic acid methyl ester (1.797 g, 51.1%).

¹H NMR (CDCl₃) δ 7.3 (m, 10H), 5.43 (d, J=7.6 Hz, 1H), 5.14 (s, 2H), 4.65 (m, 1H), 3.74 (s, 3H), 3.2 (t, J=16.5 Hz, 2H), 2.4 (m, 2H); LC/MS: 97% 400 (M+Na).

Reference 4

(S)-2-Amino-4,4-difluoro-5-phenyl-pentanoic acid methyl ester hydrochloride

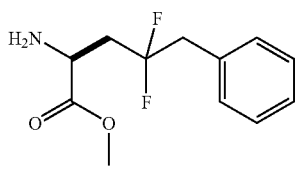

A solution of (S)-2-benzyloxycarbonylamino-4,4-difluoro-5-phenyl-pentanoic acid methyl ester (7.806 g, 20.68 mmol) in 120 mL of methanol and 4 M HCl in dioxane (41.4 mmol, 10.3 mL) is hydrogenated over 10% Pd/C (1.0 g) at 50 psi. After 8 hr, another portion of 10% Pd/C (1.0 g) is added. After 24 hr, the catalyst is removed by filtration over a pad of Celite, and the filtrate is concentrated in vacuum. The resulting solid is dissolved in a minimum amount of methanol and slowly added to ether (150 mL). The resulting slurry is aged for 30 min and then filtered. The solid is dried under suction to afford (S)-2-amino-4,4-difluoro-5-phenyl-pentanoic acid methyl ester hydrochloride (4.950 g, 85.5%).

¹H NMR (DMSO-D₆): δ 8.6 (b, 3H), 7.3 (m, 5H), 4.26 (t, J=6 Hz, 1H), 3.73 (s, 3H), 3.3 (t, J=17.5 Hz, 2H), 2.55 (m, 2H); LC/MS: 100% 244 (M+1).

Reference 5

(S)-4,4-Difluoro-2-[(morpholine-4-carbonyl)-amino]-5-phenyl-pentanoic acid methyl ester

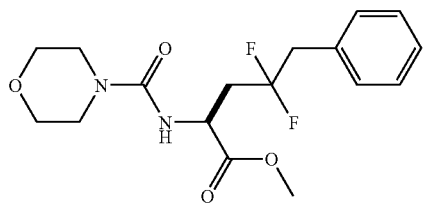

To a mixture of (S)-2-amino-4,4-difluoro-5-phenyl-pentanoic acid methyl ester hydrochloride (2.50 g, 8.94 mmol) and diisopropyl amine (22.3 mmol, 2.89 g) in dry dichloromethane (40 mL) under N₂ is added drop wise morpholine carbonyl chloride (13.4 mmol, 2.0 g). The mixture is stirred at room temperature for 15 hours, and then diluted with water (50 mL). The aqueous layer is extracted with dichloromethane (30 mL). The organic layers are dried over magnesium sulfate and then concentrated in vacuum. Purification over 110 g silica gel, eluting with EtOAc:Heptane (1:1, then 2:1) affords (S)-4,4-difluoro-2-[(morpholine-4-carbonyl)-amino]-5-phenyl-pentanoic acid methyl ester (2.82 g, 88.5%).

¹H NMR (CDCl₃): δ 7.3 (m, 5H), 5.16 (d, J=7.5 Hz, 1H), 4.75 (dd, J=13, 6 Hz, 1H), 3.73 (s, 3H), 3.7 (m, 4H), 3.4 (m, 4H), 3.2 (t, J=16.7 Hz, 2H), 2.4 (m, 2H). LC/MS: 100% 357 (M+1).

Reference 6

(S)-4,4-Difluoro-2-[(morpholine-4-carbonyl)-amino]-5-phenyl-pentanoic acid

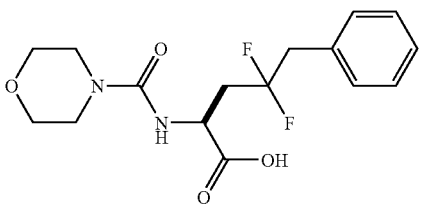

To a solution of (S)-4,4-difluoro-2-[(morpholine-4-carbonyl)-amino]-5-phenyl-pentanoic acid methyl ester (2.81 g, 7.88 mmol) in MeOH:H₂O (2:1 vol, 40 mL) is added LiOH mono hydrate (662 mg, 15.76 mmol). The mixture is stirred at room temperature for 2.5 h, and then diluted with water (30 mL). Methanol is removed in vacuum. The pH is adjusted to pH 1 with 6N HCl and the aqueous layer is extracted with dichloromethane (2×30 mL). The organic layers are dried over magnesium sulfate and concentrated in vacuum to afford (S)-4,4-Difluoro-2-[(morpholine-4-carbonyl)-amino]-5-phenyl-pentanoic acid (2.509 g, 93%).

¹H NMR (CDCl₃): δ 8.2 (b, 1H), 7.3 (m, 5H), 5.3 (m, 1H), 4.6 (m, 1H), 3.65 (m, 4H), 3.4 (m, 4H), 3.2 (t, J=16.5 Hz, 2H), 2.4 (m, 2H); LC/MS: 94% 343 (MH⁺)

Reference 7

(S)-5-Benzyloxycarbonylamino-2-isopropyl-3-oxo-hexanedioic acid 1-tert-butyl ester 6-methyl ester

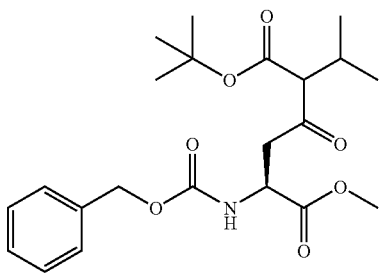

To a cooled to −78° C. solution of diisopropyl amine (3.53 g, 34.88 mmol) in dry THF (20 mL) under N₂ is added drop wise a solution of n-butyl lithium (2.5 M in hexane, 34.88 mmol, 13.95 mL). The mixture is stirred at −78° C. for 30 min then a solution of 3-Methyl-butyric acid tert-butyl ester (34.88 mmol, 5.52 g) in THF (40 mL) is added. The mixture is stirred at −78° C. for 30 min then a solution of (S)-2-Benzyloxycarbonylamino-3-chlorocarbonyl-propionic acid methyl (Ref: Synth. Comm 1993, 23(18), 2511-2526) (16.6 mmol) in 30 mL of dry THF is added drop wise. After stirring for another 2 hr at −78° C., the reaction is quenched with 50 mL of 1N HCl and warmed to room temperature. The pH is adjusted to pH 3 with 1N NaOH and the THF is removed in vacuum. The organic layer is extracted with EtOAc (2×60 mL). The organic layers are dried over magnesium sulfate and then concentrated in vacuum. The residue is purified over 90 g silica gel, eluting with EtOAc:Heptane (1:3 then 1:2) to afford (S)-5-Benzyloxycarbonylamino-2-isopropyl-3-oxo-hexanedioic acid 1-tert-butyl ester 6-methyl ester (2.417 g, 34.5%).

¹H NMR (CDCl₃): δ 7.4 (m, 5H), 5.73 (d, J=8.4 Hz, 1H), 5.12 (s, 2H), 4.6 (m, 1H), 3.74 (s, 3), 3.39-3.06 (m, 3H), 2.4 (m, 1H), 1.45 (2s, 9H), 0.98 (d, J=6.6 Hz, 3H), 0.88 (d, J=6.7 Hz, 3H); LC/MS: 100% 422 (M+1).

Reference 8

(S)-2-Benzyloxycarbonylamino-4-oxo-hexanedioic acid 6-tert-butyl ester 1-methyl ester

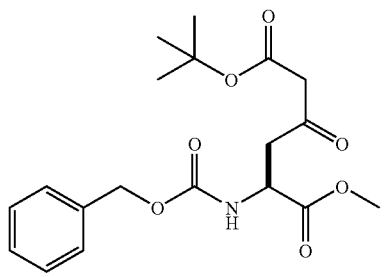

To a solution of N-CBZ L-aspartic acid 1-methyl ester (1.00 g, 3.55 mmol) in dry tetrahydrofuran (17 mL) is added carbonyl diimidazole (634.1 mg, 3.91 mmol). The mixture is stirred at room temperature for 6 hr then the magnesium salt of mono-tert butyl malonate (1.339 g, 3.91 mmol) (prepared according to Angew. Chem. Int. Ed. Engl. 1979, 18(1), 72-74) is added. The mixture is stirred at room temperature for another 20 h, then concentrated in vacuum. The residue is partitioned between ether (60 mL) and 0.5 N HCl (60 mL). The organic layer is washed with saturated NaHCO₃ solution (50 mL) then dried over magnesium sulfate and concentrated in vacuum. The residue is purified over 35 g of silica gel, eluted with EtOAc:Heptane (1:1) to afford (S)-2-Benzyloxycarbonylamino-4-oxo-hexanedioic acid 6-tert-butyl ester 1-methyl ester (1.17 g, 87%).

¹H NMR (CDCl₃): δ 7.4 (m, 5H), 5.73 (d, J=8.3 Hz, 1H), 5.1 (s, 2H), 4.6 (m, 1H), 3.75 (s, 3H), 3.37 (s, 2H), 3.32 (dd, J=18.7, 4.3 Hz, 1H), 3.13 (dd, J=18.5, 4.1 Hz, 1H), 1.47 (s, 9H); LC/MS: 93% 402 (M+Na).

Reference 9

(S)-2-Benzyloxycarbonylamino-6-methyl-4-oxo-heptanoic acid methyl ester

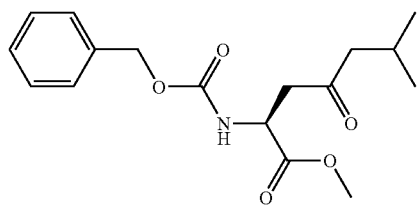

A solution of 5-Benzyloxycarbonylamino-2-isopropyl-3-oxo-hexanedioic acid 1-tert-butyl ester 6-methyl ester (1.06 g, 2.51 mmol) and p-toluenesulfonic acid monohydrate (35.8 mg, 0.19 mmol) in toluene (20 mL) is heated to reflux under N₂ for 6.5 hr. The mixture is cooled to room temperature, and concentrated in vacuum. The residue is purified over 35 g silica gel, eluting with EtOAc:Heptane (1:4) to afford (S)-2-Benzyloxycarbonylamino-6-methyl-4-oxo-heptanoic acid methyl ester (727 mg, 90%). ¹H NMR (CDCl₃): δ 7.4 (m, 5H), 5.78 (d, J=9.1 Hz, 1H), 5.13 (s, 2H), 4.6 (m, 1H), 3.74 (s, 3H), 3.2 (dd, J=18.3, 4.4 Hz, 1H), 2.95 (dd, J=18.2, 4.0 Hz, 1H), 2.3 (m, 2H), 2.1 (m, 1H), 0.92 (d, J=6.7 Hz, 6H); LC/MS: 77% 322 (MH⁺).

Reference 10

(S)-2-Benzyloxycarbonylamino-4-oxo-pentanoic acid methyl ester

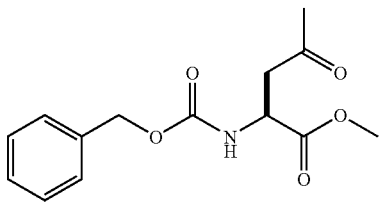

By proceeding in a similar manner to Reference Example 9 above but using 2-benzyloxycarbonylamino-4-oxo-hexanedioic acid 6-tert-butyl ester 1-methyl ester there is prepared (S)-2-benzyloxycarbonylamino-4-oxo-pentanoic acid methyl ester ¹H NMR (CDCl₃): δ 7.4 (m, 5H), 5.76 (d, J=8.1 Hz, 1H), 5.14 (s, 2H), 4.57 (m, 1H), 3.75 (s, 3H), 3.23 (dd, J=18.4, 4.3 Hz, 1H), 3.0 (dd, J=18.4, 4.3 Hz, 1H), 2.18 (s, 3H); LC/MS: >85% 280 (MH⁺).

Alternate Method

To a cooled to 0° C. suspension of copper (I) iodide in ether (20 mL) under N₂ is slowly added methyl lithium (1.6 M solution in ether, 21.3 mmol, 13.3 mL). The mixture is stirred at 0° C. for 10 min then cooled to −78° C. A solution of 3.55 mmol of (S)-2-Benzyloxycarbonylamino-3-chlorocarbonyl-propionic acid methyl ester (Ref: Synth. Comm 1993, 23(18), 2511-2526) in 12 mL of dry THF is added drop wise. The mixture is stirred at −78° C. for 30 min then quenched by adding methanol (2 mL). The mixture is poured into saturated NH₄Cl (80 mL) and extracted with ether (2×40 mL). The organic layers are dried over magnesium sulfate and concentrated in vacuum. The residue is purified over 35 g silica gel, eluted with EtOAc:Heptane (1:1) to afford (S)-2-benzyloxycarbonylamino-4-oxo-pentanoic acid methyl ester (261 mg, 26%).

Reference 11

(S)-2-Benzyloxycarbonylamino-4,4-difluoro-6-methyl-heptanoic acid methyl ester

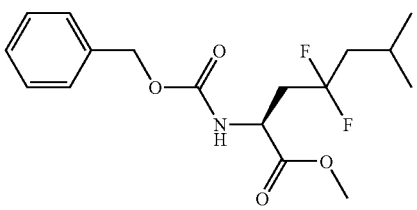

A mixture of (S)-2-benzyloxycarbonylamino-6-methyl-4-oxo-heptanoic acid methyl ester (915 mg, 2.85 mmol) and DAST (3 mL, XS) is stirred at 35° C. for 47 h. The mixture is diluted with dichloromethane (50 mL) and carefully added to saturated NaHCO₃ solution (150 mL). The aqueous layer is extracted with dichloromethane (30 mL). The organic layers are dried over magnesium sulfate and concentrated in vacuum. The residue is purified over 35 g silica gel, eluting with EtOAc:Heptane (1:4) to afford (S)-2-Benzyloxycarbonylamino-4,4-difluoro-6-methyl-heptanoic acid methyl ester (156 mg, 16%).

$^1$H NMR (CDCl$_3$): δ 7.4 (m, 5H), 5.48 (d, J=7.9 Hz, 1H), 5.15 (s, 2H), 4.61 (q, J=5.9 Hz, 1H), 3.78 (s, 3H), 2.4 (m, 2H), 1.95 (m, 1H), 1.8 (m, 2H), 0.98 (d, J=6.6 Hz, 6H); LC/MS: 98% 366 (M+Na).

Reference 12

(S)-2-Benzyloxycarbonylamino-4,4-difluoro-pentanoic acid methyl ester

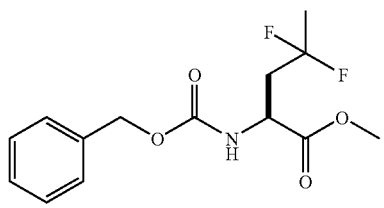

By proceeding in a similar manner to Reference Example 11 above but using (S)-2-benzyloxycarbonylamino-4-oxo-pentanoic acid methyl ester there is prepared (S)-2-benzyloxycarbonylamino-4,4-difluoro-pentanoic acid methyl ester $^1$H NMR (CDCl$_3$): δ 7.4 (m, 5H), 5.46 (d, J=7.1 Hz, 1H), 5.15 (s, 2H), 4.61 (q, J=7.3 Hz, 1H), 3.78 (s, 3H), 2.45 (m, 2H), 1.67 (t, J=18.8 Hz, 3H); LC/MS: 94% 324 (M+Na).

Reference 13

(S)-2-Benzyloxycarbonylamino-4,4-difluoro-heptanoic acid methyl ester

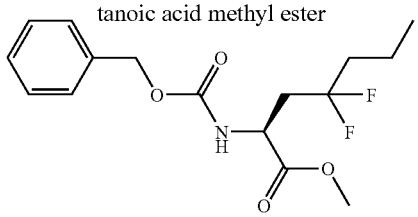

By proceeding in a similar manner to Reference Example 11 above but using (S)-2-benzyloxycarbonylamino-4-oxo-heptanoic acid methyl ester there is prepared (S)-2-benzyloxycarbonylamino-4,4-difluoro-heptanoic acid methyl ester.

LC/MS: 96% 330 (MH$^+$), 352 (M+Na).

Reference 14

(S)-2-Amino-4,4-difluoro-6-methyl-heptanoic acid methyl ester hydrochloride

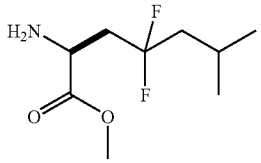

A solution of (S)-2-benzyloxycarbonylamino-4,4-difluoro-6-methyl-heptanoic acid methyl ester: (333 mg, 0.97 mmol) in methanol (10 mL) and 4 M HCl in dioxane (4 mmol, 1 mL) is hydrogenated over 10% Pd/C (150 mg) at 55 psi. After 7 hr, another portion of 10% Pd/C (200 mg) is added and the hydrogenation resumed. After 5.5 hr, the reaction did not progress. Catalyst is filtered and the filtrate is concentrated in vacuum and subjected to the hydrogenation conditions. After 6.5 hr, the catalyst is removed by filtration over a pad of Celite, and the filtrate is concentrated in vacuum to afford (S)-2-amino-4,4-difluoro-6-methyl-heptanoic acid methyl ester hydrochloride as a sticky solid (240 mg, quant.).

$^1$H NMR (CDCl$_3$): δ 4.8 (b, 3H), 4.35 (b, 1H), 3.84 (s, 3H), 2.6 (m, 2H), 1.9 (m, 3H), 0.99 (d, J=6.2 Hz, 6H); LC/MS: 90% 210 (M+1).

Reference 15

(S)-2-Amino-4,4-difluoro-pentanoic acid methyl ester hydrochloride

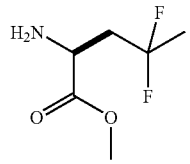

By proceeding in a similar manner to Reference Example 14 above but using (S)-2-benzyloxycarbonylamino-4,4-difluoro-pentanoic acid methyl ester there is prepared (S)-2-amino-4,4-difluoro-pentanoic acid methyl ester hydrochloride.

$^1$H NMR (CDCl$_3$): δ 4.8 (s, 3H), 4.37 (m, 1H), 3.86 (s, 3H), 2.4-2.8 (m, 2H), 1.73 (t, J=18.9 Hz, 3H); LC/MS: 100% 168 (M+1).

Reference 16

(S)-2-Amino-4,4-difluoro-heptanoic acid methyl ester hydrochloride

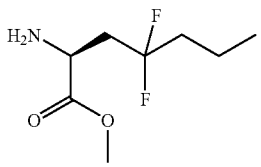

By proceeding in a similar manner to Reference Example 14 above but using (S)-2-benzyloxycarbonylamino-4,4-difluoro-heptanoic acid methyl ester there is prepared (S)-2-amino-4,4-difluoro-heptanoic acid methyl ester hydrochloride

LC/MS: 100% 196 (MH$^+$).

Reference 17

(S)-4,4-Difluoro-6-methyl-2-[(morpholine-4-carbonyl)-amino]-heptanoic acid methyl ester

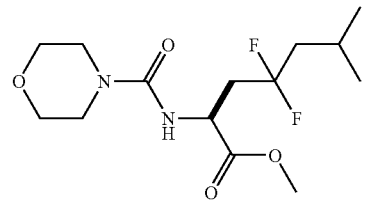

To a mixture of (S)-2-amino-4,4-difluoro-6-methyl-heptanoic acid methyl ester hydrochloride (238 mg, 0.97 mmol) and diisopropyl amine (2.42 mmol, 313 mg) in dry dichloromethane (5 mL) under $N_2$ is added drop wise morpholine carbonyl chloride (1.45 mmol, 218 mg). The mixture is stirred at room temperature for 23 h, then diluted with dichloromethane (25 mL) and washed with dilute HCl (30 mL), and saturated $NaHCO_3$ (30 mL). The organic layers are dried over magnesium sulfate and concentrated in vacuum. Purification over 12 g silica gel, eluting with EtOAc:Heptane (1:1, then 2:1) affords (S)-4,4-Difluoro-6-methyl-2-[(morpholine-4-carbonyl)-amino]-heptanoic acid methyl ester (206 mg, 66%).

$^1$H NMR (CDCl$_3$): δ 5.2 (d, J=7.4 Hz, 1H), 4.72 (dd, J=13, 6 Hz, 1H), 3.78 (s, 3H), 3.7 (m, 4H), 3.4 (m, 4H), 2.4 (m, 2H), 1.95 (m, 1H), 1.8 (m, 2H), 0.99 (d, J=6.4 Hz, 6H);LC/MS: 90% 345 (M+Na).

Reference 18

(S)-4,4-Difluoro-2-[(morpholine-4-carbonyl)-amino]-pentanoic acid methyl ester

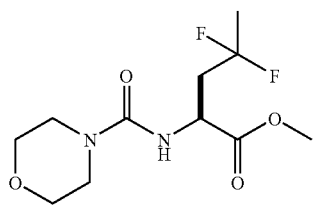

By proceeding in a similar manner to Reference Example 17 above but using (S)-2-amino-4,4-difluoro-pentanoic acid methyl ester hydrochloride there is prepared (S)-4,4-Difluoro-2-[(morpholine-4-carbonyl)-amino]-pentanoic acid methyl ester.

$^1$H NMR (CDCl$_3$): δ 5.18 (d, J=7.5 Hz, 1H), 4.71 (q, J=7 Hz, 1H), 3.78 (s, 3H), 3.71 (m, 4H), 3.4 (m, 4H), 2.37-2.55 (m, 2H), 1.67 (t, J=18.7 Hz, 3H); LC/MS: 100% 303 (M+Na).

Reference 19

(S)-4,4-Difluoro-2-[(morpholine-4-carbonyl)-amino]-heptanoic acid methyl ester

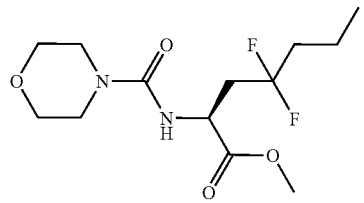

By proceeding in a similar manner to Reference Example 17 above but using (S)-2-amino-4,4-difluoro-heptanoic acid methyl ester hydrochloride there is prepared (S)-4,4-difluoro-2-[(morpholine-4-carbonyl)-amino]-heptanoic acid methyl ester LC/MS: 100% 309 (MH$^+$).

Reference 20

(S)-4,4-Difluoro-6-methyl-2-[(morpholine-4-carbonyl)-amino]-heptanoic acid

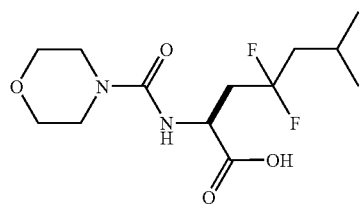

To a solution of methyl ester (205 mg, 0.63 mmol) in MeOH: H2O (2:1 vol, 4 mL) is added LiOH-mono hydrate (80 mg, 1.9 mmol). The mixture is stirred at room temperature for 21 h, then diluted with water (15 mL) and extracted with ether (20 mL). The pH of the aqueous layer is adjusted to pH 1 with 1N HCl and it is extracted with dichloromethane (2×20 mL). The organic layers are dried over magnesium sulfate and concentrated in vacuum to afford (S)-4,4-dDifluoro-6-methyl-2-[(morpholine-4-carbonyl)-amino]-heptanoic acid (168 mg, 86%).

$^1$H NMR (CDCl$_3$): δ 6.4 (b, 1H), 5.3 (d, J=6.2 Hz, 1H), 4.6 (m, 1H), 3.7 (m, 4H), 3.4 (m, 4H), 2.5 (m, 2H), 2.0 (m, 1H), 1.8 (m, 2H), 1.0 (d, J=6.6 Hz, 6H); LC/MS: 90% 309 (M+1).

Reference 21

(S)-4,4-Difluoro-2-[(morpholine4-carbonyl)-amino]-2pentanoic acid

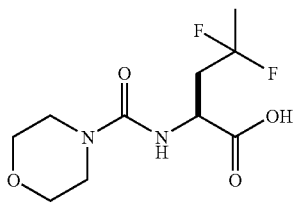

By proceeding in a similar manner to Reference Example 20 above but using (S)-4,4-Difluoro-2-[(morpholine4-carbonyl)-amino]-pentanoic acid methyl ester there is prepared (S)-4,4-Difluoro-2-[(morpholine4-carbonyl)-amino]-pentanoic acid $^1$H NMR (CDCl$_3$): δ 5.9 (b, 1H), 5.29 (d, J=6.3 Hz, 1H), 4.6 (m, 1H), 3.71 (m, 4H), 3.4 (m, 4H), 2.38-2.65 (m, 2H), 1.70 (t, J=18.9 Hz, 3H); LC/MS: 100% 267 (M+1).

Reference 22

(S)-4,4-Difluoro-2-[(morpholine-4-carbonyl)-amino]-heptanoic acid

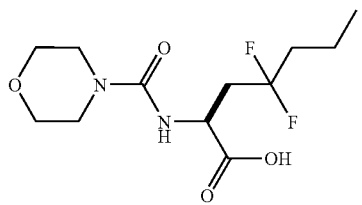

By proceeding in a similar manner to Reference Example 20 above but using (S)-4,4-difluoro-2-[(morpholine-4-carbonyl)-amino]-heptanoic acid methyl ester there is prepared (S)-4,4-difluoro-2-[(morpholine-4-carbonyl)-amino]-heptanoic acid $^1$H NMR (CDCl$_3$): δ 5.3 (b, 1H), 5.25 (d, J=5.4 Hz, 1H), 4.6 (m, 1H), 3.71 (m, 4H), 3.4 (m, 4H), 2.6-2.3 (m, 2H), 1.9 (m, 2H), 1.55 (m, 2H), 1.0 (t, J=7.3 Hz, 3H); LC/MS: 83% 295 (M+1).

Reference 23

5-Thiophen-2-yl-oxazole

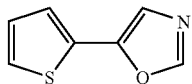

To a solution of p-toluenesulfonylmethyl isocyanide (3.0 g, 15.36 mmol) and Thiophene-2-carboxaldehyde (1.72 g, 15.36 mmol) in methanol (45 mL) under N$_2$ is added potassium carbonate (2.12 g, 15.36 mmol). The mixture is heated to reflux for 5 hr, then cooled and concentrated in vacuum (cold water bath). The residue is partitioned between ether (100 mL) and water (100 mL). The organic layer is washed with water (100 mL), dried over magnesium sulfate and then concentrated in vacuum. The residue is purified over 35 g silica gel, eluted with ethyl acetate: heptane (1:5) to afford 5-thiophen-2-yl-oxazole (0.852 g, 37%).

$^1$H NMR (CDCl$_3$): δ 7.9 (s, 1H), 7.3 (m, 2H), 7.2 (s, 1H), 7.1 (dd, J=5, 3.8 Hz, 1H); LC/MS: 100% 152 (M+1).

Reference 24

{(S)-1-[Hydroxy-(5-thiophen-2-yl-oxazol-2-yl)-methyl]-propyl}-carbamic acid tert-butyl ester

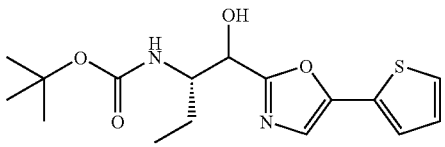

To a solution of 5-thiophen-2-yl-oxazole (0.85 g, 5.62 mmol) in dry THF (4 mL) is added triethylborane (1.0 M in THF, 5.62 mmol, 5.62 mL). The mixture is stirred at room temperature for 45 min, then cooled to −78° C. and n-butyl lithium (1.6 M in hexane, 5.62 mmol, 3.51 mL) is added drop wise. The mixture is stirred at −78° C. for 45 min then a solution of (1-Formyl-propyl)-carbamic acid tert-butyl ester (2.81 mmol, 0.526 g) in dry THF (3 mL) is added slowly. The mixture is stirred at −78° C. for 4 h, then warmed to 0° C. and quenched by adding 30 mL of 10% (vol) HOAc in ethanol. The mixture is stirred at room temperature for 18 hr and then concentrated in vacuum. The residue is purified over 90 g of silica gel, eluted with ethyl acetate: heptane (1:2 then 1:1) to afford {(S)-1-[hydroxy-(5-thiophen-2-yl-oxazol-2-yl)-methyl]-propyl}-carbamic acid tert-butyl ester (363 mg, 38%) as an oil.

$^1$H NMR (CDCl$_3$): δ (mixture of isomers) 7.35 (m, 2H), 7.1 (m, 2H), 4.9 (m, 2H), 4.0 (b, 1H), 3.6 (m, 1H), 1.8-1.55 (m, 2H), 1.4 and 1.3 (2s, 9H), 1.0 and 0.9 (2t, J=7.4 Hz, 3H); LC/MS: 100 339 (M+1).

Reference 25

(S)-2-Amino-1-(5-thiophen-2-yl-oxazol-2-yl)-butan-1-ol hydrochloride

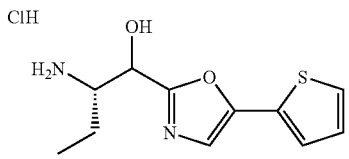

To a solution of {(S)-1-[hydroxy-(5-thiophen-2-yl-oxazol-2-yl)-methyl]-propyl}-carbamic acid tert-butyl ester (361 mg, 1.07 mmol) in dry dichloromethane (3 mL) is added 4N HCl in dioxane (3.0 mL, XS). The mixture is stirred at room temperature for 16 h, then concentrated in vacuum to afford (S)-2-Amino-1-(5-thiophen-2-yl-oxazol-2-yl)-butan-1-ol hydrochloride as a solid (quant.).

$^1$H NMR (CDCl$_3$): δ 7.5 (dd, J=5.2, 1.2 Hz, 1H), 7.4 (dd, J=3.6, 1.1 Hz, 1H), 7.3 (s, 1H), 7.1 (dd, J=5, 3.6 Hz, 1H), 4.8 (m, 3H), 3.6 (m, 2H), 3.3 (b, 1H), 1.75 (m, 2H), 1.0 (t, J=7.5 Hz, 3H); LC/MS: 100% 239 (M+1).

Reference 26

1-Ethyl-2-hydroxy-3-nitro-propyl)-carbamic acid tert-butyl ester

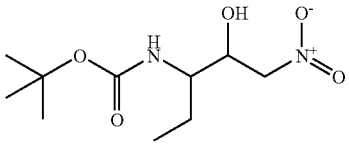

To a solution of (1-formyl-propyl)-carbamic acid tert-butyl ester (1.0 g, 5.34 mmol) in dry THF (10 mL) and ethanol is added nitromethane (3.91 g, 64.09 mmol) followed by triethylamine (2.70 g, 26.7 mmol). The mixture is stirred at room temperature for 22 h, and then concentrated in vacuum. The residue is diluted with ether (50 mL) and washed with concentrated NH₄Cl (60 mL). The ether layer is dried over magnesium sulfate and concentrated in vacuum. The residue is purified over 35 g silica gel, eluted with ethyl acetate: heptane (1:3) to afford the desired alcohol (1.09 g, 82%) as an oily solid.

$^1$H NMR (CDCl₃): δ 4.2-4.8 (m, 4H), 3.15-3.8 (m, 2H), 1.69-1.6 (m, 2H), 1.47 (2xs, 9H), 1.02 and 1.0 (2×t, J=7.1 Hz, 3H) LC/MS: 2 isomers, total 100% 149 (M-BOC+1).

Reference 27

(1-Ethyl-3-nitro-2-trimethylsilanyloxy-propyl)-carbamic acid tert-butyl ester

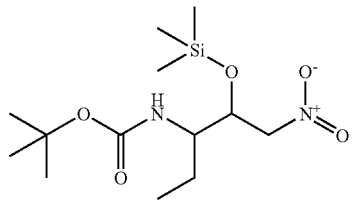

To a mixture of (1-ethyl-2-hydroxy-3-nitro-propyl)-carbamic acid tert-butyl ester (1.83 g, 7.37 mmol) and triethylamine (1.49 g, 14.75 mmol) in dry dichloromethane (25 mL) under N₂ is added trimethylsilyl chloride (1.20 g, 11.05 mmol). The mixture is stirred at room temperature for 24 h, then diluted with 40 mL of dichloromethane and washed with water (40 mL). The organic layer is dried over magnesium sulfate and concentrated in vacuum. The residue is purified over 110 g silica gel, eluted with ethyl acetate: heptane (1:4) to afford (1-ethyl-3-nitro-2-trimethylsilanyloxy-propyl)-carbamic acid tert-butyl ester (1.505 g, 86%) as an oil.

$^1$H NMR (CDCl₃): δ 4.4-4.65 (m, 4H); 3.55 (m, 1H), 1.2-1.7 (m, 1H), 0.98 (2×t, J=7.4 Hz, 3H), 0.13 (2s, 9H); LC/MS: 2 isomers, total 100% 221 (M-BOC+1).

Reference 28

{1-[(5-Isopropyl-isoxazol-3-yl)-trimethylsilanyloxy-methyl]-propyl}-carbamic acid tert-butyl ester

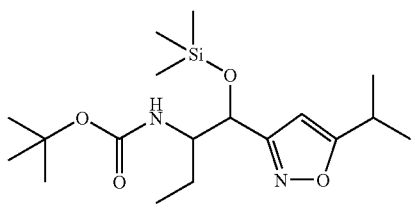

To a solution of (1-Ethyl-3-nitro-2-trimethylsilanyloxy-propyl)-carbamic acid tert-butyl ester (918 mg, 2.86 mmol), 1,4-Phenylene diisocyanate (1.38 g, 8.5 mmol) and 3-methyl-1-butyne (586 mg, 8.5 mmol) in dry toluene (15 mL) under N₂ is added triethylamine (10 drops). The mixture is heated to 50° C. in a sealed vial for 28 h, and then cooled to room temperature Water (1 mL) is added and the mixture is stirred for an additional 2 h, then filtered. The filtrate is concentrated in vacuum and the residue is purified over 35 g silica gel, eluted with ethyl acetate: heptane (1:5) to afford {1-[(5-Isopropyl-isoxazol-3-yl)-trimethylsilanyloxy-methyl]-propyl}-carbamic acid tert-butyl ester (764 mg, 72%) as an oil.

$^1$H NMR (CDCl₃): δ 6.0 (2s 1H), 4.4-4.9 (m, 2H), 3.7 (m, 1H), 3.0 (m, 1H) 1.2-1.6 (m, 17H), 1.0 (m, 3H), 0.11 and 0.1 (2xs, 9H); LC/MS: 2 isomers, total 67% 271 (M-BOC+1).

Reference 29

2-Amino-1-(5-isopropyl-isoxazol-3-yl)-butan-1-ol hydrochloride

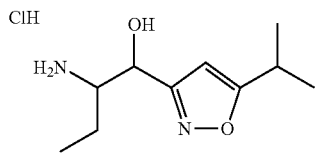

To a solution of {1-[(5-Isopropyl-isoxazol-3-yl)-trimethylsilanyloxy-methyl]-propyl}-carbamic acid tert-butyl ester in dry dichloromethane (5 mL) under N₂ is added a 4M solution of HCl in dioxane (5.0 mL, XS). The mixture is stirred at room temperature for 22 h, then concentrated in vacuum to afford the amine salt (475 mg, 99%) as a solid.

$^1$H NMR (CDCl₃): δ 6.25 (2xs, 1H), 5.0 (d, J=3.9 Hz, 1H), 4.8 (d, J=6.8 Hz, 1H), 3.4 (m, 1H), 3.1 (m, 1H), 1.5-1.7 (m, 2H), 1.3 (d, J=6.8 Hz, 6H); 1.0 (t, J=6.7 Hz, 3H); LC/MS: 100% 199 (M+1).

Reference 30

5-Methyl-3-oxazol-5-yl-isoxazole

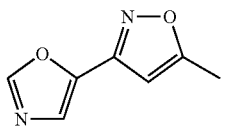

Diisobutylaluminum hydride (1.0M in DCM, 25.5 mL, 25.5 mmol) is added drop wise over 20 minutes to a solution of methyl-5-methylisoxazole-3-carboxylate (3.0 g, 21.3 mmol) in 35 mL of dry methylene chloride, with stirring at −78° C., and the reaction mixture is stirred at −78° C for 5.5 hours. The reaction is warmed to −40° C. and quenched with ice (60 g). After the biphasic mixture is allowed to warm to room temperature, potassium sodium tartrate tetrahydrate (100 mL saturated aqueous solution) is added. The bilayer are separated, the aqueous is extracted with methylene chloride. The organic extracts are dried over sodium sulfate and concentrated under reduced pressure to give 5-Methyl-isoxazole-3-carbaldehyde as a solid (1.3 g).

P-Toluenesulfonyl methyl isocyanide (1.75 g, 8.97 mmol) and Potassium carbonate (1.24 g, 8.97 mmol) are added to a solution of 5-Methyl-isoxazole-3-carbaldehyde (1.0 g, 8.97 mmol) in 35 mL of dry methanol and the reaction mixture is refluxed (90° C.) for 5 hours. The reaction is cooled to room temperature and concentrated under reduce pressure. The residue is partitioned in diethyl ether (100 mL) and water (200 mL). The organic layer is separated and the aqueous extracted with diethyl ether. The organic extracts are washed with brine and water, dried over sodium sulfate and concentrated under reduced pressure to give the title compound as a solid (1.25 g).

LC/MS: 87%, 238 (M+1)

Reference 31

((S)-1-{Hydroxy-[5-(5-methyl-isoxazol-3-yl)-oxazol-2-yl]-methyl}-propyl)-carbamic acid tert-butyl ester

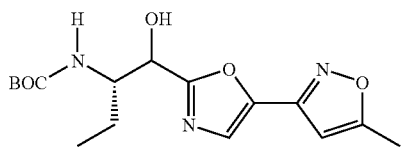

Triethylborane (1M in THF, 12 mL, 12 mmol) is added to a solution of 5-Methyl-3-oxazol-5-yl-isoxazole (1.8 g, 12 mmol) in 40 mL of dry Tetrahydrofuran and the mixture is stirred at room temperature for 15 minutes. The mixture is cooled to −78° C., nBuLi (2.5M in Hexanes, 4.8 mL, 12 mmol) is added drop wise and the mixture is stirred at −78° C. for 15 minutes. A solution of (S)-1-Formyl-propyl)-carbamic acid tert-butyl ester (898.7 mg, 4.8 mmol) in 15 mL of dry tetrahydrofuran is added drop wise and the reaction mixture is stirred at −78° C. for 3 hours, then let warm to −30° C. and quenched with acetic acid in ethanol (4%, 250 mL), stirring continued for 2 hours, while warming to room temperature. The reaction is concentrated under reduced pressure; the residue is dissolved in diethyl ether (250 mL) and stirred for 1.5 hours at room temperature. The precipitate is filtered; the filtrate is concentrated under reduced pressure. Column chromatography on silica eluting with a mixture of methylene chloride and ethyl acetate gives the title compound as a solid (830 mg).

LC/MS 100%, 338 (M+1)

Reference 32

(S)-2-Amino-1-[5-(5-methyl-isoxazol-3-yl)-oxazol-2-yl]-butan-1-ol; hydrochloride

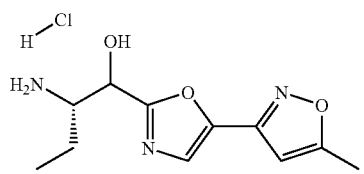

Hydrogen chloride (4M in 1,4-dioxane, 3.3 mL) is added dropwise to a solution of ((S)-1-{Hydroxy-[5-(5-methyl-isoxazol-3-yl)-oxazol-2-yl]-methyl}-propyl)-carbamic acid tert-butyl ester (0.75 g, 2.22 mmol) in 10 mL of methylene chloride an the reaction mixture is stirred at room temperature for 2.5 hours. The reaction is diluted with diethyl ether (50 mL) and stirred for another hour at room temperature, concentrated in reduced pressure to give the title compound as a solid (0.75 g).

$^1$H NMR [(CD)$_3$SO]: δ 8.18 (m, 3H), 7.84 (s, 1H), 6.70 (s, 1H), 4.90 (m, 1H), 3.58 (m, 2H), 2.50 (s, 3H), 1.60 (m, 2H), 0.90 (t, 3H), LC/MS 100%, 238 (M+1)

Reference 33

(S)-2-Amino-1-(3-cyclopropyl-1,2,4-oxadiazol-5-yl)-butan-1-ol

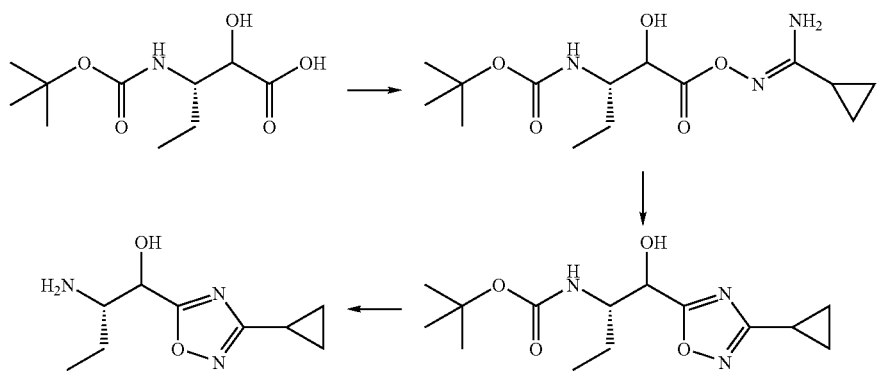

A solution of (S)-3-tert-Butoxycarbonylamino-2-hydroxy-pentanoic acid (2.00 g, 8.57 mmol) and N-hydroxycyclopropanecarboxamidine (1.03 g, 10.29 mmol) in dichloromethane (20 mL) is stirred at 0° C. and 1.25 equivalents of N-cyclohexylcarbodiimide-N'-methyl polystyrene (1.70 mmol/g, 6.30 g, 10.72 mmol) is added in portions. The reaction mixture stirred under nitrogen for three hours while warming to 15° C. The reaction mixture is filtered, the resin washed with dichloromethane and the filtrate evaporated under vacuum to dryness. [LC/MS m/z=338 (M+H+Na)].

The residue is dissolved in tetrahydrofuran (20 mL) and heated in a microwave reactor (Smith Creator) at 160° C. for three minutes, cooled to room temperature and evaporated under vacuum to dryness. [LC/MS n/z=320 (M+H+Na)]. The residue is dissolved in dichloromethane (50 mL) and stirred at room temperature as a 50 mL solution of 50% trifluoroacetic acid in dichloromethane is added drop wise. After three hours the reaction is evaporated under vacuum to dryness and dissolved in 50 mL of dichloromethane again. Three equivalents of Silicycle triamine-3 is added and the mixture stirred at room temperature overnight. The mixture is filtered and washed with dichloromethane. Evaporate under vacuum to give 1.04 g (61% overall). [LC/MS m/z=198 (M+H)]

Alternatively, deprotection of the BOC protecting group is carried out with HCl in dioxane to give (S)-2-amino-1-(3-cyclopropyl-1,2,4-oxadiazol-5-yl)-butan-1-ol hydrochloride.

Reference 34

(S)-2-Amino-1-(3-phenyl-1,2,4-oxadiazol-5-yl)-butan-1-ol

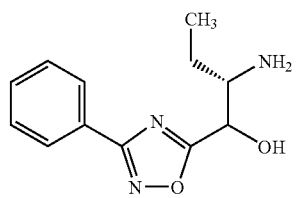

A solution of (S)-3-tert-Butoxycarbonylamino-2-hydroxy-pentanoic acid (2.00 g, 8.57 mmol) and N-hydroxybenzamidine (1.3 g, 9.5 mmol) in dichloromethane (40 mL) is stirred at 0° C. N-cyclohexylcarbodiimide-N'-methyl polystyrene (1.90 mmol/g, 6 g, 11.4 mmol) is added in portions. The reaction mixture is stirred under nitrogen for one hour. The reaction mixture is filtered, the resin washed with dichloromethane and the filtrate evaporated under vacuum to dryness. [LC/MS m/z=352 (M+H$^+$), 296(M+H$^+$-isobutene)]. The residue is dissolved in tetrahydrofuran (20 mL) and heated in a microwave reactor (Smith Creator) at 180° C. for three minutes, cooled to room temperature and evaporated under vacuum to dryness. The residue is purified via flash chromatography (eluted with a gradient from 5% to 65% ethyl acetate in heptane) to give the product as a solid [LC/MS m/z=356 (M+Na$^+$), 234 (M+H$^+$-Boc)].

The product is dissolved in dichloromethane (45 mL) and trifluoroacetic acid (5 mL) is added. After two hours the reaction is evaporated under vacuum to dryness. The residue is re-dissolved in 50mL of dichloromethane. Silicycle triamine-3 (9.9 g, 39 mmol) is added and the mixture stirred at room temperature overnight. The mixture is filtered and washed with dichloromethane. The filtrate is concentrated under vacuum to give (S)-2-Amino-1-(3-phenyl-1,2,4-oxadiazol-5-yl)-butan-1-ol (775 mg, 38%) as a solid.

$^1$H NMR (CDCl$_3$):δ 8.12-8.06 (m, 2H), 7.54-7.45 (m, 3H), 4.93 & 4.75 (2×d, J=5 Hz & 3.5 Hz, 1H), 3.25 &3.11 (2×m, 1H), 1.78-1.42 (2×m, 2H), 1.04 & 1.01 (2×t, J=7.5 Hz, 3H). [LC/MS m/z=234 (M+H)].

Reference 35

(S)-2-Amino-1-(5-phenyl-[1,2,4]oxadiazol-3-yl)-butan-1-ol

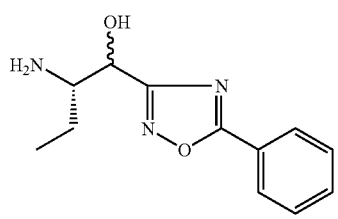

Synthesized as described in the following reaction scheme:

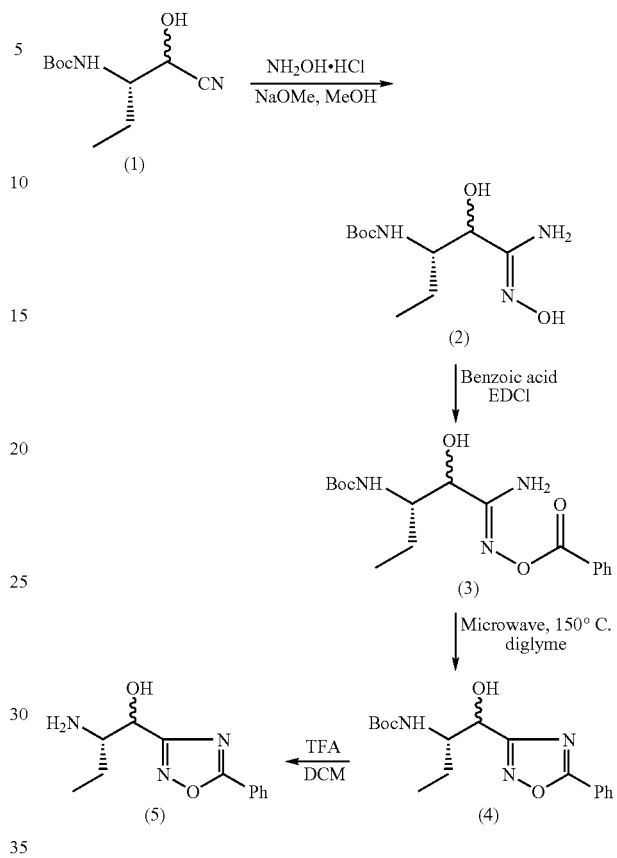

{(S)-1-[Hydroxy-(N-hydroxycarbamimidoyl)-methyl]-propyl}-carbamic acid tert-butyl ester (2)

A solution of (2-cyano-1-ethyl-2-hydroxy-ethyl)-carbamic acid tert-butyl ester (9.53 g, 44 mmol) in methanol (80 mL) is cooled to 0° C. and treated successively with hydroxylamine hydrochloride (3.05 g, 44 mmol) in methanol (80 mL) and 25% sodium methoxide solution in methanol (10.2 mL). After stirring at 0° C. for 5 minutes the reaction mixture stirred at room temperature for 5 hours and then evaporated. The residue is partitioned between ethyl acetate and water. The organic layer is separated, dried over magnesium sulfate and then evaporated under reduced pressure. The residual oil is subjected to mplc, eluting with a mixture of ethyl acetate and heptane to give {(S)-1-[hydroxy-(N-hydroxycarbamimidoyl)-methyl]-propyl}-carbamic acid tert-butyl ester (3.5 g) as a solid. MS: MH$^+$248.

{1-[Hydroxy-(N-benzoyloxycarbamimidoyl)-methyl]-propyl}-carbamicacid tert-butyl ester (3)

A solution of {1-[hydroxy-(N-hydroxycarbamimidoyl)-methyl]-propyl}-carbamic acid tert-butyl ester (2) (2.5 g, 10 mmol) in dichloromethane (125 mL) is treated with benzoic acid (1.36 g, 11 mmol), EDCI (2.14 g, 11 mmol), HOBT (1.37 g, 10 mmol) and triethylamine (1.35 mL, 11 mmol) and stirred at room temperature overnight. The reaction mixture is washed with saturated sodium bicarbonate solution, then water, then dried over Na$_2$SO$_4$ and then evaporated under reduced pressure. The residue is subjected to mplc eluting with 1% triethylamine in 2:3 v/v ethyl acetate and heptane mixture to give {1-[hydroxy-(N-benzoyloxycarbamimidoyl)-methyl]-propyl}-carbamicacid tert-butyl ester (850 mg) as a solid. MS: MH+ 352.

2-Amino-1-(5-phenyl-[1,2,4]oxadiazol-3-yl)-butan-1-ol (5)

A solution of (3) (1.5 g, 4.3 mmol) in diglyme is heated at 150° C. in a microwave reactor (Smith Creator, S00219) for 40 minutes. Solvent evaporated under vacuum in Genevac Evaporator at 80° C. for 3hours to give a solid. This is taken in dichloromethane (40 mL) and treated with trifluoroacetic acid at room temperature for 2 hours. Solvent evaporated to dryness under reduced pressure, crude taken in water, washed with DCM, aqueous layer basified with 1M NaOH solution and extracted with dichloromethane. Organic layer dried over $Na_2SO_4$ and evaporated under reduced pressure to give 2-amino-1-(5-phenyl-[1,2,4]oxadiazol-3-yl)-butan-1-ol (300 mg) as a solid.

$^1$HNMR (CDCl$_3$): δ 8.14-8.10 (m, 2H), 7.59-7.47 (m, 3H), 4.83 & 4.65 (d, J=5 Hz, 1H), 3.18-3.05 (2m, 1H), 1.71-1.20 (m, 2H), 1.05-0.97 (2xt, J=7.2 Hz, 3H).

Reference 36

(S)-2-Acetoxy-3-tert-butoxycarbonylamino-pentanoic acid

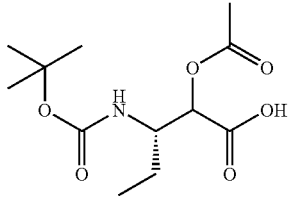

Pyridine (5 mL), 4-(dimethylamino)pyridine (0.01 g) and acetic anhydride (11 mmol, 1.12 g) are dissolved in dichloromethane (150 mL) and the resulting solution cooled to 0° C. (S)-3-tert-Butoxycarbonylamino-2-hydroxy-pentanoic acid (10 mmol, 2.33 g, A) is added at once and the resulting reaction mixture is stirred for 5 hours.

1M hydrochloric acid (250 mL) is added and the mixture transferred into a separating funnel. The phases are separated and the aqueous phase extracted three times with ethyl acetate (200 mL). The combined organic phases are washed twice with water (200 mL) and with brine (100 mL). The organic phase is dried with magnesium sulfate and the solvents evaporated under reduced pressure to give (S)-2-acetoxy-3-tert-butoxycarbonylamino-pentanoic acid (2.535 g, 92%).

MS: m/z=298 (M+Na+), 276 (M+H+)

Reference 37

Acetic acid (S)-2-tert-butoxycarbonylamino-1-[N'-(4-trifluoromethoxy-benzoyl)hydrazinocarbonyl]-butyl ester

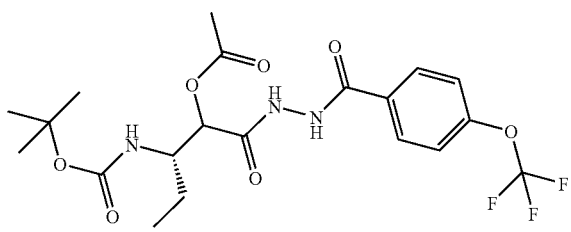

(S)-2-acetoxy-3-tert-butoxycarbonylamino-pentanoic acid (1.82 mmol, 0.5 g, A) is dissolved in 30 mL dichloromethane. N-Cyclohexylcarbodiimide-N'-methylpolystyrene (3.64 mmol, 1.92 g, B) is added and the resulting reaction mixture stirred for 2 min. 4-(trifluoromethoxy)benzoic acid hydrazide (1.65 mmol, 0.363 g, C) is added and the reaction mixture stirred over night. After 16 hours LC/MS analysis still showed hydrazide. Polystyrene methyl isocyanate (1.65 mmol, 1.15 g) is added and stirring continued for eight hours. The reaction mixture is filtered under suction and the filtrate concentrated under reduced pressure. To give acetic acid (S)-2-tert-butoxycarbonylamino-1-[N'-(4-trifluoromethoxy-benzoyl)hydrazinocarbonyl]-butyl ester as a foam (0.5 g, 64%). According to LC/MS still some hydrazide present. MS: m/z=500 (M+Na+), 478 (M+H+)

Reference 38

Acetic acid (S)-2-tert-butoxycarbonylamino-1-[5-(4-trifluoromethoxy-phenyl)-1,3,4-oxadiazol-2-yl]-butyl ester

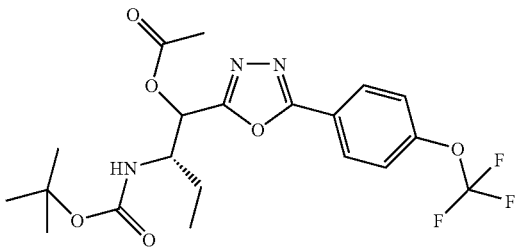

The acetic acid (S)-2-tert-butoxycarbonylamino-1-[N'-(4-trifluoromethoxy-benzoyl)-hydrazinocarbonyl]-butyl ester obtained above is split into 5 portions, which are separately reacted as follows:

acetic acid (S)-2-tert-butoxycarbonylamino-1-[N'-(4-trifluoromethoxy-benzoyl)-hydrazinocarbonyl]-butyl ester (0.21 mmol, 0.1 g) is dissolved in THF (5 mL) and the solution filled into a Smith Microwave synthesizer reaction vessel. 2-tert-Butylimino-2-diethylamino-1,3-dimethylperhydro-1,2,3-diazaphosphorine on polystyrene (1.05 mmol, 0.456 g, 2.3 mmol/g loading) and the p-Toluenesulfonic chloride (0.25 mmol, 0.048 g) are added and the reaction mixture heated at 150° C. for 10 min (fixed hold time) in the microwave synthesizer.

The combined reaction mixtures are filtered under suction and the resin washed with 300 mL ethyl acetate. The combined filtrates are concentrated under reduced pressure.

The crude product purified via flash chromatography (Biotage Horizon, 25M column, crude product loaded on caplet, 17 mL/min flow rate, 12 mL/fraction, 120 mL gradient from 0% ethyl acetate in heptane to 30% ethyl acetate in heptane, 240 mL 30% ethyl acetate in heptane, 60 mL gradient 30-50% ethyl acetate in heptane, 300 mL 50% ethyl acetate in heptane) to give acetic acid (S)-2-tert-butoxycarbonylarnino 1-[5-(4-trifluoromethoxy-phenyl)-1,3,4-oxadiazol-2-yl]-butyl ester (0.28 g, 58%)

MS: m/z=460 (M+H+)

Reference 39

((S)-1-{Hydroxy-[5-(4-trifluoromethoxy-phenyl)-1,3,4-oxadiazol-2-yl]-methyl}-propyl)-carbamic acid tert-butyl ester

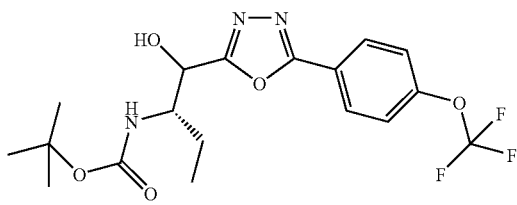

Acetic acid (S)-2-tert-butoxycarbonylamino-1-[5-(4-trifluoromethoxy-phenyl)-1,3,4-oxadiazol-2-yl]-butyl ester (0.61 mmol, 0.28 g) is dissolved in a mixture of THF (10 mL) and water (10 mL). Lithium hydroxide hydrate (1.22 mmol, 0.051 g) is added and the reaction mixture stirred for 2 h. The solvents are evaporated under reduced pressure and the residue transferred into a separating funnel with 300 mL ethyl acetate and 50 mL water. The phases are separated and the organic phase washed with brine (100 mL). The organic phase is then dried with magnesium sulfate. The solvent is evaporated under reduced pressure and dried under high vacuum to yield ((S)-1-{hydroxy-[5-(4-trifluoromethoxy-phenyl)-1,3,4-oxadiazol-2-yl]-methyl}-propyl)-carbamic acid tert-butyl ester as an oil (0.225 g, 89%) MS: m/z=440 (M+Na$^+$), 418 (M+H$^+$)

Reference 40

(S)-2-Amino-1-[5-(4-trifluoromethoxy-phenyl)-1,3,4-oxadiazol-2-yl]-butan-1-ol

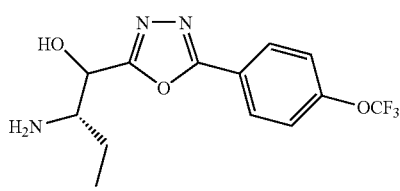

((S)-1-{hydroxy-[5-(4-trifluoromethoxy-phenyl)-1,3,4-oxadiazol-2-yl]-methyl}-propyl)-carbamic acid tert-butyl ester (0.54 mmol, 0.225 g) is dissolved in dichloromethane (9 mL) and treated with trifluoroacetic acid (1 mL). The reaction mixture is stirred for four hours. The solvents are evaporated under reduced pressure. The residue is re-dissolved in dichloromethane (20 mL) and Silicycle Triamine (5.4 mmol, 1.47 g) is added. The reaction mixture is stirred for 60 h (over the weekend). The reaction mixtures are filtered under suction and the solvents evaporated to give (S)-2-Amino-1-[5-(4-trifluoromethoxy-phenyl)-1,3,4-oxadiazol-2-yl]-butan-1-ol (0.164 g, 96%). MS: m/z=318 (M+H$^+$)

Reference 41

2-Cyclopropyl-[1,3,4]oxadiazole

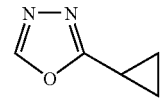

A mixture of cyclopropanecarboxylic acid methyl ester (10 g, 0.1 mol) and hydrazine hydrate (7.3 mL, 0.15 mol) is refluxed for 28 hr and cooled to room temperature. The mixture is evaporated under reduced pressure and then dried by azeotropic removal of the solvent with toluene. The residue is dissolved in dichloromethane and washed with saturated NaCl. The organic phase is dried over anhydrous MgSO$_4$, solvent evaporated under reduced pressure to give cyclopropanecarboxylic acid hydrazide (4.36 g, 44%)

A mixture of the Cyclopropanecarboxylic acid hydrazide (31.35 g, 0.31 mol), trimethyl orthoformate (300 mL) and p-toluenesulfonic acid monohydrate (200 mg) is heated under reflux overnight. Excess trimethyl orthoformate and methanol are removed by distillation. Vacuum distillation of the residue affords 2-Cyclopropyl-[1,3,4]oxadiazole (22 g, 64%).

$^1$H NMR (CDCl$_3$): δ 8.24(s, 1H), 2.2 (m, 1H), 1.15 (m, 4H). LCMS: 100%, 111 (MH$^+$).

Reference 42

{1-[(5-Cyclopropyl-[1,3,4]oxadiazol-2-yl)-hydroxy-methyl]-propyl}-carbamic acid tert-butyl ester A solution of 2-cyclopropyl-[1,3,4]oxadiazole (2.16 g, 19.6 mmol) in dry THF (100 mL) is cooled to −78° C. "BuLi (1.6M in hexanes, 12.3 mL, 19.6 mmol) is added dropwise. The reaction mixture is stirred at −78° C. for 40 min. MgBr$_2$.OEt$_2$ (5.0692 g, 19.6 mmol) is added. The reaction mixture is allowed to warm up to −45° C. and stirred at that temperature for 1.5 hr. A solution of (1-formyl-propyl)-carbamic acid tert-butyl ester (3.7 g, 19.6 mmol) in THF (40 mL) is added. The reaction mixture is allowed to warm up to −20° C. and stirred at that temperature for 3.5 hrs. The reaction mixture is quenched with a solution of saturated NH$_4$Cl solution and extracted with ethyl acetate. Combined organic extracts is washed with saturated NaCl solution and dried over MgSO$_4$. The solvent is evaporated under reduced pressure and the crude is purified by column chromatography eluting with ethyl acetate and heptane mixture to give {1-[(5-cyclopropyl-[1,3,4]oxadiazol-2-yl)-hydroxy-methyl]-propyl}-carbamic acid tert-butyl ester (2.83 g, 49%).

LCMS: 298 (MH$^+$).

Reference 43

(S)-2-Amino-1-(5-cyclopropyl-1,3,4-oxadiazol-2-yl)-butan-1-ol; compound with trifluoro-acetic acid

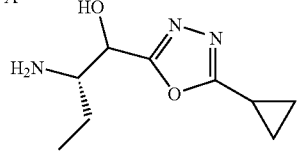

A mixture of {1-[(5-cyclopropyl-[1,3,4]oxadiazol-2-yl)-hydroxy-methyl]-propyl}-carbamic acid tert-butyl ester (2.83 g, 9.95 mmol), trifluoro acetic acid (5 mL) in dichloromethane (20 mL) is stirred at room temperature for 2 hrs and concentrated to dryness under reduced pressure to give (S)-2-amino-1-(5-cyclopropyl-1,3,4-oxadiazol-2-yl)-butan-1-ol: compound with trifluoro-acetic acid.

LCMS: 100% 198 (MH$^+$).

Reference 44

(S)-4,4-Difluoro-2-[(perhydro-1,4-oxazepine-4-carbonyl)-amino]-pentanoic acid methyl ester

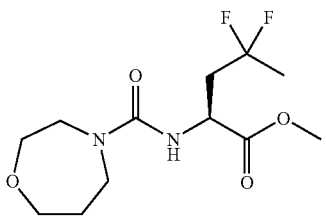

Triphosgene is dissolved in dichloromethane (10 mL) and to this is added, via syringe pump, a mixture of S-2-Amino-4,4-difluoro-pentanoic acid hydrochloride (1.00 g, 4.90 mmol) (see reference example 15), diisopropylethyl amine (1.88 mL, 10.80 mmol) dissolved in dichloromethane (10 mL) over the period of 1 h. After stirring for an additional 15 minutes a solution of homomorpholine hydrochloride (0.67 g, 4.90 mmol) and diisopropylethyl amine (1.90 mL, 10.90 mmol) in dichloromethane (10 mL) is added to the solution. The resulting solution is stirred at RT for 2 h. The solvent is evaporated and the residue diluted with ethyl acetate (100 mL) then washed with 1M KHSO$_3$ (2×10 mL), saturated NaHCO$_3$ and brine. The organics are dried (Na$_2$SO$_4$), filtered and concentrated to yield an oil. The crude material is purified on 20 g silica gel eluting with ethyl acetate:heptane gradient 50-100%. (S)-4,4-Difluoro-2-[(perhydro-1,4-oxazepine-4-carbonyl)-amino]-pentanoic acid methyl ester is obtained as a solid (0.40 g, 28%).

$^1$H NMR (CDCl$_3$) δ 5.12 (d, J=7.5 Hz, 1H), 4.72 (dd, J=12.0, 7.2 Hz, 1H), 3.75 (m, 7H), 3.55 (m, 4H), 2.45 (m, 2H), 1.98 (m, 2H), 1.66 (t, J=18.7 Hz, 3H).

LC/MS: 295, 100%, (M+H), 317 (M+Na)

Reference 45

(S)-4,4-Difluoro-2-[(perhydro-1,4-oxazepine-4-carbonyl)-amino]-pentanoic acid

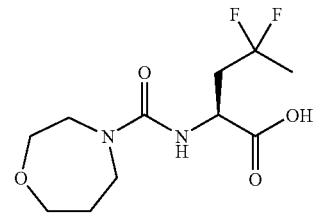

(S)-4,4-Difluoro-2-[(perhydro-1,4-oxazepine-4-carbonyl)-amino]-pentanoic acid methyl ester (0.38 g, 1.29 mmol) is dissolved in tetrahydrofuran/methanol (15 mL/10 mL) and lithium hydroxide (35 mg, 1.40 mmol) dissolved in water (5 mL) added. The reaction is stirred at RT for 18 h, and then the methanol/tetrahydrofuran is removed in vacuo. The residue is acidified with 6M hydrochloric acid (0.25 mL) and extracted with dichloromethane (3×20 mL), dried (Na$_2$SO$_4$), and concentrated to yield (S)-4,4-Difluoro-2-[(perhydro-1,4-oxazepine-4-carbonyl)-amino]-pentanoic acid as a solid (0.36 g, 99%).

$^1$H NMR (DMSO-d6) δ 12.6 (bs, 1H), 6.60 (d, 8.3 Hz, 1H), 4.30 (dd, J=14.5, 7.0 Hz, 1H), 3.57 (m, 4H), 3.43 (m, 4H), 2.38 (m, 2H), 1.77 (m, 2H), 1.61 (t, J=19.2 Hz, 3H).

LC/MS: 100% 281 (M+H)

Reference 46

(S)-4,4-Difluoro-2-[(perhydro-1,4-oxazepine-4-carbonyl)-amino]-pentanoic acid methyl ester

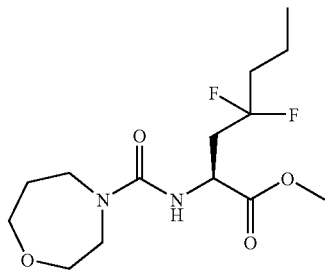

To a mixture of Sodium bicarbonate (5.25 g), p-nitro chloroformate (5.03 g, 25 mmol) in acetonitrile (130 mL) under nitrogen is added (S)-2-Amino-4,4-difluoro-heptanoic acid methyl ester hydrochloride (5.79 g, 0.025 mol) and stirred at room temperature for 5 hr. Homomorpholine hydrochloride (3.61 g, 26.25 mmol) and triethyl amine (12.5 mL) are added and the reaction stirred overnight at room temperature. Solvent evaporated off under reduced pressure, crude partitioned between water (150 mL) and ethyl acetate (200 mL). Organic layer separated, washed with K$_2$CO$_3$ solution (150 mL), HCl (150 mL) and brine (150 mL). Organic layer separated, dried (MgSO$_4$) and evaporated under reduced pressure. Crude purified by column chromatography eluting with v/v 1:1 to 8:2 ethyl acetate heptane followed by ethyl acetate to give (S)-4,4-Difluoro-2-[(perhydro-1,4-oxazepine4-carbonyl)-amino]-heptanoic acid methyl ester (4.8 g) as an oil.

LC/MS: 323 (M+H)

Reference 47

(S)-4,4-Difluoro-2-[(perhydro-1,4-oxazepine-4-carbonyl)-amino]-heptanoic acid

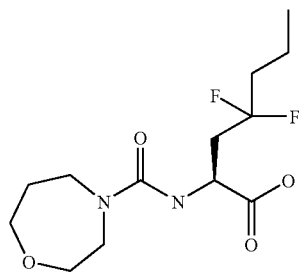

By proceeding in a similar manner to Reference Example 45 above but using (S)-4,4-Difluoro-2-[(perhydro-1,4-oxazepine-4-carbonyl)-amino]-heptanoic acid methyl ester there is prepared (S)4,4-Diflouro-2-[(perhydro-1,4-oxazepine-4-carbonyl)-amino]-heptanoic acid.

LC/MS: 309 (M+H)

Reference 48

(S)-2-Amino-1-(3-isopropyl-[1,2,4]oxadiazol-5-yl)-butan-1-ol

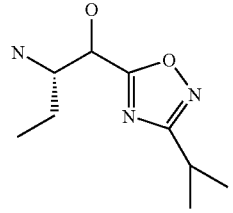

Similarly prepared according to the procedure for Reference Example 33.

LCMS: 200 (M+H)

Reference 49

{(S)-1-[(5-tert-Butyl-1,2,4-oxadiazol-3-yl)-hydroxy-methyl]-propyl}-carbamic acid tert butyl ester

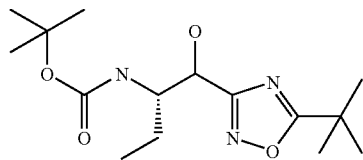

{(S)-1-[Hydroxy-(N-hydroxycarbamimidoyl)-methyl]-propyl}-carbamic acid tert-butyl ester (235 mg, 0.95 mmol) in diglyme (2 mL) is treated with trimethyl acetic anhydride (0.212 mL, 1.04 mmol) and the reaction mixture heated at 170° C. for 5 minutes in a Emrys Optimizer microwave from Personal Chemistry. The solvent is evaporated under high vacuum. The crude obtained is purified by flash chromatography eluting with a mixture of ethyl acetate and heptane (1:4) to give {(S)-1-[(5-tert-Butyl-1,2,4-oxadiazol-3-yl)-hydroxy-methyl]-propyl}-carbamic acid tert butyl ester as an oil (100 mg) (mixture of diastereoisomers).

$^1$H NMR (CDCl$_3$) δ: 4.92-4.69 (m, 2H), 4.05-3.85 (m, 1H), 3.57-3.41 & 3.32-3.15 (2xbs, 3H). 1.48 (m, 2H), 1.45 & 1.44 (2xs, 9H), 1.43 & 1.39 (2xs, 9H), 0.99 & 0.96 (2xt, J=7.5 Hz, 3H).

MS:314 (M+H).

Reference 50

(S)-2-Amino-1-(5-tert-butyl-1,2,4-oxadiazol-3-yl)-butan-1-ol

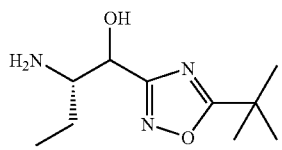

A solution of {(S)-1-[(5-tert-Butyl-1,2,4-oxadiazol-3-yl)-hydroxy-methyl]-propyl}-carbamic acid tert butyl ester (2.11 g, 6.72 mmol) in methylene chloride (20 mL) is treated with trifluoroacetic acid (5.18 mL, 67.25 mmol) and stirred at room temperature for 3 h. The solvent is evaporated under reduced pressure. The residue is dissolved in methylene chloride (100 mL) and treated with PS-trisamine from Argonaut Technologies (5.38 g, 20.18 mmol, 3.75 mmol/g loading) and the reaction stirred at room temperature for 4 h, filtered and the filtrate evaporated to give (S)-2-Amino-1-(5-tert-butyl-1, 2,4-oxadiazol-3-yl)-butan-1-ol as an oil (975 mg) (mixture of diastereoisomers).

$^1$H NMR (CDCl$_3$) δ: 4.73 & 4.58 (2xd, J=5 Hz, 1H), 3.12-3.00 (m, 1H), 2.64-2.31 (bs, 3H), 1.69-1.44 (m, 2H), 1.43 (s, 9H), 0.99 & 0.97 (2xt, J=7.5 Hz, 3H).

MS: 214 (M+H).

Reference 51

(S)-1-{[5-(4-Fluoro-phenyl)-1,2,4-oxadiazol-3-yl]-hydroxy-methyl}-propyl)-carbamic acid tert-butyl ester

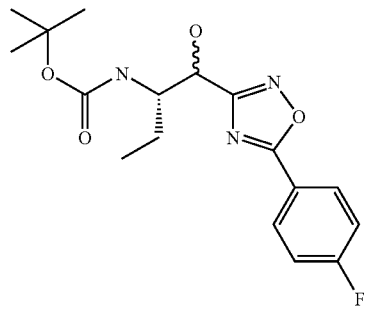

A suspension of 4-fluoro benzoic acid (1.70 g, 0.012 mol) and 1-(3-dimethylaminopropyl)-3-ethylcarbodiimide hydrochloride (2.12 g, 0.011 mol) in methylene chloride (80 mL) is treated with (S)-1-[Hydroxy-(N-hydroxycarbamimidoyl)-methyl]-propyl}-carbamic acid tert-butyl ester (3 g, 0.012 mol) and triethylamine (1.54 mL, 0.011 mol). The reaction is stirred at room temperature overnight. Then, it is diluted with 40 mL of methylene chloride, washed with saturated aqueous bicarbonate solution (30 mL), water (30 mL), brine (30 mL), dried over Na$_2$SO$_4$ and the solvent evaporated under reduced pressure. The residue is purified by flash chromatography eluting with a mixture of ethyl acetate and heptane (2:1) to give a solid (2.20 g)

$^1$H NMR (CDCl$_3$) δ: 8.10-7.95 (m, 2H), 7.16-7.00 (m, 2H), 5.43-5.24 (m, 2H), 5.22-5.05 (m, 1H), 5.01-4.85 (m, 1H), 4.50-4.39 (m, 1H), 3.80-3.60 (m, 1H), 1.90-1.78 (m, 2H), 1.40 (s, 90H), 0.98 (t, J=7.5 Hz, 3H).

MS: 370 (M+H).

240 mg of the solid (0.65 mmol) compound obtained above is taken in diglyme (5 mL) and heated at 160° C. in a microwave (Smith Creator, S00219) for 18 minutes. The solvent is evaporated under high vacuum. The crude obtained is purified by flash chromatography eluting with a mixture of ethyl acetate and heptane (1:4) to give (S)-1-{[5-(4-Fluoro-phenyl)-1,2,4-oxadiazol-3-yl]-hydroxy-methyl}-propyl)-carbamic acid tert-butyl ester as a solid (148 mg).

$^1$H NMR (CDCl$_3$) δ: 8.16-8.09 (m, 2H), 7.25-7.12 (m, 2H), 4.98-4.73 (m, 2H), 4.13-3.87 (m, 1H), 3.82-3.35 (m, 1H), 1.80-1.52 (m, 2H), 1.46 & 1.34 (2xs, 9H), 1.02 & 0.99 (2xt, J=7.5 Hz, 3H).

MS: 352 (M+H).

Reference 52

(S)-2-Amino-1-[5-(4-fluoro-phenyl)-1,2,4-oxadiazol-3-yl]-butan-1-ol

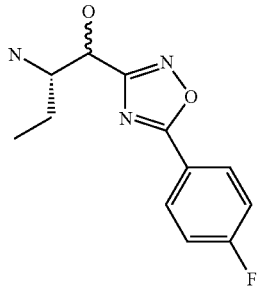

Similarly prepared according to Reference Example 50 above but using (S)-1-{[5-(4-Fluoro-phenyl)-1,2,4-oxadiazol-3-yl]-hydroxy-methyl}-propyl)-carbamic acid tert-butyl ester.

$^1$H NMR (CDCl$_3$) δ: 8.18-8.05 (m, 2H), 7.26-7.12 (m, 2H), 4.92 & 4.73 (2×d, J=5 Hz, 1H), 3.27-3.05 (m, 1H), 1.75-1.62 (m, 1H), 1.59-1.41 (m, 1H), 1.02 & 1.00 (2×t, J=7.5 Hz, 3H).
MS: 252 (M+H).

Reference 53

{(S)-1-[(5-Cyclopropyl-1,2,4-oxadiazol-3-yl)-hydroxy-methyl]-propyl}-carbamic acid tert-butyl ester

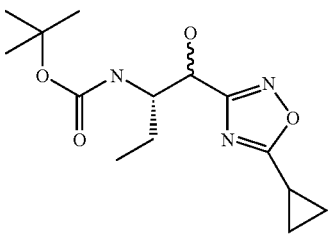

A suspention of (S)-1-[Hydroxy-(N-hydroxycarbamimidoyl)-methyl]-propyl}-carbamic acid tert-butyl ester (6.12 g, 24.78 mmol) in methylene chloride (150 mL) is treated with triethylamine (3.46 mL, 24.82 mmol) and then cooled to 0° C. Then cyclopropyl carbonyl chloride (2.25 mL, 24.79 mmol) is added dropwise. The reaction is stirred at room temperature for 1 h 45 min. and diluted with 150 mL of methylene chloride, washed with water (40 mL), saturated aqueous bicarbonate (20 mL), water (20 mL), dried over Na$_2$SO$_4$ and solvent evaporated under reduced pressure to give a solid (7.16 g). MS: 338 (M+Na).

A solution of the compound obtained above (7.45 g, 0.024 mol) in dioxane (150 mL) is heated at reflux for 15 h. The solvent is evaporated under reduced pressure and the residue is purified by flash chromatography eluting with a mixture of ethyl acetate and heptane to give (S)-1-[(5-Cyclopropyl-1,2, 4-oxadiazol-3-yl)-hydroxy-methyl]-propyl}-carbamic acid tert-butyl ester as a solid (5 g).

$^1$H NMR (CDCl$_3$) δ: 4.94-4.74 (m, 2H), 3.97 & 3.85 (2×m, 1H), 3.62 & 3.48 (2×bs, 1H), 2.19 (m, 1H), 1.72-1.42 (m, 2H), 1.44 & 1.39 (2×s, 9H), 1.26-1.18 (m, 4H), 0.98 & 0.95 (2×t, J=7.4 Hz, 3H).
MS: 298 (M+H).

Reference 54

(S)-2-Amino-1-(5-cyclopropyl-1,2,4-oxadiazol-3-yl)-butan-1-ol HCl salt

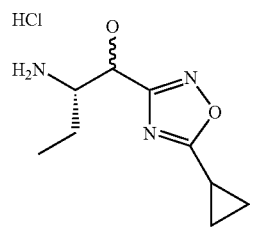

A solution of {(S)-1-[(5-Cyclopropyl-1,2,4-oxadiazol-3-yl)-hydroxy-methyl]-propyl}-carbamic acid tert-butyl ester (3.41 g, 0.011 mmol) in 4N HCl in dioxane (43 mL, 0.172 mmol) is stirred at room temperature for 2 h. Solvent evaporated under reduced pressure. Residue triturated with a mixture of ethyl acetate and ether. It is then filtered to give (S)-2-Amino-1-(5-cyclopropyl-1,2,4-oxadiazol-3-yl)-butan-1-ol HCl salt as a solid (2.47 g).

$^1$H NMR (CDCl$_3$) δ: 8.21 (bs, 2H), 5.37 & 5.14 (2×d, 1H), 3.88 & 3.73 (2×m, 1H), 2.21 (m, 1H), 1.92-1.50 (m, 2H), 1.24 (m, 4H), 1.08 & 1.06 (2×t, J=7.4 Hz, 3H).
MS: 198 (M+H).

Example 1

Morpholine-4-carboxylic acid {(S)-1-[(S)-1-(3-cyclopropyl-1,2,4-oxadiazole-5-carbonyl)-propylcarbamoyl]-3,3-difluoro-hexyl}-amide

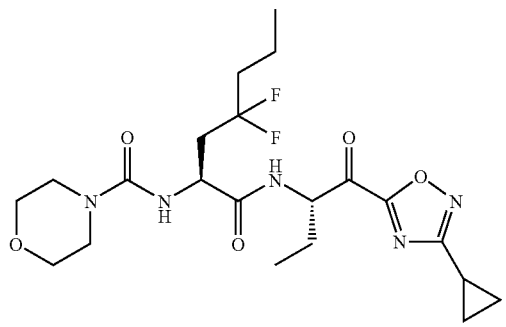

To a mixture of (S)-4,4-difluoro-2-[(morpholine-4-carbonyl)-amino]-heptanoic acid (104 mg, 0.35 mmol), (S)-2-amino-1-(3-cyclopropyl-1,2,4-oxadiazol-5-yl)-butan-1-ol hydrochloride (86.7 mg, 0.37 mmol) and diisopropyl amine (219 mg, 0.42 mmol) in dry dichloromethane (5 mL) is added PyBOP (113 mg, 0.87 mmol). The mixture is stirred at room temperature for 16 hr and the evaporated in vacuum. The residue is diluted with ethyl acetate (25 mL) and washed with saturated NaHCO$_3$ (30 mL), dilute HCl (30 mL), then saturated NaHCO$_3$ (30 mL). The organic layer is dried over magnesium sulfate and concentrated in vacuum. The residue is purified over 12 g silica gel, eluting with ethyl acetate: heptane (2:1 then 1:0) to afford morpholine-4-carboxylic acid (1-{1-[(3-cyclopropyl-[1,2,4]oxadiazol-5-yl)-hydroxy-methyl]-propylcarbamoyl}-3,3-difluoro-hexyl)-amide (146 mg, 88%) as a solid. LC/MS shows 2 isomers, total 100% M+1 474.

To a solution of morpholine-4-carboxylic acid (1-{1-[(3-cyclopropyl-[1,2,4]oxadiazol-5-yl)-hydroxy-methyl]-propylcarbamoyl}-3,3-difluoro-hexyl)-amide (145 mg, 0.31 mmol) in dry dichloromethane (3 mL) under N2 is added Dess-Martin periodinane (15% wt solution in dichloromethane, 1.73 g, 0.061 mmol). The reaction is stirred at room temperature for 2 hr, then quenched with a solution of Na$_2$S$_2$O$_3$ 193 mg, 1.22 mmol) in saturated NaHCO$_3$ (30 mL). The aqueous layer is extracted with dichloromethane (2×30 mL). The organic layers are dried over magnesium sulfate and concentrated in vacuum. The residue is purified over 12 g silica gel, eluted with ethyl acetate: heptane (1:1 then 2:1) to afford the desired ketone (119 mg, 81%) as a solid.

$^1$H NMR (CDCl$_3$): δ 7.4 (d, 7.0 Hz, 1H), 5.27 (m, 1H), 5.13 (d, J=6.9 Hz, 1H), 4.65 (dd, J=13.1, 6.9 Hz, 1H), 3.7 (m, 4H), 3.4 (m, 4H), 2.4 (m, 2H), 2.2 (m, 1H), 2.05 (m, 1H), 1.8 (m, 3H), 1.55 (m, 2H), 1.15 (m, 4H), 0.98 (t, J=7.4 Hz, 6H);

LC/MS: 28% 512 (M+H$_2$O+Na) and 68% 494 (M+Na).

Example 2

Morpholine-4-carboxylic acid {(S)-1-[(S)-1-(5-cyclopropyl-1,3,4-oxadiazole-2-carbonyl)-propylcarbamoyl]-3,3-difluoro-hexyl}-amide

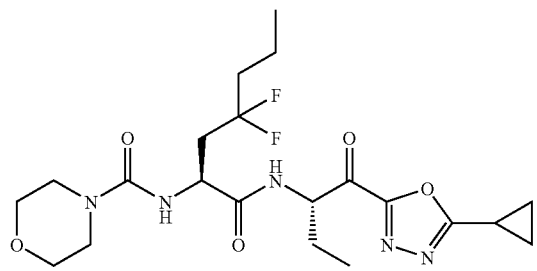

PyBOP (171.73 mg, 0.33 mmol), diisopropylethylamine (0.0575 mL, 0.33 mmol) and (S)-2-amino-1-(5-cyclopropyl-1,3,4-oxadiazol-2-yl)-butan-1-ol; compound with trifluoroacetic acid (0.30 mmol) are added to a solution of (S)-4,4-Difluoro-2-[(morpholine-4-carbonyl)-amino]-heptanoic acid (88.29 mg, 0.30 mmol) in dry methylene chloride (4 mL) and the reaction mixture is stirred overnight at room temperature. The reaction is quenched with aqueous sodium bicarbonate, extracted twice with methylene chloride, the organic extracts are dried over sodium sulfate and evaporated under reduced pressure. Column chromatography on silica eluting with a mixture of methylene chloride and ethyl acetate gives morpholine-4-carboxylic acid ((S)-1-{(S)-1-[(5-cyclopropyl-1,3,4-oxadiazol-2-yl)-hydroxy-methyl]-propylcarbamoyl-}3,3-difluoro-hexyl)-amide as a solid (87 mg). LC/MS 97%, 474 (M+1).

Dess-Martin Periodinane (15 wt % in DCM, 0.79 gm, 0.28 mmol) is added to a solution of morpholine-4-carboxylic acid ((S)-1-{(S)-1-[(5-cyclopropyl-1,3,4-oxadiazol-2-yl)-hydroxy-methyl]-propylcarbamoyl}-3,3-difluoro-hexyl)-amide (67 mg, 0.14 mmol) in dry methylene chloride (10 mL) and stirred at room temperature for 2.5 hours. The reaction is quenched with a solution of Na$_2$S$_2$O$_3$ (110.68 mg, 0.70 mmol) in aqueous NaHCO$_3$. The organic layer is separated and the aqueous extracted with dichloromethane. The organic extracts are dried over sodium sulfate and concentrated under reduced pressure. Column chromatography on silica eluting with a mixture of methylene chloride and ethyl acetate gives morpholine-4-carboxylic acid {(S)-1-[(S)-1-(5-cyclopropyl-1,3,4-oxadiazole-2-carbonyl)-propylcarbamoyl]-3,3-difluoro-hexyl}-amide as a powder (48 mg).

$^1$H NMR (CDCl$_3$): δ 7.52 (d, J=7.5 Hz, 1H), 5.34 (m, 1H), 5.18 (d, J=7.5 Hz, 1H), 4.65 (m, 1H), 3.72 (m, 4H), 3.40 (m, 4H), 2.50-2.22 (m, 3H), 2.18-2.08 (m, 1H), 1.96-1.78 (m, 3H), 1.60-1.45 (m, 2H), 1.30 (m, 4H), 0.98 (t+t, 6H).

LC/MS 95%, 472 (M+1).

Example 3

Morpholine-4-carboxylic acid ((S)-3,3-difluoro-1-{(S)-1-[5-(4-trifluoromethoxy-phenyl)-1,3,4-oxadiazole-2-carbonyl]-propylcarbamoyl}-hexyl)-amide

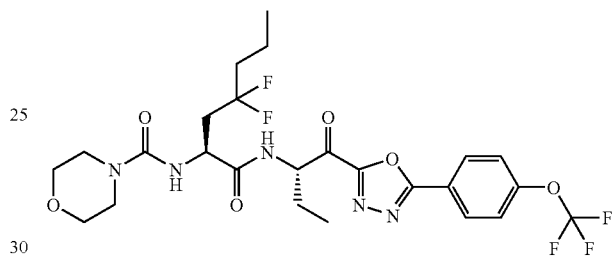

PyBOP (68.69 mg, 0.13 mmol), diisopropylethylamine (0.023 mL, 0.13 mmol) and (S)-2-Amino-1-[5-(4-trifluoromethoxy-phenyl)-1,3,4-oxadiazol-2-yl]-butan-1-ol (38.0 mg, 0.12 mmol) are added to a solution of (S)-4,4-Difluoro-2-[(morpholine-4-carbonyl)-amino]-heptanoic acid (34 mg, 0.12 mmol) in dry methylene chloride (4 mL) and the reaction mixture is stirred overnight at room temperature. The reaction is quenched with aqueous NaHCO$_3$, extracted twice with methylene chloride, the organic extracts are dried over Na2SO$_4$ and evaporated under reduced pressure. Column chromatography on silica eluting with a mixture of methylene chloride and ethyl acetate gives morpholine-4-carboxylic acid [(S)-3,3-difluoro-1-((S)-1-{hydroxy-[5-(4-trifluoromethoxy-phenyl)-1,3,4-oxadiazol-2-yl]-methyl}-propylcarbamoyl)-hexyl]-amide as a solid (61 mg). LC/MS 71%, M+1=594

Dess-Martin Periodinane (15 wt % in DCM, 0.58 gm, 0.21 mmol) is added to a solution of morpholine-4-carboxylic acid [(S)-3,3-difluoro-1-((S)-1-{hydroxy-[5-(4-trifluoromethoxy-phenyl)-1,3,4-oxadiazol-2-yl]-methyl}-propylcarbamoyl)-hexyl]-amide (61 mg, 0.10 mmol) in dry methylene chloride (8 mL) and stirred at room temperature for 3 hrs. The reaction is quenched with a solution of Na$_2$S$_2$O$_3$ (81.43 mg, 0.50 mmol) in aqueous NaHCO$_3$. The organic layer is separated and the aqueous extracted with dichloromethane. The organic extracts are dried over sodium sulfate and concentrated under reduced pressure. Column chromatography on silica eluting with a mixture of methylene chloride and ethyl acetate gives morpholine-4-carboxylic acid ((S)-3,3-difluoro-1-{(S)-1-[5-(4-trifluoromethoxy-phenyl)-1,3,4-oxadiazole-2-carbonyl]-propylcarbamoyl}-hexyl)-amide as a powder (39 mg).

$^1$H NMR (CDCl$_3$): δ 8.25 (d, J=7.5 Hz, 2H), 7.60 (d, J=7.5 Hz, 1H), 7.42 (d, J=7.5 Hz, 2H), 5.36 (m, 1H), 5.16 (d, J=7.5 Hz, 1H), 4.70 (m, 1H), 3.74 (m, 4H), 3.42 (m, 4H), 2.54-2.32

(m, 2H), 2.28-2.14 (m, 1H), 2.02-1.80 (m, 3H), 1.60-1.45 (m, 2H), 1.06 (t, J=7 Hz, 3H), 0.96 (t, J=7 Hz, 3H).
LC/MS: 96%, 592 (M+1).

Example 4

Morpholine-4-carboxylic acid {(S)-1-[(S)-1-(3-cyclopropyl-1,2,4-oxadiazole-5-carbonyl)-propylcarbamoyl]-3,3-difluoro-4-phenyl-butyl}-amide

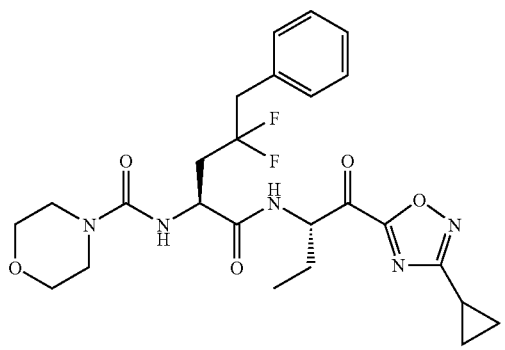

By proceeding in a similar manner to Example 1 above but using (S)-4,4-difluoro-2-[(morpholine-4-carbonyl)-amino]-5-phenyl-pentanoic acid and (S)-2-amino-1-(3-cyclopropyl-1,2,4-oxadiazol-5-yl)-butan-1-ol there is prepared morpholine-4-carboxylic acid {(S)-1-[(S)-1-(3-cyclopropyl-1,2,4-oxadiazole-5-carbonyl)-propylcarbamoyl]-3,3-difluoro-4-phenyl-butyl}-amide.

$^1$H NMR (CDCl$_3$): δ 7.3 (m, 6H), 5.25 (m, 1H), 5.08 (d, J=6.9 Hz, 1H), 4.7 (dd, J=12.8, 7.4 Hz, 1H), 3.7 (m, 4H), 3.4 (m, 4H), 3.2 (t, 16.8 Hz, 2H), 2.4-2.1 (m, 3H), 2.05 (m, 1H), 1.8 (m, 1H), 1.1 (m, 4H), 0.95 (t, J=7.5 Hz, 3H);
LC/MS: 35% 560 (M+H$_2$O+Na) and 65% 542 (M+Na).

Example 5

Morpholine-4-carboxylic acid {1-[1-(3-cyclopropyl-[1,2,4]oxadiazole-5-carbonyl)-propylcarbamoyl]-3,3-difluoro-5-methyl-hexyl}-amide

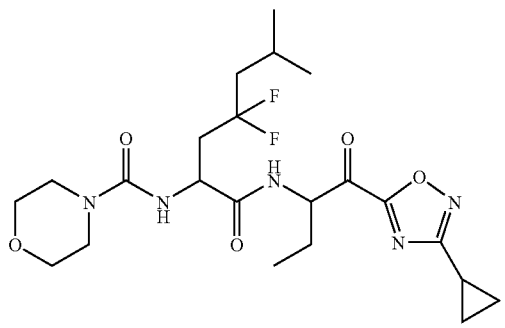

By proceeding in a similar manner to Example 1 above but using (S)-4,4-difluoro-6-methyl-2-[(morpholine-4-carbonyl)-amino]-heptanoic acid and (S)-2-amino-1-(3-cyclopropyl-1,2,4-oxadiazol-5-yl)-butan-1-ol there is prepared morpholine-4-carboxylic acid {1-[1-(3-cyclopropyl-[1,2,4]oxadiazole-5-carbonyl)-propylcarbamoyl]-3,3-difluoro-5-methyl-hexyl}-amide $^1$H NMR (CDCl$_3$): δ 7.6 (d, J=6.8 Hz, 1H), 5.2 (m, 2H), 4.66 (dd, J=13, 7.2 Hz, 1H), 3.7 (m, 4H), 3.4 (m, 4H), 2.3 (m, 2H), 2.2 (m, 1H), 2.05 (m, 1H), 1.95 (m, 1H), 1.8 (m, 3H), 1.1 (m, 4H), 0.97 (d, J=6.6 Hz, 6H), 0.96 (t, J=7.4 Hz, 3H);
LC/MS: 26%, 526 (M+H$_2$O+Na) and 74%, 508 (M+Na).

Example 6

Morpholine-4-carboxylic acid {(S)-1-[(S)-1-(3-cyclopropyl-1,2,4-oxadiazole-5-carbonyl)-propylcarbamoyl]-3,3-difluoro-butyl}-amide

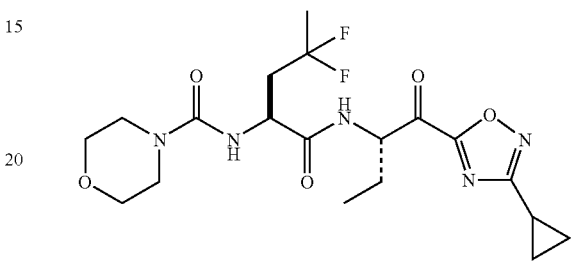

By proceeding in a similar manner to Example 1 above but using (S)-4,4-Difluoro-2-[(morpholine-4-carbonyl)-amino]-pentanoic acid and (S)-2-Amino-1-(3-cyclopropyl-1,2,4-oxadiazol-5-yl)-butan-1-ol there is prepared Morpholine-4-carboxylic acid {(S)-1-[(S)-1-(3-cyclopropyl-1,2,4-oxadiazole-5-carbonyl)-propylcarbamoyl]-3,3-difluoro-butyl}-amide $^1$H NMR (CDCl$_3$): δ 7.47 (d, J=6.8 Hz, 1H), 5.3 (m, 1H), 5.16 (d, J=6.9 Hz, 1H), 4.65 (dd, J=13, 7.4 Hz, 1H), 3.7 (m, 4H), 3.4 (m, 4H), 2.4 (m, 2H), 2.2 (m, 1H), 2.05 (m, 1H), 1.8 (m, 1H), 1.67 (t, 18.7 Hz, 3H), 1.1 (m, 4H), 0.97 (t, J=7.5 Hz, 3H);
LC/MS: 37% 484 (M+H$_2$O+Na) and 63% 484 (M+CH$_3$CN).

Example 7

Morpholine-4-carboxylic acid {(S)-3,3-difluoro-1-[(S)-1-(3-phenyl-1,2,4-oxadiazole-5-carbonyl)-propylcarbamoyl]-butyl}-amide

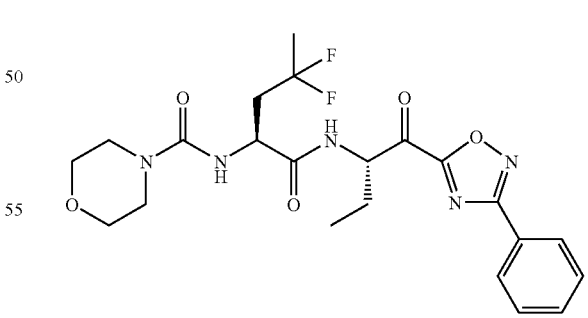

By proceeding in a similar manner to Example 1 above but using (S)-4,4-Difluoro-2-[(morpholine-4-carbonyl)-amino]-pentanoic acid and (S)-2-Amino-1-(3-phenyl-1,2,4-oxadiazol-5-yl)-butan-1-ol there is prepared Morpholine-4-carboxylic acid {(S)-3,3-difluoro-1-[(S)-1-(3-phenyl-1,2,4-oxadiazole-5-carbonyl)-propylcarbamoyl]-but}-amide as a solid.

¹H NMR (CDCl₃): δ 8.15 (dd, J=7.7, 1.5 Hz, 2H), 7.61 (d, J=6.4 Hz, 1H), 7.5 (m, 3H), 5.35 (m, 1H), 5.2 (d, J=6.9 Hz, 1H), 4.68 (dd, J=13.2, 7.8 Hz, 1H), 3.7 (m, 4H), 3.4 (m, 4H), 2.4 (m, 2H), 2.2 (m, 1H), 1.95 (m, 1H), 1.66 (t, 18.7 Hz, 3H), 1.03 (t, J=7.5 Hz, 3H);

LC/MS: 37% 520 (M+H₂O+Na) and 63% 502 (M+Na).

Example 8

Morpholine-4-carboxylic acid {(S)-3,3-difluoro-1-[(S)-1-(5-phenyl-1,2,4-oxadiazole-3-carbonyl)-propylcarbamoyl]-butyl}-amide

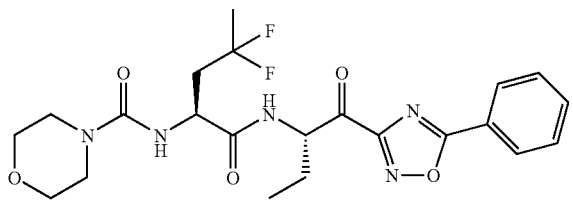

By proceeding in a similar manner to Example 1 above but using (S)-4,4-Difluoro-2-[(morpholine-4-carbonyl)-amino]-pentanoic acid and (S)-2-Amino-1-(5-phenyl-[1,2,4]oxadiazol-3-yl)-butan-1-ol there is prepared Morpholine-4-carboxylic acid {(S)-3,3-difluoro-1-[(S)-1-(5-phenyl-1,2,4-oxadiazole-3-carbonyl)-propylcarbamoyl]-butyl}-amide ¹H NMR (CDCl₃): δ 8.2 (d, J=7.1 Hz, 2H), 7.65 (d, J=7.4 Hz, 1H), 7.55 (m, 3H), 5.4 (dd, J=12.2, 7 Hz, 1H), 5.3 (d, J=7.4 Hz, 1H), 4.7 (dd, J=13, 7.3 Hz, 1H), 3.7 (m, 4H), 3.4 (m, 4H), 2.4 (m, 2H), 2.1 (m, 1H), 1.9 (m, 1H), 1.67 (t, 18.7 Hz, 3H), 1.0 (t, J=7.4 Hz, 3H);

LC/MS: 6% 520 (M+H₂O+Na) and 94% 502 (M+Na).

Example 9

Morpholine-4-carboxylic acid {1-[1-(5-cyclopropyl-[1,3,4]oxadiazole-2-carbonyl)-propylcarbamoyl]-3,3-difluoro-phenyl-butyl}-amide

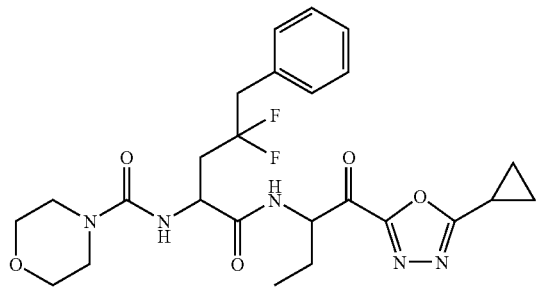

By proceeding in a similar manner to Example 1 above but using (S)-4,4-difluoro-2-[(morpholine-4-carbonyl)-amino]-5-phenyl-pentanoic acid and (S)-2-amino-1-(5-cyclopropyl-1,3,4-oxadiazol-2-yl)-butan-1-ol Trifluoro acetic acid salt, there is prepared morpholine-4-carboxylic acid {1-[1-(5-cyclopropyl-[1,3,4]oxadiazole-2-carbonyl)-propylcarbamoyl]-3,3-difluoro-4-phenyl-butyl}-amide.

¹H NMR (CDCl₃): δ 7.3 (m, 6H), 5.27 (m, 1H), 5.0 (d, J=7.0 Hz, 1H major), 4.95 (d, J=7.3 Hz, 1H minor), 4.7 (m, 1H), 3.7 (m, 4H), 3.4 (m, 4H), 3.2 (t, 16.3 Hz, 2H), 2.4-2.2 (m, 3H), 2.05 (m, 1H), 1.8 (m, 1H), 1.2 (m, 4H), 0.95 (t, J=7.5 Hz, 3H);

LC/MS: 12% 560 (M+H₂O+Na) and 83% 542 (M+Na).

Example 10

Morpholine-4-carboxylic acid {3,3-difluoro-1-[1-(5-isopropyl-isoxazole-3-carbonyl)-propylcarbamoyl]-hexyl}-amide

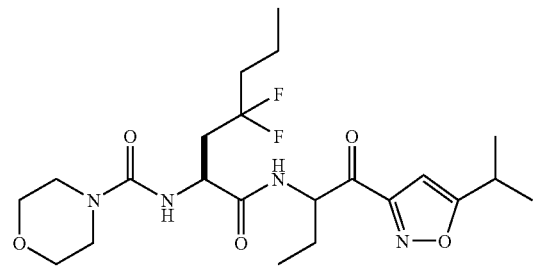

By proceeding in a similar manner to Example 1 above but using 2-amino-1-(5-isopropyl-isoxazol-3-yl)-butan-1-ol hydrochloride instead of (S)-2-amino-1-(3-cyclopropyl-1,2,4-oxadiazol-5-yl)-butan-1-ol hydrochloride there is prepared morpholine-4-carboxylic acid {3,3-difluoro-1-[1-(5-isopropyl-isoxazol-3-carbonyl)-propylcarbamoyl]-hexyl}-amide as a solid.

¹H NMR (CDCl₃): δ ca 2:1 mixture of isomers 7.4 (b, 1H), 6.37 (s, 1H), 5.4 (m, 1H), 5.26 (d, J=6.9 Hz, 1H major), 5.2 (d, J=7.2 Hz, 1H minor), 4.7 (m, 1H), 3.7 (m, 4H), 3.4 (m, 4H), 3.15 (m, 1H), 2.4 (m, 2H), 2.1 (m, 1H), 1.8 (m, 4H), 1.5 (m, 1H), 1.35 (d, J=7.0 Hz, 6H), 0.95 (m, 6H);

LC/MS: 100% 473 (M+1).

Example 11

Morpholine-4-carboxylic acid ((S)-3,3difluoro-1-{(S)-1-[5-(5-methyl-isoxazol-3-yl)-oxazole-2-carbonyl]-propylcarbamoyl}-hexyl)-amide

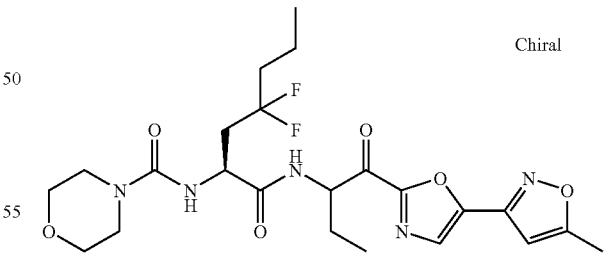

By proceeding in a similar manner to Example 3 above but using (S)-4,4-difluoro-2-[(morpholine-4-carbonyl)-amino]-heptanoic acid and (S)-2-amino-1-[5-(5-methyl-isoxazol-3-yl)-oxazol-2-yl]-butan-1-ol; hydrochloride there is prepared Morpholine-4-carboxylic acid ((S)-3,3-difluoro-1-{1-[5-(5-methyl-isoxazol-3-yl)-oxazole-2-carbonyl]-propylcarbamoyl}-hexyl)-amide as a solid.

¹H NMR (CDCl₃): δ 7.78 (s, 1H), 7.40 (m, 1H), 6.44 (s, 1H), 5.48 (m, 1H), 5.22-5.10 (m, 1H), 4.68 (m, 1H), 3.72 (m,

4H), 3.40 (m, 4H), 2.54 (s, 3H), 2.50-2.30 (m, 2H), 2.22-2.08 (m, 1H), 1.94-1.78 (m, 3H), 1.60-1.46 (m, 2H), 1.08-0.94 (2×t, 6H).

LC/MS: 99%, 512 (M+1).

Example 12

Morpholine-4-carboxylic acid {(S)-3,3-difluoro-1-[(S)-1-(oxazole-2-carbonyl)-propylcarbamoyl]-4-phenyl-butyl}-amide

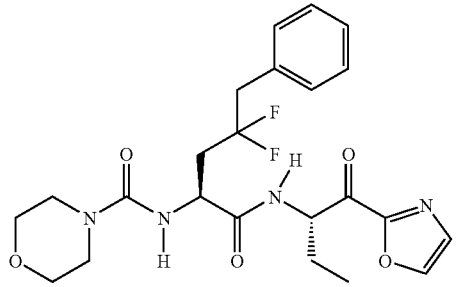

By proceeding in a similar manner to Example 2 above but using (S)-4,4-difluoro-2-[(morpholine-4-carbonyl)-amino]-5-phenyl-pentanoic acid and (S)-2-amino-1-oxazol-2-yl-butan-1-ol hydrochloride there is prepared morpholine-4-carboxylic acid {(S)-3,3-difluoro-1-[(S)-1-(oxazole-2-carbonyl)-propylcarbamoyl]4-phenyl-butyl}-amide $^1$H NMR (CDCl$_3$): δ 7.86 (s, 1H), 7.37 (s, 1H), 7.30 (m, 5H), 7.24 (m, 1H), 5.45 (m, 1H), 5.08 (d, J=9 Hz, 1H), 4.70 (m, 1H), 3.72 (m, 4H), 3.38 (m, 4H), 3.22 (t, J=17 Hz, 2H), 2.35 (m, 2H), 2.12 (m, 1H), 1.85 (m, 1H), 0.95 (t, J=9 Hz, 3H);

LC/MS: 97%, 479 (M+1).

Example 13

Morpholine-4-carboxylic acid {(S)-3,3-difluoro-4-phenyl-1-[(S)-1-(5-thiophen-2-yl-oxazole-2-carbonyl)-propylcarbamoyl]-butyl}-amide

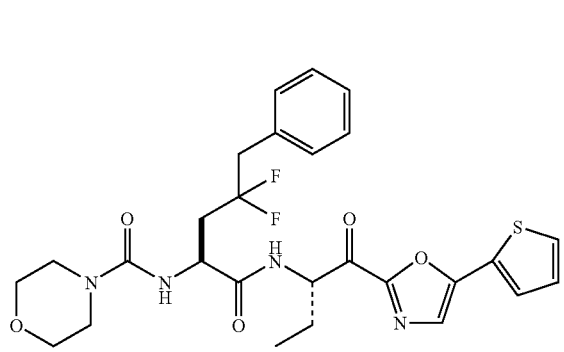

By proceeding in a similar manner to Example 1 above but using (S)-4,4-difluoro-2-[(morpholine-4-carbonyl)-amino]-5-phenyl-pentanoic acid and (S)-2-amino-1-(5-thiophen-2-yl-oxazol-2-yl)-butan-1-ol hydrochloride there is prepared morpholine-4-carboxylic acid {(S)-3,3-difluoro-4-phenyl-1-[(S)-1-(5-thiophen-2-yl-oxazole-2-carbonyl)-propylcarbamoyl]-butyl}-amide $^1$H NMR (CDCl$_3$): δ 7.53 (dd, J=3.6, 1 Hz, 1H), 7.48 (dd, J=5, 1 Hz, 1H), 7.4 (s, 1H), 7.3 (m, 6H), 7.15 (dd, J=5, 3.6 Hz, 1H), 5.4 (m, 1H), 5.15 (d, J=7.1 Hz, 1H), 4.7 (dd, J=13, 7.4 Hz, 1H), 3.7 (m, 4H), 3.4 (m, 4H), 3.2 (t, 16.7 Hz, 2H), 2.4 (m, 2H), 2.1 (m, 1H), 1.8 (m, 1H), 0.96 (t, J=7.5 Hz, 3H);

LC/MS: 100% 561 (M+1).

Example 14

Morpholine-4-carboxylic acid {(S)-1-[(s)-1-(benzoxazole-2-carbonyl)-butylcarbamoyl]-3,3-difluoro-4-phenyl-butyl}-amide

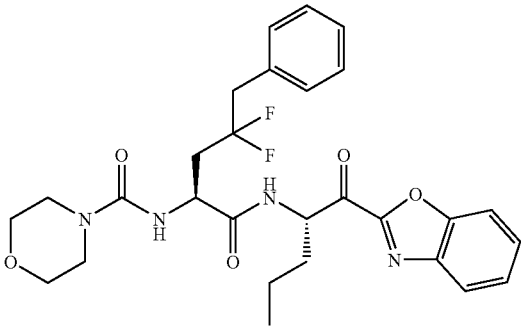

By proceeding in a similar manner to Example 1 above but using (S)-4,4-difluoro-2-[(morpholine-4-carbonyl)-amino]-5-phenyl-pentanoic acid and (S)-2-amino-1-benzoxazol-2-yl-pentan-1-ol there is prepared morpholine-4-carboxylic acid {(S)-1-[(S)-1-(benzoxazole-2-carbonyl)-butylcarbamoyl]-3,3-difluoro-4-phenyl-butyl}-amide.

$^1$H NMR (CDCl$_3$): δ 7.9 (d, J=8.0 Hz, 1H), 7.66 (d, J=8 Hz, 1H), 7.56 (t, J=7.2 Hz, 1H), 7.47 (t, J=8 Hz, 1H), 7.2 (m, 6H), 5.6 (m, 1H), 5.05 (d, J=7 Hz, 1H), 4.71 (dd, J=12.8, 7.4 Hz, 1H), 3.7 (m, 4H), 3.35 (m, 4H), 3.18 (t, J=16.8 Hz, 2H), 2.3 (m, 2H), 2.1 (m, 1H), 1.8 (m, 1H), 1.4 (m, 2H), 0.94 (t, J=7.3 Hz, 3H);

LC/MS: 100% 543 (M+1).

Example 15

Morpholine-4-carboxylic acid [1-(2-benzooxazol-2-yl-1-methoxymethyl-2-oxo-ethylcarbamoyl)-3,3-difluoro-4-phenyl-butyl]-amide

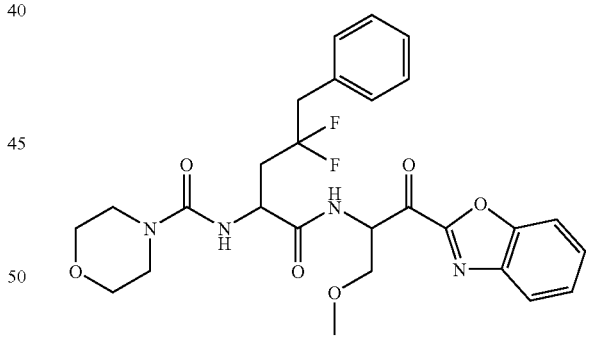

By proceeding in a similar manner to Example 1 above but using (S)-4,4-difluoro-2-[(morpholine-4-carbonyl)-amino]-5-phenyl-pentanoic acid and (S)-2-amino-1-benzooxazol-2-yl-3-methoxy-propan-1-ol there is prepared morpholine-4-carboxylic acid [1-(2-benzooxazol-2-yl-1-methoxymethyl-2-oxo-ethylcarbamoyl)-3,3-difluoro-4-phenyl-butyl]-amide.

$^1$H NMR (CDCl$_3$): δ 7.9 (d, J=7.7 Hz, 1H), 7.67 (d, J=8 Hz, 1H), 7.56 (t, J=8 Hz, 1H), 7.48 (t, J=8 Hz, 1H), 7.2 (m, 6H), 5.7 (m, 1H), 5.1 (d, J=7 Hz, 1H major), 5.05 (d, J=7.3 Hz, 1H minor), 4.8 (m, 1H), 4.26 (dd, J=9.7, 3.5 Hz, 1H), 3.8 (m, 1H), 3.7 (m, 4H), 3.35 (m, 4H), 3.27 (s, 3H), 3.22 (t, J=16.2 Hz, 2H), 2.4 (m, 2H);

LC/MS: 94% 545 (M+1).

Example 16

Morpholine-4-carboxylic acid {(S)-1-[(S)-1-(benzoxazole-2-carbonyl)-1-methyl-butylcarbamoyl]-3,3-difluoro-4-phenyl-butyl}-amide

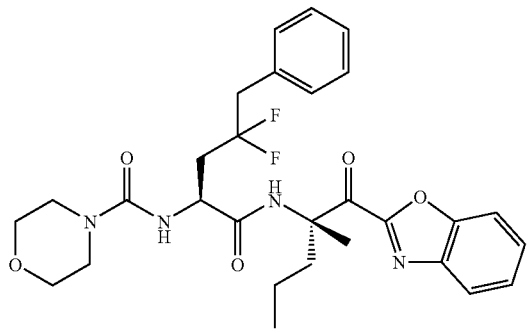

A mixture of (S)-2-amino-1-benzoxazol-2-yl-2-methyl-pentan-1-one hydrochloride (80.6 mg, 0.3 mmol), (S)-4,4-difluoro-2-[(morpholine-4-carbonyl)-amino]-5-phenyl-pentanoic acid (0.102 mg, 0.3 mmol), EDCI (69 mg, 0.36 mmol), HOBT (48.6 mg, 0.36 mmol) and Diisopropyl ethylamine (0.2 mL) in DMF is stirred at room temperature overnight. The reaction mixture is diluted with ethyl acetate, washed with cold 1N HCl, saturated NaHCO₃ and then saturated NaCl solution. The organic phase is dried over magnesium sulfate and solvent evaporated under reduced pressure to give the crude product. Purification by Silica gel column chromatography, eluting with ethyl acetate and heptane mixture gives morpholine-4-carboxylic acid {(S)-1-[(S)-1-(benzoxazole-2-carbonyl)-1-methyl-butylcarbamoyl]-3,3-difluoro-4-phenyl-butyl}-amide (82%).

¹H NMR (CDCl₃): δ 7.8 (d, J=7.8.0 Hz, 1H), 7.64 (d, J=7.8 Hz, 1H), 7.53 (dt, J=7.2, 1.2 Hz, 1H), 7.43 (dt, J=8, 1.2 Hz, 1H), 7.2 (m, 6H), 4.9 (d, J=7.3 Hz, 1H), 4.65 (m, 1H), 3.7 (m, 4H), 3.3 (m, 4H), 3.1 (t, J=16.8 Hz, 2H), 2.2 (m, 3H), 2.1 (m, 1H), 1.74 (s, 3H), 1.25 (m, 2H), 0.9 (t, J=7.3 Hz, 3H);
LC/MS: 100% 557 (M+1).

Example 17

Morpholine-4-carboxylic acid [(S)-1-((S)-1-cyano-3-phenyl-propylcarbamoyl)-3,3-difluoro-4-phenyl-butyl]-amide

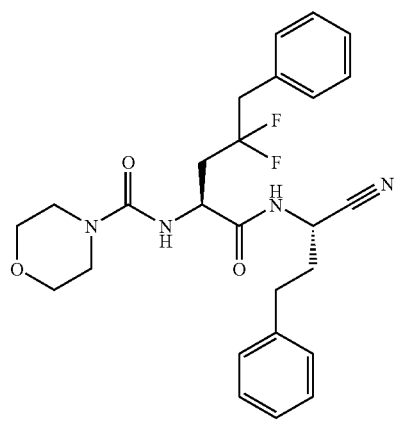

Proceeding according to the PyBOP coupling method given for example 1, but using (S)-4,4-difluoro-2-[(morpholine-4-carbonyl)-amino]-5-phenyl-pentanoic acid and (S)-2-amino-4-phenyl-butyronitrile hydrochloride, there is prepared, morpholine-4-carboxylic acid [(S)-1-((S)-1-cyano-3-phenyl-propylcarbamoyl)-3,3-difluoro-4-phenyl-butyl]-amide.

¹H NMR (CDCl₃): δ 7.9 (d, J=7.6 Hz, 1H), 7.2 (m, 10H), 5.1 (d, J=7.3 Hz, 1H), 4.6 (m, 2H), 3.6 (m, 4H), 3.3 (m, 4H), 3.2 (t, J=16.5 Hz, 2H), 2.74 (t, J=7.2 H, 2H), 2.3 (m, 2H), 2.1 (m, 2H);
LC/MS: 100% 485 (M+1).

Example 18

Morpholine-4-carboxylic acid [(S)-1-(cyanomethyl-carbamoyl)-3,3-difluoro-4-phenyl-butyl]-amide

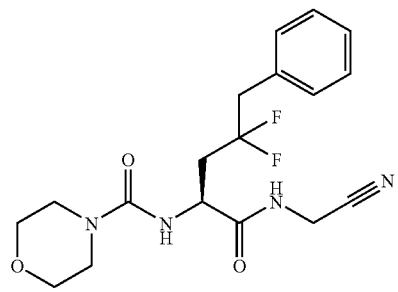

Proceeding according to the PyBOP coupling method given for Example 1, but using (S)-4,4-difluoro-2-[(morpholine-4-carbonyl)-amino]-5-phenyl-pentanoic acid and amino-acetonitrile hydrochloride, there is prepared, morpholine-4-carboxylic acid [(S)-1-(cyanomethyl-carbamoyl)-3,3-difluoro-4-phenyl-butyl]-amide.

¹H NMR (CDCl₃): δ 7.95 (b, 1H), 7.3 (m, 5H), 5.25 (d, J=7.0 Hz, 1H), 4.7 (dd, J=12.7, 7.2 Hz, 1H), 4.1 (m, 2H), 3.7 (m, 4H), 3.35 (m, 4H), 3.2 (t, J=16.3 Hz, 2H), 2.4 (m, 2H);
LC/MS: 83% 403 (M+Na).

Example 19

Morpholine-4-carboxylic acid [(S)-3,3-difluoro-1-((S)-1-formyl-1-methyl-butylcarbamoyl)-4-phenyl-butyl]-amide

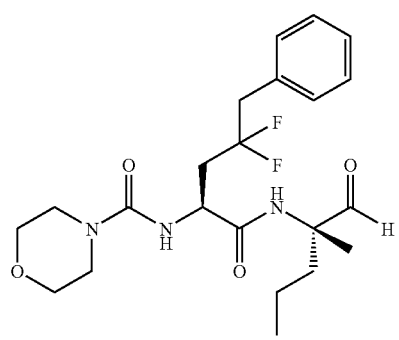

A mixture of (S)-2-amino-2-methyl-pentan-1-ol hydrochloride (104.4 mg, 0.67 mmol), (S)-4,4-difluoro-2-[(morpholine-4-carbonyl)-amino]-5-phenyl-pentanoic acid (231 mg, 0.67 mmol), EDCI (154 mg, 0.8 mmol), HOBT (108 mg, 0.8 mmol) and Diisopropyl ethylamine (0.23 mL) in DMF (2 mL) is stirred at room temperature overnight. The reaction mixture is diluted with ethyl acetate, washed with cold 1N HCl, saturated NaHCO$_3$ and then saturated NaCl solution. The organic phase is dried over MgSO$_4$ and solvent evaporated under reduced pressure to give the crude product. Purification by Silica gel column chromatography, eluting with ethyl acetate and heptane mixture gives morpholine-4-carboxylic acid [(S)-3,3-difluoro-1-((S)-1-hydroxymethyl-1-methyl-butylcarbamoyl)-4-phenyl-butyl]-amide (223 mg, 75%).

A mixture of Morpholine-4-carboxylic acid [(S)-3,3-difluoro-1-((S)-1-hydroxymethyl-1-methyl-butylcarbamoyl)-4-phenyl-butyl]-amide (217 mg) and Dess-Martin Periodinane (15% in DCM, 2 eq.) in DCM (5 mL) is stirred at room temperature for 3 hrs and quenched with a solution of sodium thiosulfate in saturated NaHCO$_3$. The product is extracted with ethyl acetate and washed with saturated NaCl solution. Organic phase is dried over anhydrous MgSO$_4$, solvent evaporated under reduced pressure. Purification by silica gel chromatography eluting with ethyl acetate-heptane mixture gives Morpholine-4-carboxylic acid [(S)-3,3-difluoro-1-((S)-1-formyl-1-methyl-butylcarbamoyl)-4-phenyl-butyl]-amide (83 mg, 38%).

$^1$H NMR (CDCl$_3$): δ 9.3 (s, 1H), 7.2 (m, 5H), 7.0 (s, 1H), 5.0 (d, J=7 Hz, 1H), 4.6 (dd, J=13, 7.3 Hz, 1H), 3.7 (m, 4H), 3.4 (m, 4H), 3.2 (t, J=16.5 Hz, 2H), 2.3 (m, 2H), 1.9 (m, 1H), 1.65 (m, 1H), 1.35 (s, 3H), 1.2 (m, 2H), 0.9 (t, J=7.3 Hz, 3H); LC/MS: 100% 440. (M+1)

Example 20

Perhydro-1,4-oxazepine-4-carboxylic acid {(S)-1-[(S)-1-(3-cyclopropyl-1,2,4-oxadiazole-5-carbonyl)-propylcarbamoyl]-3,3-difluoro-butyl}-amide

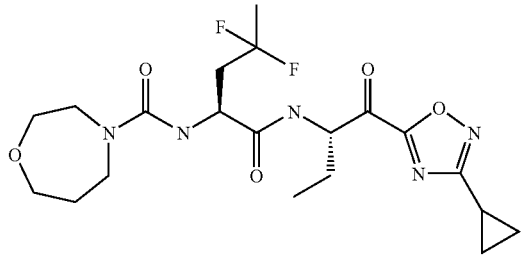

To a mixture of (S)-4,4-Difluoro-2-[(perhydro-1,4-oxazepine-4-carbonyl)-amino]-pentanoic acid (97 mg, 0.35 mmol), (S)-2-Amino-1-(3-cyclopropyl-1,2,4-oxadiazol-5-yl)-butan-1-ol hydrochloride (83 mg, 0.36 mmol) and diisopropylethyl amine (121 µL, 0.70 mmol) in dry dichloromethane (12 mL) is added 1-(3-Dimethylaminopropyl)-3-ethylcarbodiimide hydrochloride (66 mg, 0.35 mmol) and 1-hydroxybenzotriazole hydrate (47 mg, 0.35 mmol). The mixture is stirred at room temperature for 16 hr then is diluted with dichloromethane (20 mL) and washed with dilute HCl (30 mL), then saturated NaHCO$_3$ (30 mL). The organic layer is dried (Na$_2$SO$_4$) and concentrated in vacuum. The residue is purified over 12 g silica gel, eluting with ethyl acetate: heptane (gradient 50-100%) to afford Perhydro-1,4-oxazepine-4-carboxylic acid ((S)-1-{(S)-1-[(3-cyclopropyl-1,2,4-oxadiazol-5-yl)-hydroxy-methyl]-propylcarbamoyl}-3,3-difluoro-butyl)-amide (120 mg, 75%) as a glassy solid. LC/MS 100% 460 (M+H).

To a solution of Perhydro-1,4-oxazepine-4-carboxylic acid ((S)-1-{(S)-1-[(3-cyclopropyl-1,2,4-oxadiazol-5-yl)-hydroxy-methyl]-propylcarbamoyl}-3,3-difluoro-butyl)-amide (110 mg, 0.24 mmol) in dry dichloromethane (20 mL) under N$_2$ is added Dess-Martin periodinane (143 mg, 0.34 mmol). The reaction is stirred at RT for 2 hr, and then dichloromethane (20 mL) is added. The reaction is quenched with a solution of Na$_2$S$_2$O$_3$ (0.26M, 2 mL) and washed with saturated NaHCO$_3$ (20 mL). The aqueous layer is extracted with dichloromethane (2×30 mL). The organic layers are dried (Na$_2$SO$_4$) and concentrated in vacuum. The residue is purified over 12 g silica gel, eluted with ethyl acetate: heptane (gradient 50-100%) to afford Perhydro-1,4-oxazepine-4-carboxylic acid {(S)-1-[(S)-1-(3-cyclopropyl-1,2,4-oxadiazole-5-carbonyl)-propylcarbamoyl]-3,3-difluoro-butyl}-amide (82 mg, 75%) as a solid.

$^1$H NMR (CDCl$_3$) δ 7.52 (d, 6.2H), 5.28 (m, 1H), 5.05 (d, J=7 Hz, 1H), 4.66 (m, 1H), 3.78 (m, 4H), 3.59 (m, 4H), 2.42 (m, 2H), 2.23 (m, 1H), 2.07 (m, 1H), 1.98 (m, 1H0, 1.85 (m, 1H), 1.69 (t, J=18.8 Hz, 3H), 1.15 (m, 4H), 0.98 (t, J=7.5 Hz, 3H); LC/MS: 97% 458 (M+H).

Example 21

Perhydro-1,4-oxazepine-4-carboxylic acid {(S)-1-[(S)-1-(3-cyclopropyl-1,2,4-oxadiazole-5-carbonyl)-propylcarbamoyl]-3,3-difluoro-hexyl}-amide

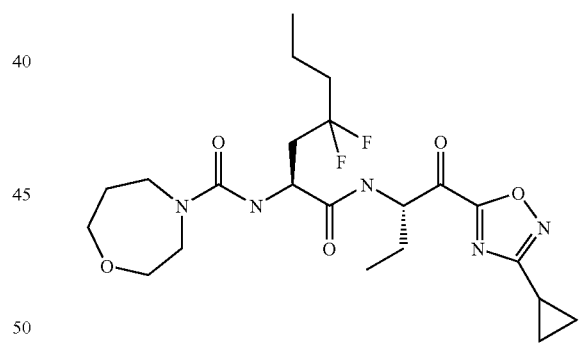

By proceeding in a similar manner Example 20 above but using (S)-4,4-Difluoro-2-[(perhydro-1,4-oxazepine-4-carbonyl)-amino]-heptanoic acid and (S)-2-amino-1-(3-cyclopropyl-1,2,4-oxadiazol-5-yl)-butan-1-ol hydrochloride there is prepared Perhydro-1,4-oxazepine-4-carboxylic acid {(S)-1-[(S)-1-(3-cyclopropyl-1,2,4-oxadiazole-5-carbonyl)-propylcarbamoyl]-3,3-difluoro-hexyl}-amide (98 mg, 65%) as a solid.

$^1$H NMR (CDCl3) δ 7.6 (d, J=7.5 Hz, 1H), 5.25 (m, 1H), 5.10 (d, J=7.5 Hz, 1H), 4.65 (dd, J=14, J=7.5 Hz, 1H), 3.75 (m, 6H), 3.55 (m, 4H), 2.4 (m, 2H), 2.2 (m, 2H), 1.95 (m, 1H), 1.8 (m, 3H), 1.55 (m, 2H), 1.10 (m, 4H), 0.95 (t, J=7.5 Hz, 6H);

LC/MS: 70% 486 (M+1) and 30% 504 (M+1+H2O).

Example 22

Morpholine-4-carboxylic acid {(S)-1-[(S)-1-(3-isopropyl-1,2,4-oxadiazole-5-carbonyl)-propylcarbamoyl]-3,3-difluoro-hexyl}-amide

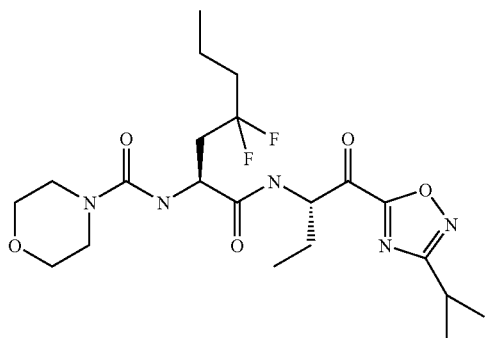

By proceeding in a similar manner to Example 20 above but using (S)-4,4-Difluoro-2-[(morpholine-4-carbonyl)-amino]-heptanoic acid and (S)-2-amino-1-(3-isopropyl-1,2,4-oxadiazol-5-yl)-butan-1-ol there is prepared, Morpholine-4-carboxylic acid {(S)-1-[(S)-1-(3-isopropyl-1,2,4-oxadiazole-5-carbonyl)-propylcarbamoyl]-3,3-difluoro-hexyl}-amide (122 mg, 71%) as a solid.

1H NMR (CDCl3) δ 7.5 (d, J=7.0 Hz, 1H), 5.3 (m,1H), 5.25 (d, J=7.0 Hz, 1H), 4.65 (dd, J=13, 7.0 Hz, 1H), 3.7 (m, 4H), 3.4 (m, 4H), 3.2 (m, 1H), 2.35 (m, 2H), 2.1 (m, 1H), 1.8 (m, 3H), 1.55 (m, 2H), 1.40 (d, J=7 Hz, 6H), 0.9 (t, J=7.0 Hz, 6H); LC/MS: 72% 474 (M+1) and 28% 492 (M+1+H2O).

Example 23

Morpholine-4-carboxylic acid {(S)-1-[(S)-1-(5-tert-butyl-1,2,4-oxadiazole-3-carbonyl)-propylcarbamoyl]-3,3-difluoro-hexyl}-amide

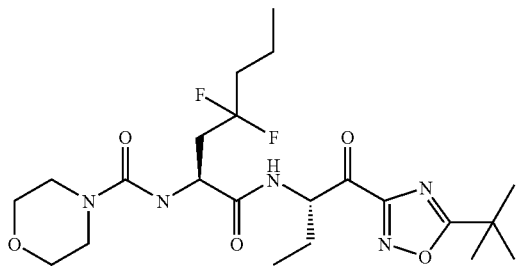

A solution of (S)-4,4-Difluoro-2-[(morpholine-4-carbonyl)-amino]-heptanoic acid (175 mg, 0.60 mmol) in dimethylformamide (6 mL) is treated successively with (S)-2-Amino-1-(5-tert-butyl-1,2,4-oxadiazol-3-yl)-butan-1-ol (240 mg, 1.13 mmol), O-(7-azabenzotriazol-1-yl)-N,N,N',N'-tetramethyluronium hexafluorophosphate (226 mg, 0.59 mmol) and diisopropylethylamine (0.104 mL, 0.60 mmol). Reaction stirred at room temperature overnight. Solvent evaporated under high vacuum. Residue taken up in ethyl acetate and washed with 1N hydrochloric acid, saturated aqueous bicarbonate solution and water, dried over Na2SO4 and solvent evaporated under reduced pressure. Crude purified on flash silica (10 g column) eluting with a mixture of ethyl acetate and heptane (2:1) to give Morpholine-4-carboxylic acid ((S)-1-{(S)-1-[(5-tert-butyl-1,2,4-oxadiazol-3-yl)-hydroxy-methyl]-propylcarbamoyl})-3,3-difluoro-hexyl)-amide as an oil (60 mg).

MS: 490 (M+H).

A solution of Morpholine-4-carboxylic acid ((S)-1-{(S)-1-[(5-tert-butyl-1,2,4-oxadiazol-3-yl)-hydroxy-methyl]-propylcarbamoyl})-3,3-difluoro-hexyl)-amide (57 mg, 0.117 mmol) in methylene chloride (3 mL) is treated with Dess-Martin periodinane (59 mg, 0.139 mmol) and stirred at room temperature for 90 minutes. The reaction mixture is washed with a solution of Na2S2O3 in water (0.26M), saturated aqueous bicarbonate solution and water, dried over Na2SO4 and the solvent evaporated under reduced pressure. The residue is purified by flash chromatography eluting with a mixture of ethyl acetate and heptane (1:1) to give Morpholine-4carboxylic acid {6(S)-1-[(S)-1-(5-tert-butyl-1,2,4-oxadiazole-3-carbonyl)-propylcarbamoyl]-3,3-difluoro-hexyl}-amide as a solid (41 mg).

MS: 488 (M+H).

Example 24

Morpholine-4-carboxylic acid {(S)-1-[1-(5-tert-butyl-1,2,4-oxadiazole-3-carbonyl)-propylcarbamoyl]-3,3-difluoro-4-phenyl-butyl}-amide

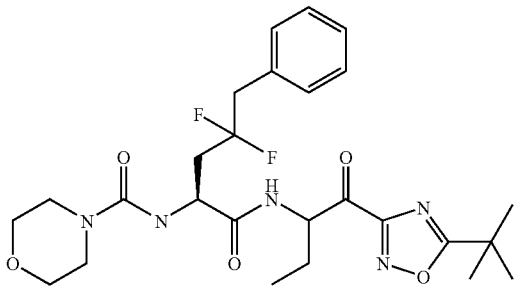

By proceeding in a similar manner to Example 23 above but using (S)-4,4-Difluoro-2-[(morpholine-4-carbonyl)-amino]-5-phenyl-pentanoic acid and (S)-2-Amino-1-(5-tert-butyl-1,2,4-oxadiazol-3-yl)-butan-1-ol there is prepared Morpholine-4-carboxylic acid {(S)-1-[1-(5-tert-butyl-1,2,4-oxadiazole-3-carbonyl)-propylcarbamoyl]-3,3-difluoro-4-phenyl-butyl}-amide as 7:3 mixture of diastereoisomers.

$^1$H NMR (CDCl$_3$) δ: 7.36-7.19 (m, 5H), 7.15 (d, J=7.1 Hz, 1H), 5.31 (m, 1H), 5.03 & 4.96 (2×d, J=7 Hz, 1H), 4.68 (m, 1H), 3.76-3.59 (m, 4H), 3.45-3.26 (m, 4H), 3.18 (t, J=16.8 Hz, 2H), 2.52-2.18 (m, 2H), 2.17-1.94 (m, 1H), 1.88-1.70 (m, 1H), 1.47 (s, 9H), 0.93 (t, J=7.4 Hz, 3H).

MS: 536 (M+H).

Example 25

Morpholine-4-carboxylic acid ((S)-3,3-difluoro-1-{(S)-1-[5-(4-fluoro-phenyl)-1,2,4-oxadiazole-3-carbonyl]-propylcarbamoyl}-butyl)-amide

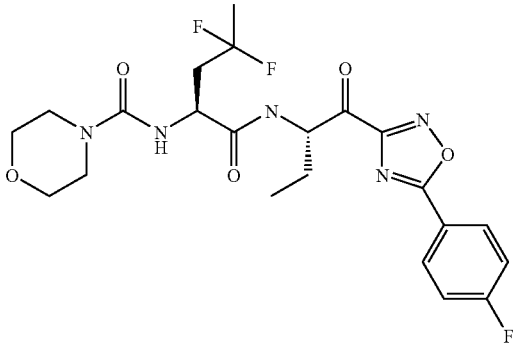

By proceeding in a similar manner to Example 23 above but using (S)-4,4-Difluoro-2-[(morpholine-4-carbonyl)-amino]-pentanoic acid and (S)-2-Amino-1-[5-(4-fluoro-phenyl)-1,2,4-oxadiazol-3-yl]-butan-1-ol there is prepared Morpholine-4-carboxylic acid ((S)-3,3-difluoro-1-{(S)-1-[5-(4-fluoro-phenyl)-1,2,4-oxadiazole-3-carbonyl]-propylcarbamoyl}-butyl)-amide ¹H NMR (CDCl₃) δ: 8.21 (m, 2H), 7.31 (d, J=6.8 Hz, 1H), 7.30-7.20 (m, 2H), 5.38 (m, 1H), 5.07 (d, J=6.8 Hz, 1H), 4.63 (m, 1H), 3.75-3.64 (m, 4H), 3.44-3.33 (m, 4H), 2.58-2.28 (m, 2H), 2.22-2.04 (m, 1H), 1.96-1.79 (m, 1H), 1.66 (t, J=18.8 Hz, 3H), 0.97 (t, J=7.4 Hz, 3H).

MS: 498 (M+H).

Example 26

Morpholine-4-carboxylic acid {(S)-1-[1-(5-cyclopropyl-1,2,4-oxadiazole-3-carbonyl)-propylcarbamoyl]-3,3-difluoro-4-phenyl-butyl}-amide

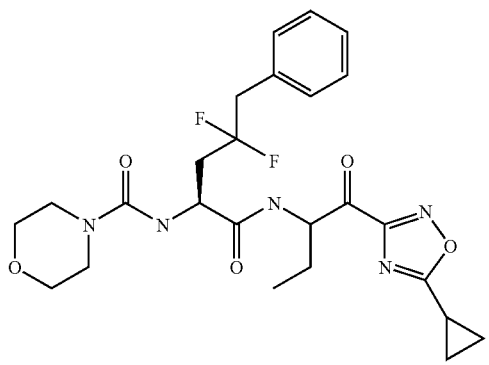

By proceeding in a similar manner to Example 23 above but using (S)-4,4-Difluoro-2-[(morpholine-4-carbonyl)-amino]-5-phenyl-pentanoic acid and (S)-2-Amino-1-(5-cyclopropyl-1,2,4-oxadiazol-3-yl)-butan-1-ol there is prepared Morpholine-4-carboxylic acid {(S)-1-[1-(5-cyclopropyl-1,2,4-oxadiazole-3-carbonyl)-propylcarbamoyl]-3,3-difluoro-4-phenyl-butyl}-amide as 3:1 mixture of diastereoisomers.

¹H NMR (CDCl₃) δ: 7.36-7.20 (m, 5H), 7.14 (d, J=7.1 Hz, 1H), 5.26 (m, 1H), 5.02 & 4.96 (2×d, J=7 Hz, 1H), 4.70 (m, 1H), 3.73-3.61 (m, 4H), 3.43-3.28 (m, 4H), 3.18 (t, J=16.5 Hz, 2H), 2.48-2.21 (m, 3H), 2.14-1.98 (m, 1H), 1.85-1.70 (m, 1H), 1.38-1.21 (m, 4H), 0.91 (t, J=7.5 Hz, 3H).

MS: 520 (M+H).

Example 27

Perhydro-1,4-oxazepine-4-carboxylic acid {(S)-1-[1-(5-cyclopropyl-1,2,4-oxadiazole-3-carbonyl)-propylcarbamoyl]-3,3-difluoro-hexyl}-amide

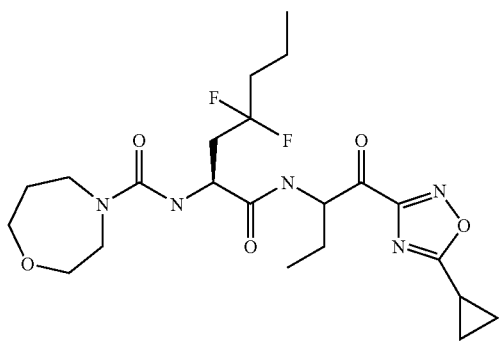

By proceeding in a similar manner to Example 23 above but using (S)-4,4-Difluoro-2-[(perhydro-1,4-oxazepine-4-carbonyl)-amino]-heptanoic acid and (S)-2-Amino-1-(5-cyclopropyl-1,2,4-oxadiazol-3-yl)-butan-1-ol there is prepared Perhydro-1,4-oxazepine-4-carboxylic acid {(S)-1-[1-(5-cyclopropyl-1,2,4-oxadiazole-3-carbonyl)-propylcarbamoyl]-3,3-difluoro-hexyl}-amide as 5:1 mixture of diastereoisomers.

¹H NMR (CDCl₃): 7.44 & 7.39 (2×d, J=7.3 Hz, 1H), 5.30 (m, 1H), 5.05 & 4.98 (2×d, J=6.5 Hz, 1H), 4.63 (m, 1H), 3.79-3.73 (m, 4H), 3.59-3.53 (m, 4H), 2.47-2.23 (m, 3H), 2.15-1.76 (m, 6H), 1.57-1.43 (m, 2H), 1.38-1.26 (m, 4H), 0.95 (t, J=7.3 Hz, 3H), 0.93 (t, J=7.2 Hz, 3H).

MS: 486 (M+H).

Example 28

Perhydro-1,4-oxazepine-4-carboxylic acid [(S)-1-(cyanomethyl-carbamoyl)-3,3-difluoro-hexyl]-amide

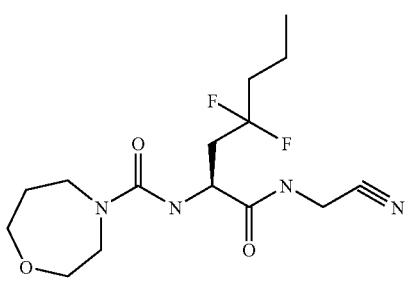

A suspension of Polystyrene bound carbodiimide (570 mg, 0.73 mmol) and 4,4-Difluoro-2-[([1,4]oxazepane-4-carbonyl)-amino]-heptanoic acid (135 mg) in DCM (10 mL) stirred for 10 min. HOBT (60 mg) added, stirred for 10 min. A suspension of amino acetonitrile hydrochloride (34 mg) and triethyl amine (52 µL) in DCM (5 mL) added and stirred overnight at room temperature. PS-Trisamine (493 mg) added and stirred at room temperature for 2 h 30 min. After filtration, filtrate diluted with DCM, washed with water, evaporated under reduced pressure and purified by column chromatography eluting with ethyl acetate heptane mixture to give Perhydro-1,4-oxazepine-4-carboxylic acid [(S)-1-(cyanomethyl-carbamoyl)-3,3-difluoro-hexyl]-amide as a solid.

LCMS: 100% 347 (M+H)

Example 29

Perhydro-1,4-oxazepine-4-carboxylic acid [(S)-1-((S)-1-cyano-propylcarbamoyl)-3,3-difluoro-hexyl]-amide

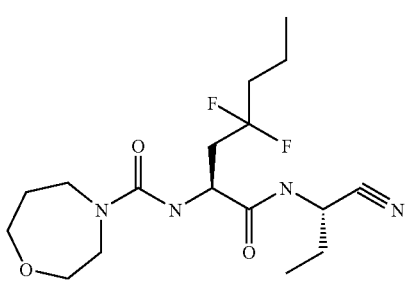

By proceeding in a similar manner to Example 28 above but using 4,4-Difluoro-2-[([1,4]oxazepane-4-carbonyl)-amino]-heptanoic acid and (S)-2-Amino-butyronitrile hydrochloride there is prepared Perhydro-1,4-oxazepine4-carboxylic acid [(S)-1-((S)-1-cyano-propylcarbamoyl)-3,3-fluoro-hexyl]-amide.
LCMS: 100% 375 (M+H).

Example 30

Morpholine-4-carboxylic acid [(S)-1-(1-cyano-cyclopropylcarbamoyl)-3,3-difluoro-hexyl]-amide

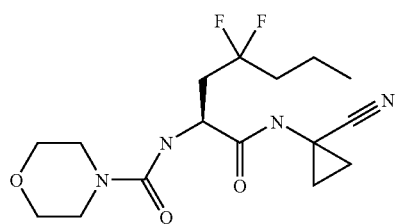

Prepared by reacting (S)-4,4-Difluoro-2-[(morpholine-4-carbonyl)-amino]-heptanoic acid and 1-Amino-cyclopropanecarbonitrile hydrochloride, using TOTU as the coupling agent and diisopropyl ethylamine as the base.
LCMS: 359 (M+H)

Example 31

Cathepsin S Assay

Solutions of test compounds in varying concentrations are prepared in 10 μL of dimethyl sulfoxide (DMSO) and then diluted into assay buffer (40 μL, comprising: MES, 50 mM (pH 6.5); EDTA, 2.5 mM; and NaCl, 100 mM, 0.5 mM DTT, 0.01% triton X-100).

Human cathepsin S (final concentration in the well is 1.74 nM) is added to the dilutions. The assay solutions are mixed for 5-10 seconds on a shaker plate, covered and incubated for 30 minutes at ambient temperature. Z-Val-Val-Arg-AMC (final concentration in the well is 0.08 mM) is added to the assay solutions and hydrolysis is followed spectrophotometrically at ($\lambda$460 nm) for 5 minutes. Apparent inhibition constants ($K_i$) are calculated from the enzyme progress curves using standard mathematical models.

Example 32

Cathepsin B Assay

Solutions of test compounds in varying concentrations are prepared in 10 μL of dimethyl sulfoxide (DMSO) and then diluted into assay buffer (comprising: MES 50 mM (pH 6); 2.5 mM EDTA, 2% DMSO and dithiothreitol (DTT), 2.5 mM).

Human cathepsin B (final concentration of 0.3 ng/μl) is added to the dilutions. The assay solutions are mixed for 5-10 seconds on a shaker plate, covered and incubated for 30 minutes at ambient temperature. Z-FR-pNa (final concentration of 100 μM) is added to the assay solutions and hydrolysis is followed spectrophotometrically at ($\lambda$405 nm) for 60 minutes. Apparent inhibition constants ($K_i$) are calculated from the enzyme progress curves using standard mathematical models.

Example 33

Cathepsin K Assay

Solutions of test compounds in varying concentrations are prepared in 10 μL of dimethyl sulfoxide (DMSO) and then diluted into assay buffer (40 μL, comprising: MES, 50 mM (pH 5.5); EDTA, 2.5 mM; and DTT, 2.5 mM). Human cathepsin K (0.0906 pMoles in 25 μL of assay buffer) is added to the dilutions. The assay solutions are mixed for 5-10 seconds on a shaker plate, covered and incubated for 30 minutes at ambient temperature. Z-Phe-Arg-AMC (4 nMoles in 25 μL of assay buffer) is added to the assay solutions and hydrolysis is followed spectrophotometrically at ($\lambda$460 nm) for 5 minutes. Apparent inhibition constants ($K_i$) are calculated from the enzyme progress curves using standard mathematical models.

Example 34

Cathepsin L Assay

Solutions of test compounds in varying concentrations are prepared in 10 μL of dimethyl sulfoxide (DMSO) and then diluted into assay buffer (40 μL, comprising: MES, 50 mM (pH 6); EDTA, 2.5 mM; and DTT, 2.5 mM). Human cathepsin L (10 μL of 0.2 ng/μL, final concentration of 0.02 ng/μl) is added to the dilutions. The assay solutions are mixed for 5-10 seconds on a shaker plate, covered and incubated for 30 minutes at ambient temperature. Z-Phe-Arg-AMC (10 μL of 0.1 mM, final concentration of 10 μM) is added to the assay solutions and hydrolysis is followed spectrophotometrically at ($\lambda$460 nm) for 30 minutes. Apparent inhibition constants ($K_i$) are calculated from the enzyme progress curves using standard mathematical models.

Compounds of the invention are tested according to the above-described assays for protease inhibition and observed to exhibit selective cathepsin S inhibitory activity. The apparent inhibition constants ($K_i$) for compounds of the invention, against Cathepsin S, are in the range from about $10^{-10}$ M to about $10^{-7}$ M.

Example 35

Representative Pharmaceutical Formulations Containing a Compound of Formula (I):

| ORAL FORMULATION | |
|---|---|
| Compound of Formula I, | 10-100 mg |
| Citric Acid Monohydrate | 105 mg |
| Sodium Hydroxide | 18 mg |
| Flavoring | |
| Water | q.s. to 100 mL |
| INTRAVENOUS FORMULATION | |
| Compound of Formula I, | 0.1-10 mg |
| Dextrose Monohydrate | q.s. to make isotonic |
| Citric Acid Monohydrate | 1.05 mg |
| Sodium Hydroxide | 0.18 mg |
| Water for Injection | q.s. to 1.0 mL |
| TABLET FORMULATION | |
| Compound of Formula I, | 1% |
| Microcrystalline Cellulose | 73% |
| Stearic Acid | 25% |
| Colloidal Silica | 1%. |

While there have been described and pointed out fundamental novel features of the invention as applied to a preferred embodiment thereof, it will be understood that various omissions and substitutions and changes, in the form and details of the composition and methods illustrated, may be made by those skilled in the art without departing from the spirit of the invention. For example, it is expressly intended that chemical radical substitutions and/or method steps, which perform substantially the same function in substantially the same way to achieve the same results are within the scope of the invention.

The invention is not limited by the embodiments described above which are presented as examples only but can be modified in various ways within the scope of protection defined by the appended patent claims.

We claim:

1. A compound having a structure of formula (I):

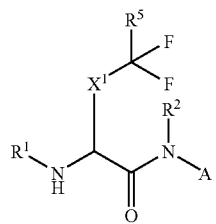

(I)

wherein

A is

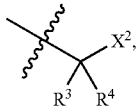

$X^1$ is methylene, ethylene or a bond;

$X^2$ is CN, CHO, C(O)C(O)NR$^7$R$^7$, C(O)C(O)NR$^7$R$^8$, C(O)C(O)R$^{13}$, C(O)C(O)OR$^{13}$, C(O)CH$_2$X$^3$R$^{13}$;

$X^3$ is selected from the group consisting of O, S(O)$_n$, CO, CONH, NHCO, NHSO$_2$ and SO$_2$NH;

$X^6$ is a bond or (C$_{1-2}$)alkylene;

$R^1$ is $R^{13}$C(O)—, $R^{13}$S(O)$_2$—, $R^{13}$OC(O)—, $R^8R^7$NC(O)—, $R^8R^7$NS(O)$_2$—; $R^{13}$S(O)$_2$NC(O)— or $R^{13}$C(O)NS(O)$_2$—;

$R^2$ is selected from the group consisting of hydrogen, (C$_{1-6}$)alkyl, (C$_{3-12}$)cycloalkyl(C$_{0-6}$)alkyl, hetero(C$_{5-12}$)cycloalkyl(C$_{0-6}$)alkyl, (C$_{6-12}$)aryl(C$_{0-6}$)alkyl or hetero(C$_{5-12}$)aryl(C$_{0-6}$)alkyl;

$R^3$ is selected from the group consisting of H, (C$_{1-6}$)alkyl, (C$_{3-12}$)cycloalkyl(C$_{0-6}$)alkyl, hetero(C$_{5-12}$)cycloalkyl(C$_{0-6}$)alkyl, (C$_{6-12}$)aryl(C$_{0-6}$)alkyl or hetero(C$_{5-13}$)aryl (C$_{0-6}$)alkyl optionally substituted by 1 to 5 radicals independently selected from a group consisting of (C$_{1-4}$)alkyl, cyano, halo, halo-substituted (C$_{1-4}$)alkyl, —X$^6$NR$^9$R$^9$, —X$^6$OR$^9$, —X$^6$SR$^9$, —X$^6$C(O)NR$^9$R$^9$, —X$^6$OC(O)NR$^9$R$^9$, —X$^6$C(O)OR$^9$, —X$^6$NC(O)OR$^9$, —X$^6$S(O)R$^{10}$, —X$^6$S(O)$_2$R$^{10}$ and —X$^6$C(O)R$^{10}$;

$R^4$ is H or (C$_{1-6}$)alkyl; or $R^3$ and $R^4$ taken together with the carbon atom to which both $R^3$ and $R^4$ are attached to form (C$_{3-8}$)cycloalkylene or (C$_{3-8}$)heterocycloalkylene;

$R^5$ is H, F, or $R^5$ is (C$_{1-9}$)alkyl, (C$_{3-12}$)cycloalkyl(C$_{0-6}$)alkyl, hetero(C$_{3-12}$)cycloalkyl(C$_{0-6}$)alkyl, (C$_{6-12}$)aryl(C$_{0-6}$)alkyl, hetero(C$_{5-13}$)aryl(C$_{0-6}$)alkyl each optionally substituted by 1 to 5 radicals independently selected from a group consisting of (C$_{1-4}$)alkyl, cyano, halo, halo-substituted(C$_{1-4}$)alkyl, —X$^6$NR$^9$R$^9$, —X$^6$OR$^9$, —X$^6$SR$^9$, —X$^6$C(O)NR$^9$R$^9$, —X$^6$OC(O)NR$^9$R$^9$, —X$^6$C(O)OR$^9$, —X$^6$NC(O)OR$^9$, —X$^6$S(O)R$^{10}$, —X$^6$S(O)$_2$R$^{10}$ and —X$^6$C(O)R$^{10}$;

$R^7$ is H, (C$_{1-6}$)alkyl, (C$_{3-12}$)cycloalkyl(C$_{0-6}$)alkyl, hetero(C$_{3-12}$)cycloalkyl(C$_{0-6}$)alkyl, (C$_{6-12}$)aryl(C$_{0-6}$)alkyl, hetero(C$_{5-13}$)aryl(C$_{0-6}$)alkyl, and halo substituted (C$_{1-6}$)alkyl; wherein $R^7$ is optionally substituted by 1 to 5 radicals independently selected from a group consisting of (C$_{1-4}$)alkyl, cyano, halo, halo-substituted (C$_{1-4}$)alkyl, —X$^6$NR$^9$R$^9$, —X$^6$OR$^9$, —X$^6$SR$^9$, —X$^6$C(O)NR$^9$R$^9$, —X$^6$OC(O)NR$^9$R$^9$, —X$^6$C(O)OR$^9$, —X$^6$NC(O)OR$^9$, —X$^6$S(O)R$^{10}$, —X$^{S(O)}{}_2$R$^{10}$ and —X$^6$C(O)R$^{10}$;

$R^8$ is selected from the group consisting of H, (C$_{1-6}$)alkyl, (C$_{3-12}$)cycloalkyl(C$_{0-6}$)alkyl, hetero(C$_{3-12}$)cycloalkyl(C$_{0-6}$)alkyl, (C$_{6-12}$)aryl(C$_{0-6}$)alkyl, and hetero(C$_{5-13}$)aryl(C$_{0-6}$)alkyl, or $R^7$ and $R^8$ together with the atom attached to form (C$_{3-8}$)cycloalkylene or (C$_{3-8}$)heterocycloalkylene;

$R^9$ at each occurrence independently is hydrogen, (C$_{1-6}$)alkyl or halo-substituted (C$_{1-6}$)alkyl;

$R^{10}$ is (C$_{1-6}$)alkyl or halo-substituted (C$_{1-6}$)alkyl;

$R^{13}$ is (C$_{1-6}$)alkyl, (C$_{3-12}$)cycloalkyl(C$_{0-6}$)alkyl, hetero(C$_{3-12}$)cycloalkyl(C$_{0-6}$)alkyl, (C$_{6-12}$)aryl(C$_{0-6}$)alkyl, hetero(C$_{5-13}$)aryl(C$_{0-6}$)alkyl, and halo substituted (C$_{1-6}$)alkyl; wherein $R^{13}$ is optionally substituted by 1 to 5 radicals independently selected from a group consisting of (C$_{1-4}$)alkyl, cyano, halo, halo-substituted (C$_{1-4}$)alkyl, —X$^6$NR$^9$R$^9$, —X$^6$OR$^9$, —X$^6$SR$^9$, —X$^6$C(O)NR$^9$R$^9$, —X$^6$OC(O)NR$^9$R$^9$, —X$^6$C(O)OR$^9$, —X$^6$NC(O)OR$^9$, —X$^6$S(O)R$^{10}$, —X$^6$S(O)$_2$R$^{10}$ and —X$^6$C(O)R$^{10}$; and n is zero or an integer 1 or 2;

and their corresponding N-oxides, and their prodrugs, and their protected derivatives, and their stereoisomers thereof; and the pharmaceutically acceptable salts of such compounds of formula (I) and their N-oxides and their prodrugs, and their protected derivatives, and their stereoisomers thereof.

* * * * *